United States Patent [19]

May et al.

[11] Patent Number: 5,538,966
[45] Date of Patent: Jul. 23, 1996

[54] CARBONIC ANHYDRASE INHIBITORS

[75] Inventors: Jesse A. May; Hwang-Hsing Chen, both of Fort Worth; Brian DuPré, Houston; Thomas R. Dean, Weatherford, all of Tex.

[73] Assignee: Alcon Laboratories, Inc., Fort Worth, Tex.

[21] Appl. No.: 374,470

[22] Filed: Jan. 20, 1995

Related U.S. Application Data

[63] Continuation-in-part of Ser. No. 184,430, Jan. 21, 1994, abandoned.

[51] Int. Cl.$^6$ .................... C07D 417/02; A61K 31/54
[52] U.S. Cl. ........................... 514/226.5; 544/48
[58] Field of Search .................... 544/48; 514/226.5

[56] References Cited

U.S. PATENT DOCUMENTS

| | | | |
|---|---|---|---|
| 4,177,193 | 12/1979 | Hromatka et al. | 549/64 |
| 4,224,445 | 9/1980 | Hromatka et al. | 544/212 |
| 4,230,873 | 10/1980 | Hromatka et al. | 549/64 |
| 4,619,939 | 10/1986 | Maren | 514/363 |
| 4,746,745 | 5/1988 | Maren | 548/139 |
| 4,927,821 | 5/1990 | Binder et al. | 514/226.5 |
| 5,093,332 | 3/1992 | Shepard et al. | 514/224.2 |
| 5,240,923 | 8/1993 | Dean et al. | 514/226.5 |

FOREIGN PATENT DOCUMENTS

| | | |
|---|---|---|
| 0479480A3 | 4/1992 | European Pat. Off. |
| 0617038A1 | 9/1994 | European Pat. Off. |
| 617705A5 | 12/1978 | Switzerland . |
| 2537070A1 | 8/1975 | United Kingdom . |
| WO91/15486 | 10/1991 | WIPO . |
| WO94/05674 | 3/1994 | WIPO . |

OTHER PUBLICATIONS

Buzas, et al., Bulletin de la Societe Chimique de France, 1960, Paris, France, pp. 793–803.

Primary Examiner—Mukund J. Shah
Assistant Examiner—Matthew V. Grumbling
Attorney, Agent, or Firm—Sally Yeager

[57] ABSTRACT

Compounds of the following formula are disclosed:
Compounds of Formula I are the topic of this invention:

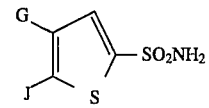

Wherein G, J and the two atoms of the thiophene ring to which they are attached form a six-membered ring chosen from

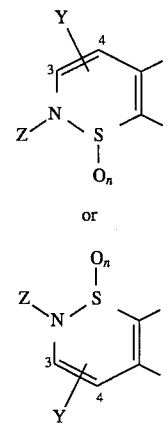

or The compounds are useful as carbonic anhydrase inhibitors.

23 Claims, No Drawings

CARBONIC ANHYDRASE INHIBITORS

This is a continuation-in-part of Ser. No. 08/184,430 filed on Jan. 21, 1994, now abandoned.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated intraocular pressure (IOP), which is considered to be causally related to the pathological course of the disease. Ocular hypertension is a condition wherein intraocular pressure is elevated but no apparent loss of visual function has occurred; such patients are considered to be a high risk for the eventual development of visual loss associated with glaucoma. If glaucoma or ocular hypertension is detected early and treated promptly with medications which effectively reduce elevated intraocular pressure, loss of visual function or its progressive deterioration can generally be ameliorated. Drug therapies which have proven to be effective for the reduction of intraocular pressure include both agents which decrease aqueous humor production and agents which increase the outflow facility. Such therapies are in general administered by one of two possible routes, topically (direct application to the eye) or orally.

One class of orally administered drugs which has been used for approximately thirty years to assist in the maintenance of intraocular pressure is carbonic anhydrase inhibitors. These agents inhibit the enzyme carbonic anhydrase, which is present in the ciliary process of the eye and intimately involved in the production of aqueous humor. Drugs of this class act through their ability to decrease the production of aqueous humor. Though these agents are efficacious and nontoxic to ocular tissues following oral administration, they are known to lead to detrimental, systemic (extraocular) side effects. The most serious, but rare, side effects are life-threatening blood dyscrasia and the formation of renal calculi. The more common side effects are nausea, dyspepsia, fatigue, impotence, depression, metabolic acidosis, and others which, although not generally life threatening, are sufficiently debilitating that patients frequently choose to discontinue therapy.

There is, therefore, a clear need for an inhibitor of carbonic anhydrase which would be topically effective, thereby eliminating, or significantly reducing, the detrimental side effects associated with oral administration. The compounds of the present invention are new sulfonamides which are carbonic anhydrase inhibitors useful for lowering IOP without producing significant systemic side effects when delivered topically to the eye.

Compounds of commonly assigned U.S. Pat. No. 5,240,923 possess a chiral center within the 3,4-dihydro-2H-thieno[3,2-e]-1,2-thiazine ring. It has been demonstrated that, in general, one of the two possible stereochemical representations about this center is more active in binding to the target enzyme, carbonic anhydrase. Therefore, for those compounds it is most advantageous to obtain the preferred enantiomer in optically pure form. This can be accomplished by procedures known in the art, such as resolution or synthesis; however, obtaining an optically pure compound can be laborious. Therefore, it is advantageous to employ compounds with no chiral centers, or with as few chiral centers as possible if such alternatives are available. Surprisingly, it was discovered that compounds of the present invention, which do not possess a chiral center within the heterocycle, 2H-thieno[3,2-e]-1,2-thiazine, are in general more potent inhibitors of carbonic anhydrase than the corresponding reduced compounds.

The class of non-steroidal antiinflammatory agents generally referred to as oxicams (e.g. piroxicam) can be considered to be structurally related to the compounds of present interest. Specifically, the compound known as tenoxicam and its numerous substituent variations are similar in that they share a common parent heterocyclic ring structure with the compounds of interest in the present invention: 2H-thieno[2,3-e]-1,2-thiazine. However, there have been no disclosures wherein a sulfamoyl ($SO_2NH_2$) group has been contemplated as a substituent within this group of compounds. A primary sulfamoyl group is a required substitution in the context of the present invention. Replacement of the fused benzene ring of piroxicam with a thiophene and further structural variations are disclosed in German Patent No. 2,537,070 and Swiss Patent No. 617,705 (and their related U.S. Pat. Nos. 4,230,873; 4,224,445 and 4,177,193); and European Patent No. 103,142 and U.S. Pat. Nos. 4,180,662 and 4,187,303.

U.S. Pat. No. 5,093,332 discloses 2,3-dihydro-1H-thieno[2,3-b][1,4]thiazine-6-sulfonamide 4,4-dioxides, which are shown to be weak inhibitors of carbonic anhydrase, for treating elevated intraocular pressure and glaucoma. U.S. Pat. Nos. 4,619,939 and 4,746,745 disclose sulfonamides and a process for reducing intraocular pressure by applying topically to the cornea a carbonic anhydrase inhibitor having a particular set of properties. The compounds of this invention are not disclosed in these patents.

SUMMARY OF THE INVENTION

The present invention is directed to new sulfonamides which can be used to lower and control IOP and control ocular hypertension and glaucoma in warm blooded animals, including man. The compounds are formulated in pharmaceutical compositions suitable for topical delivery to the eye. New intermediate compounds useful in making the sulfonamides are also disclosed.

The invention is also directed to methods for lowering and controlling IOP by the administration of the compositions comprising the sulfonamides of the present invention. The compositions are administered topically to the eye.

DETAILED DESCRIPTION OF THE INVENTION

Compounds consistent with Formula I are the topic of this invention:

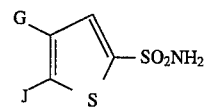

Wherein G, J and the two atoms of the thiophene ring to which they are attached form a six-membered ring chosen from

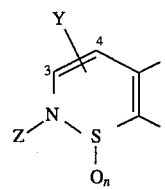

-continued or

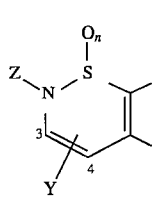

wherein if Z is $Z^1$, $Z^1$ is $C_{1-8}$alkyl;

$C_{1-3}$alkyl-$C_{3-6}$cycloalkyl;

$CH_2C(=O)R^7$; $CH_2C(=O)NR^2R^3$; $CH_2CN$;

$C_{2-8}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, CN, $NR^2R^3$, $SO_nR^4$ or $C(=O)R^5$;

$C_{1-4}$alkyl substituted with an aromatic group chosen from phenyl or Q either of which can be unsubstituted or substituted with one or more of $C_{1-4}$alkyl, $C_{1-4}$ alkoxy, hydroxy, halogen, nitrile, $NR^2R^3$, $SO_nR^4$, $C(=O)R^5$ or $C_{1-4}$alkyl which is substituted with hydroxy, $NR^2R^3$, halogen, $CO_2R^1$ or $C_{1-3}$alkoxy;

$C_{3-8}$alkenyl unsubstituted or substituted with hydroxyl, $C_{1-4}$alkoxy or $NR^2R^3$;

$C_{3-8}$alkynyl unsubstituted or substituted with hydroxyl, $C_{1-4}$alkoxy or $NR^2R^3$;

and if Z is $Z^2$, $Z^2$ is an aromatic group chosen from phenyl or Q either of which can be unsubstituted or substituted with one or more of $C_{1-4}$alkyl, $C_{1-4}$alkoxy, hydroxy halogen, nitrile, $NR^2R^3$, $SO_nR^4$, $C(=O)R^5$, or $C_{1-4}$alkyl which is substituted with hydroxy, $NR^2R^3$, halogen or $C_{1-3}$alkoxy;

Y is hydrogen;

$C_{1-8}$alkyl;

$C_{1-6}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, CN, $NR^2R^3$, $SO_nR^4$, or $C(=O)R^5$;

$C_{1-4}$alkyl substituted with an aromatic group chosen from phenyl or Q either of which can be unsubstituted or substituted with one or more of $C_{1-4}$alkyl, $C_{1-4}$ alkoxy, hydroxy, halogen, nitrile, $NR^2R^3$, $SO_nR^4$, $C(=O)R^5$ or $C_{1-4}$alkyl which is substituted with hydroxy, $NR^2R^3$, halogen, $CO_2R^1$ or $C_{1-3}$alkoxy;

$C_{3-8}$alkenyl unsubstituted or substituted with hydroxyl, $C_{1-4}$alkoxy or $NR^2R^3$;

$C_{3-8}$alkynyl unsubstituted or substituted with hydroxyl, $C_{1-4}$alkoxy or $NR^2R^3$;

$R^1$ is $C_{1-6}$alkyl;

$C_{1-6}$alkyl substituted with hydroxyl, halogen, $C_{1-4}$alkoxy, $NR^2R^3$ or $C(=O)R^5$;

phenyl which can be unsubstituted or substituted with one or more of $C_{1-4}$ alkyl, alkoxy, hydroxy or halogen;

$R^2$ and $R^3$ are independently chosen from hydrogen;

$C_{1-4}$alkyl; $CH_2CN$;

$C_{1-3}$alkyl-$C_{3-6}$cycloalkyl;

$C_{3-8}$cycloalkyl;

$C_{2-4}$alkyl substituted with hydroxyl, halogen, CN, $C_{1-4}$alkoxy or $C(=O)R^5$;

hydroxyl;

$C_{1-4}$alkoxy;

$C_{2-4}$alkoxy substituted with hydroxyl, $NR^2R^3$, halogen or $C_{1-4}$alkoxy;

$C_{3-8}$alkenyl unsubstituted or substituted with hydroxy, or $C_{1-4}$alkoxy;

$C_{3-8}$alkynyl unsubstituted or substituted with hydroxyl, or $C_{1-4}$alkoxy;

or further $R^2$ and $R^3$ together with the nitrogen atom to which they are attached can be incorporated into a saturated heterocyclic ring of 5 to 8 atoms which may include a second heteroatom selected from O, S or N, such as pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which can be unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$alkoxy, $C(=O)R^5$, $SO_nR^4$, $C_{1-4}$alkyl or $C_{1-4}$alkyl substituted with hydroxyl, halogen, $C_{1-4}$alkoxy or $C(=O)R^5$.

$R^4$ is $C_{1-4}$alkyl;

$C_{2-4}$alkyl substituted with hydroxyl, halogen, $NR^2R^3$ or $C_{1-3}$alkoxy;

$R^5$ is $C_{1-6}$alkyl;

$C_{1-6}$alkyl substituted with hydroxyl, halogen, $SO_nR^4$, $C_{1-4}$alkoxy, $NR^2R^3$ or $C(=O)R^6$;

$C_{1-4}$alkyl substituted with an aromatic group chosen from phenyl or Q either of which can be unsubstituted or substituted with one or more of $C_{1-4}$alkyl, $C_{1-4}$ alkoxy, hydroxy, halogen, nitrile, $NR^2R^3$, $SO_nR^4$ or $C_{1-4}$alkyl which is substituted with hydroxy, $NR^2R^3$, halogen or $C_{1-3}$alkoxy;

hydroxyl;

$C_{1-4}$alkoxy;

$C_{2-4}$alkoxy substituted with hydroxyl, $NR^2R^3$, halogen or $C_{1-4}$alkoxy;

$NR^2R^3$;

$R^6$ is $C_{1-4}$alkyl;

$C_{1-4}$alkoxy;

amino;

$C_{1-3}$alkylamino;

$(C_{1-3}$alkyl$)_2$amino;

$R^7$ is hydroxyl, $C_{1-4}$ alkoxy, $C_{1-4}$ alkoxy substituted with hydroxyl, $NR^2R^3$ or $C_{1-4}$ alkoxy;

n is 0, 1, or 2; and

Q is a monocyclic five or six membered heterocyclic ring system wherein one or more of the heteroatoms nitrogen, oxygen and/or sulfur are incorporated into the ring, such as thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

In compounds of Structure I substituent Y can be attached at position 3 or 4, or independent variations of substituent Y can be attached at positions 3 and 4. In the preferred embodiments of this invention substituent Y, when other than hydrogen, is attached at position 3. Selected compounds of Structure I can possess one or more chiral centers within substituents Y or Z, this invention contemplates all enantiomers, diastereomers and mixtures thereof.

In the above definitions, the total number of carbon atoms in a substituent group is indicated by the $C_{i-j}$ prefix where the numbers i and j define the number of carbon atoms; this definition includes both straight chain and branched chain alkyl groups.

It is important to recognize that a substituent may be present either singly or multiply when incorporated into the indicated structural unit. For example, the substituent halogen, which means fluorine, chlorine, bromine or iodine, would indicate that the alkyl or aryl portion to which it is attached may be substituted with one or more halogen atoms, which may be the same or different.

SYNTHESIS

Certain desirable compounds of Formula I can be prepared from the appropriate 2-substituted 2H-thieno[3,2-e]-1,2-thiazine 1,1-dioxide (1), where T is H, Br or Cl, and Z is as defined previously, as shown in Equation 1. Introduction of the sulfamoyl group at position six can be accomplished by treating compound 1 with a strong organometallic base such as n-butyllithium to form the organolithium intermediate which can be reacted with an appropriate electrophile, such as sulfuryl chloride or sulfur dioxide, to give the sulfonyl chloride or lithium sulfinate, respectively. Subsequent amination of these intermediates with either ammonia, in the first case, or with an electrophilic aminating reagent, for example, hydroxylamine-O-sulfonic acid, in the second provides the desired sulfonamides of Formula I. Alternately, conversion of the sulfinate salt to the sulfonyl chloride with, for example, N-chlorosuccinimide, chlorine or sulfuryl chloride followed by reaction with ammonia gives compounds of Formula I.

Equation 1:

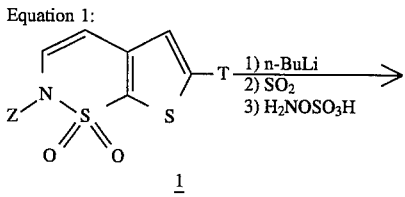

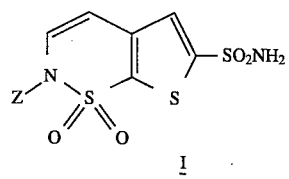

Intermediate 1 can be prepared by the methods shown in Equations 2–4. Alkylation of compound 2, which can be prepared as described in U.S. Pat. No. 5,153,192 and U.S. Pat. No. 5,240,923, using any of a variety of conditions known in the art, which in general involve the use of a base, such as sodium hydride or potassium carbonate, in an inert solvent, such as DMF, DMSO or ethanol, provides selectively alkylation at nitrogen, ring position two. The hydroxyl group of 3 can be activated toward subsequent elimination by formation of an intermediate sulfonate ester, such as by reaction with methanesulfonic anhydride in an inert solvent to give the methanesulfonate ester. Treatment of such sulfonate esters under generally basic conditions results in formation of the desired intermediate olefin 1 (Equation 2).

Equation 2

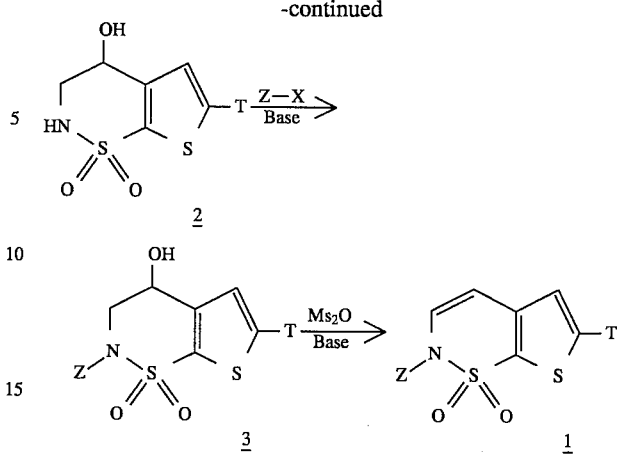

Alternately, activation of the hydroxyl group of compound 3 toward elimination can be accomplished by reaction with an appropriate aryl thionochloroformate to give intermediate 4. Treatment of 4 under conditions favorable for pyrolytic eliminations of the Chugaev reaction type [e.g. see *Organic Reactions*, 12, 57 (1962), *J. Amer. Chem. Soc.* 108, 800 (1986)], generally neat, at temperatures between 100° C. and 300° C. under vacuum, provide the desired olefin compound 1 (Equation 3).

Equation 3

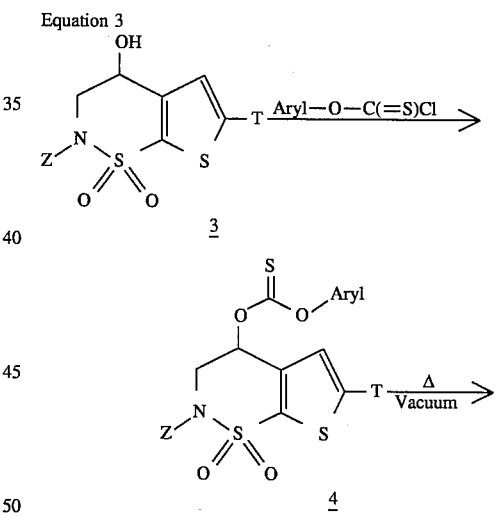

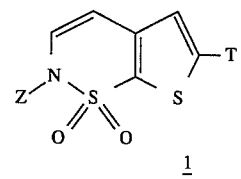

Chlorination of intermediate 3 with a suitable chlorinating agent such as thionyl chloride either neat or in the presence of an inert solvent provides intermediate 5; dehydrohalogenation under basic conditions provides the desired intermediate olefin 1 (Equation 4).

Equation 4

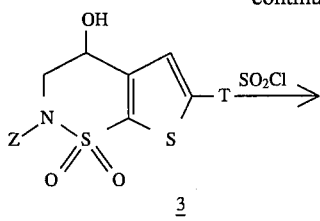

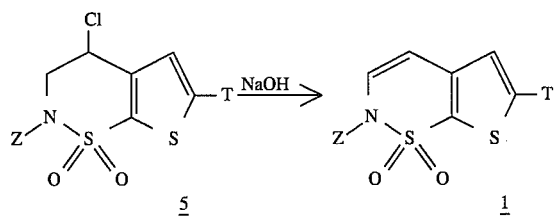

Furthermore, it can be advantageous to prepare certain intermediates 3 from compounds such as 6, prepared by alkylation of compound 2 with a suitable dibromoalkane in the manner analogous to that previously described for Equation 2. The hydroxyl group of 6 can be activated toward subsequent elimination by formation of a sulfonate ester, e.g. methanesulfonyl; treatment of such sulfonate esters under generally basic conditions results in formation of olefin 7. Reaction of olefin 7 with the desired nucleophile, e.g. amines or alcohols, using conditions well known in the art, provides intermediates 1 wherein Z is a substituted alkyl group such as aminoalkyl, i.e. $R^2R^3N$-alkyl-, or alkoxyalkyl, i.e. $R^1$-O-alkyl- (Equation 5).

Equation 5

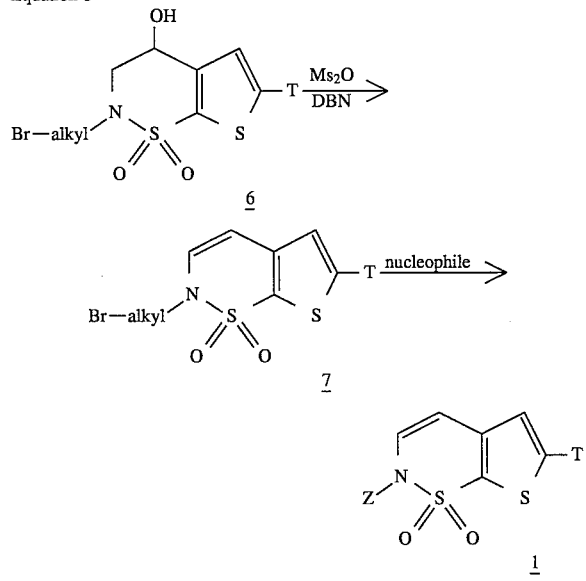

Intermediate compounds 3 can also be prepared as shown in Equation 6; this method is particularly preferred for those compounds of Formula I where Z is $Z^2$, as previously described. The requisite thiophene ketals (8), where T is H or Cl, can be readily prepared by standard methods well known to one skilled in the art from commercially available thiophene ketones. The incorporation of a sulfonamide or substituted sulfonamide at position two of the thiophene ketal (8) can be accomplished in a manner analogous to Equation 1, but in this case reacting the intermediate sulfonyl chloride with the appropriate arylamine to give intermediate 9. The conversion of these thiophenesulfonamides into the desired cyclic compounds of Formula I can be accomplished using a variety of procedures well known in the art; e.g. acid hydrolysis of the ketal followed by bromination of the ketone and subsequent base catalyzed cyclization of the α-haloketone provides intermediates of structure 3. Furthermore, the groups Z of intermediate 1 introduced according to Equations 2–6 can in many instances be further modified to furnish yet other novel compounds of Formula I using methods known to one skilled in the art.

Equation 6

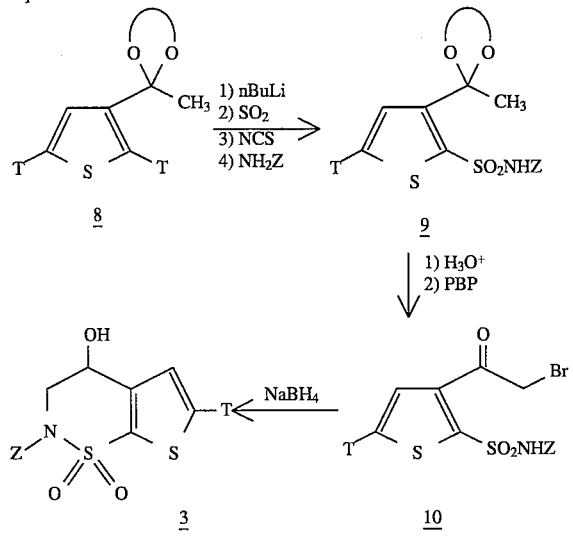

Alternately, it can be advantageous in certain cases to incorporate the sulfonamide group into the molecule prior to formation of the olefin. In these cases it may also be advantageous to protect the primary sulfonamide group from undergoing potentially undesirable reactions by incorporating a protecting group such as t-butylamine, a formamidine, or an imidate ester. Therefore, certain compounds of Formula I can best be prepared according to Equation 7. Alkylation of compound 11, which can be prepared as described in U.S. Pat. No. 5,240,923, with a haloalkylester, such as 2-bromoethyl acetate, using any of a variety of conditions known to the art provides intermediate 12. Transformation of the secondary hydroxyl group of 12 to a sulfonate ester, for example, by treatment with methanesulfonic anhydride, and subsequent treatment under basic conditions to effect elimination, provides, after cleavage of the ester, intermediate alcohol 13. The primary hydroxyl group of 13 can be transformed into groups ($Z^1$) of interest in the context of the present invention by a variety of functional group transformations. For example, an amino group can be incorporated by procedures known in the art, preferably by displacement of an aryl or alkyl sulfonate ester under mildly basic conditions with a primary or secondary amine, or by using conditions of the Mitsunobu reaction, diethyl azodicarbo-xylate-triphenylphosphine-amine. Deprotection of the sulfonamide group provides compounds of Formula I.

Equation 7

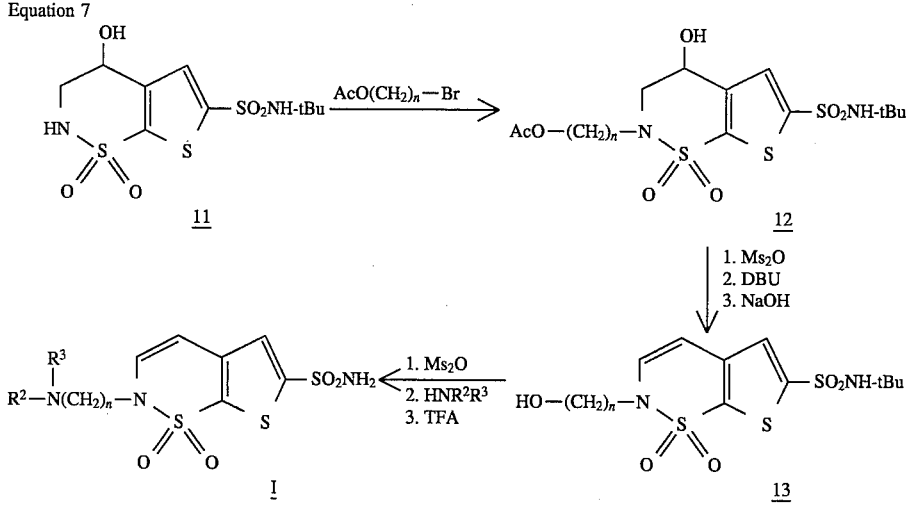

Other desirable compounds of Formula I can be prepared according to Equation 8 where $R^2$, $R^3$, T and Z are as described previously. Incorporation of the desired substituted sulfonamide at position two of the thiophene acetal 14 to give intermediate 15 can be accomplished in a manner analogous to that described for thiophene ketals in Equation 6. Alkylation of intermediate 15 with the desired α-halocarboxylic ester, e.g. ethyl bromoacetate provides intermediate 16 which can be cyclized by initial hydrolysis of the acetal followed by treatment of the aldehyde under basic conditions, e.g. DBU, to give 17. Modification of the ester group of 17 by methods known to the art provides desired 2,3 disubstituted compounds of Formula I wherein substituent Y at position three is as defined previously. For example, reduction of the ester group, with for example DIBAL, provides a primary alcohol (18) which can be readily converted to a sulfonate ester by known procedures; treatment of this sulfonate ester with the desired primary or secondary amine gives intermediate 19. Introduction of the primary sulfonamide can be accomplished by the sequence involving n-butyllithium, sulfur dioxide, and hydroxylamine-O-sulfonic acid (Equation 1) to give compounds of Formula I.

It can be advantageous in certain cases to introduce the primary sulfonamide prior to incorporating the amino group. In such cases direct sulfamoylation of 18 can be accomplished to give intermediate 20 by employing a procedure similar to that used for the sulfamoylation of 19. Amination of 20 by the same method used for the conversion of 18 to 19 provides compounds of Formula I.

Equation 8

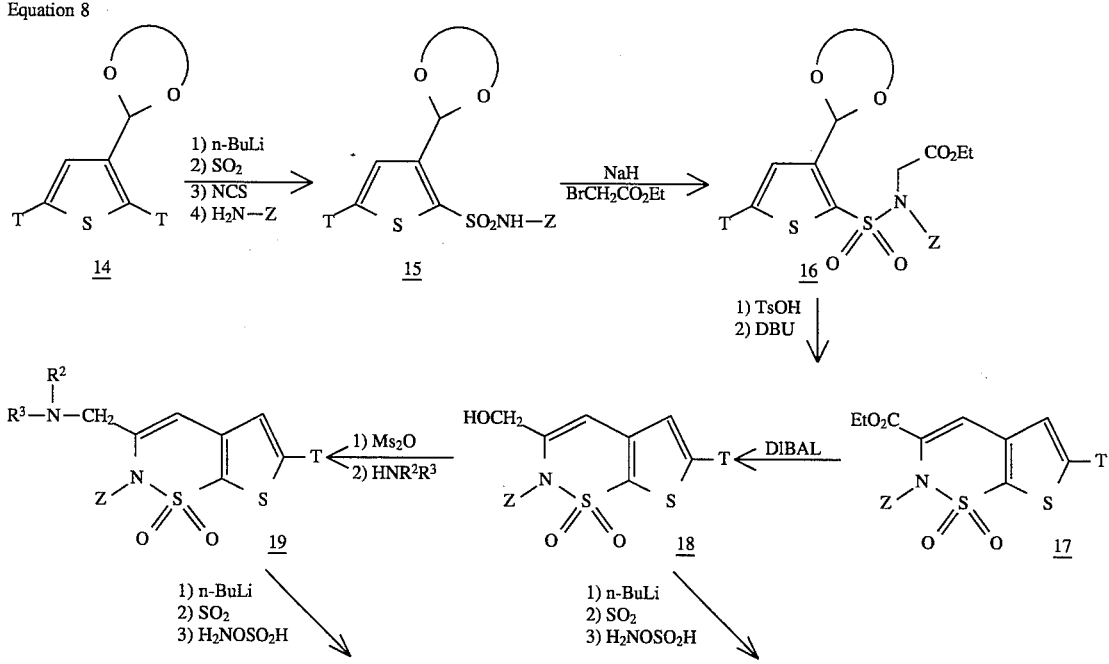

-continued

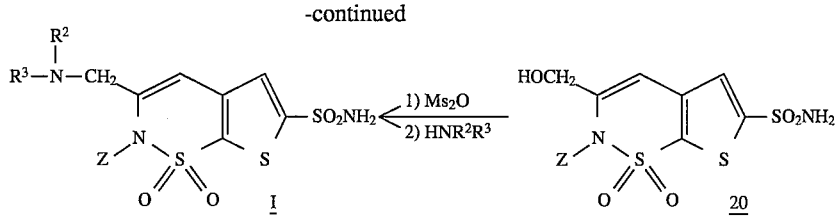

It can be desirable in certain cases to modify the substituent Z of Formula I (see Equation 9) to provide yet other compounds of Formula I. For example, where Z is $Z^1$ and $Z^1$ conditions known to the art provides the substituted alkylamides 26.

Equation 9

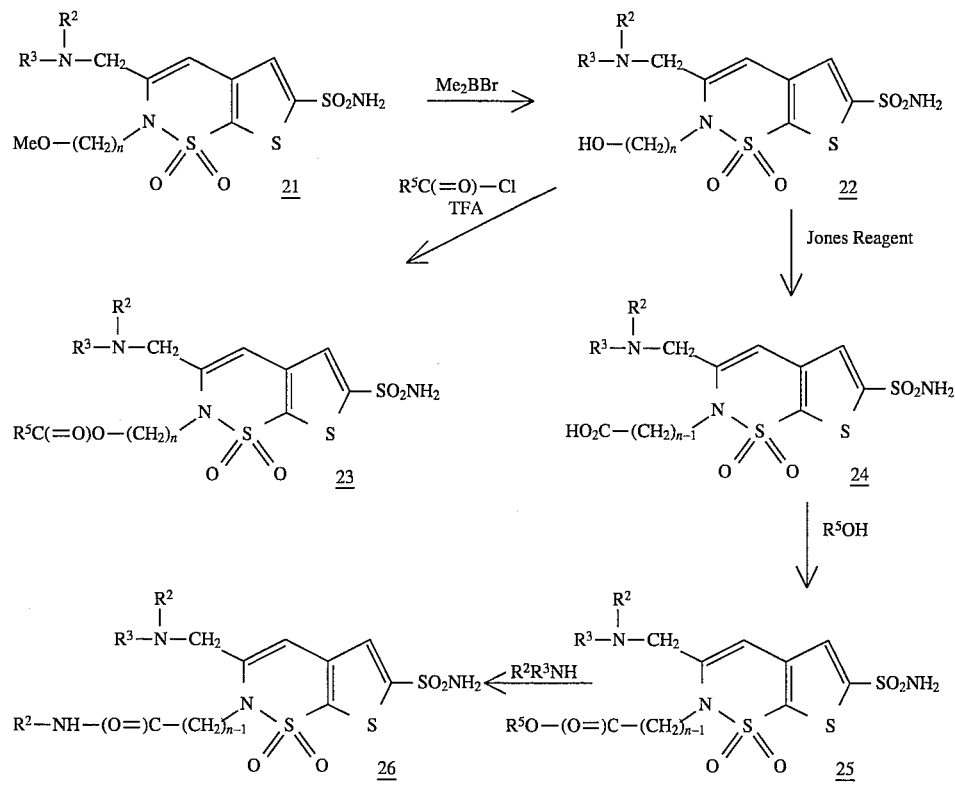

is alkoxyalkyl (e.g. 21), treatment under conditions suitable for ether cleavage, for example with a Lewis acid, such as borontribromide or bromodimethylborane, provides the ω-hydroxyalkyl substituent at position two (22) which can be selectively acylated by treatment with the desired acyl chloride under acidic conditions, for example in the presence of trifluoroacetic acid, to give compounds of Formula I wherein $Z^1$ is an acylated co-hydroxyalkyl group (23). Oxidation of the primary alcohol group of 22 with, for example, Jones reagent, provides the compound of Formula I where $Z^1$ is an alkylcarboxylic acid substituent, such as butanoic acid (24). Esterification of this carboxylic acid moiety can be readily accomplished by any of a variety of procedures known in the art, such as treatment with the desired alcohol in the presence of a suitable acid catalyst, such as sulfuric acid, to provide 25. Other esters of Formula I can be prepared from an ester so prepared by transesterification using various conditions known to the art (see, *Comprehensive Organic Transformations*, R. C. Larock, page 985). Amination of the alkylesters 25 by a variety of Yet other desirable compounds of Formula I, namely 2,3-disubstituted 2H-thieno[2,3-e]-1,2-thiazine-6-sulfonamide 1,1-dioxides, can be prepared in a manner analogous to that already described for 2,3-disubstituted 2H-thieno[3,2-e]-1,2-thiazine- 6-sulfonamide 1,1-dioxides in Equation 8, but using instead acetal 27 as the starting material (Equation 10). Selective metallation of 2,3-dibromothiophene with an organolithium base and subsequent treatment with an N, N-dialkylformamide, such as N,N-dimethylformamide or N-formylpiperidine, provides 3-bromo-2-thiophenecarboxaldehyde which can be protected as the acetal (27). Introduction of the desired substituted sulfonamide at position three of acetal 27 to give intermediate 28 can be accomplished in a manner analogous to that already described for thiophene acetals in Equation 8. It can be advantageous in certain cases to react the intermediate sulfonyl chloride prepared from 27 directly with an N-substituted glycine ester to provide intermediate 29. Cyclization of intermediate 29 and the subsequent transformation to compounds of Formula I proceeds as described in Equation 8.

Equation 10

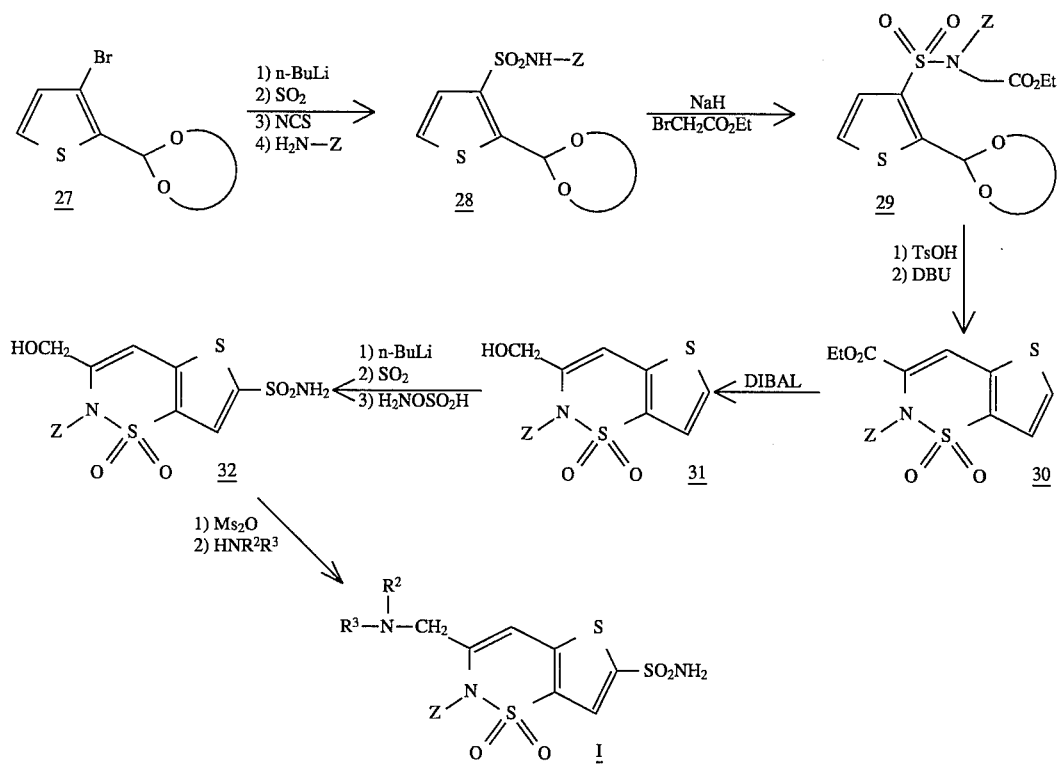

Additional compounds of Formula I can be prepared according to Equation 11, where T, Y, and Z are as described previously. Oxidation of alcohol 3 to ketone 33 can be accomplished by any of a variety of procedures known to the art, such as Jones reagent ($Cr_2O_3$/HOAc). Treatment of 33 with the desired Grignard reagent provides tertiary alcohol 34 which can be converted to the olefin 35 by treatment of the sulfonate ester under basic conditions as previously described in Equations 5 and 7. Introduction of the primary sulfonamide can be accomplished by the sequence involving n-butyllithium, sulfur dioxide, and hydroxylamine-O-sulfonic acid (Equation 1) to give compounds of Formula I.

Equation 11

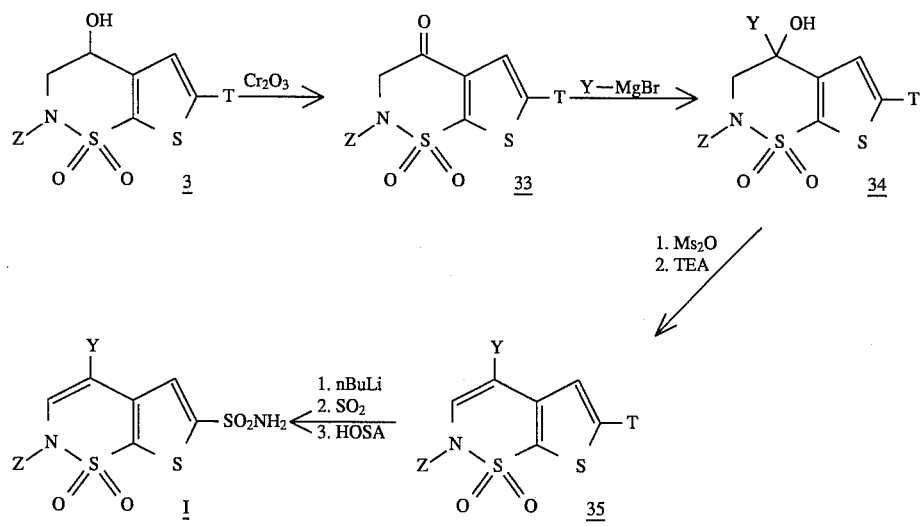

By following a sequence comparable to that described in Equation 11, but using instead ketone 36 as starting material, which can be prepared in a manner analogous to that illustrated in Austrian patent 352,744 (1979), it is possible to prepare yet other compounds of Formula I as shown in Equation 12.

Equation 12

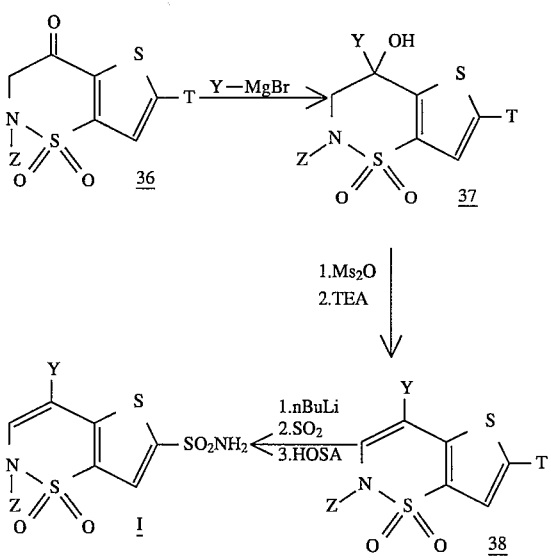

The compounds of this invention, Formula I, can be incorporated into various types of ophthalmic formulations for delivery to the eye. For example, these compounds can be combined with ophthalmologically acceptable preservatives, surfactants, viscosity enhancers, penetration enhancers, buffers, sodium chloride and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, Carbopol-940 or the like (carboxy vinyl polymers available from B. F. Goodrich Company) according to published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxypropylcellulose, methylcellulose, polyvinylpyrrolidone, or the like to improve the retention of the medicament in the conjunctival sac. Ophthalmic solutions, suspensions, ointments, gels, are the preferred dosage forms, typically at pH 4–8, the physiologically acceptable range for ophthalmic administration. The compounds will normally be contained in these formulations in the amount of 0.1% to 10% by weight, but preferably in an amount of 0.25% to 5% by weight. Thus, for topical presentation these formulations would be delivered to the surface of the eye 1–4 times/day depending upon the discretion of a skilled clinician.

The following examples are given to illustrate the preparation of compounds which are the subject of this invention but should not be construed as implying any limitations to the claims. The preferred compounds of Formula I are 2-substituted and 2,3-disubstituted 2H-thieno[3,2-e]-1,2-thiazine-6-sulfonamide 1,1-dioxides. Especially preferred compounds are those set forth in Examples 7, 10, 10.5, 11.1, 11.3, 11.4, 25 and 27. Most preferred is the compound of Example 11.1. The proton magnetic resonance spectrum of each compound of the Examples was consistent with the assigned structure.

EXAMPLE 1

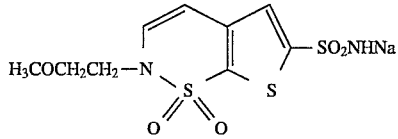

2-(2-Methoxyethyl)-2H-thieno[3,2-e]-1,2-thiazine-6-sulfonamide 1,1-dioxide Sodium Salt Step A: 3-(2,5,5-Trimethyl-1,3-dioxan-2-yl)-2-thiophenesulfonamide To a solution of 3-(2,5,5-trimethyl-1,3-dioxan-2-yl)thiophene (106 g, 0.5 mol) in hexane (1200 mL) at −60° C. was added a 2.5M solution of n-butyllithium in hexane (240 mL, 0.6 mmol) over 40 min. The mixture was allowed to warm to room temperature (approximately 1.5 hr) and then once again cooled to −60° C. and anhydrous THF (400 mL) added. Sulfur dioxide was passed over the surface of the reaction mixture for 30 min at which point the reaction mixture was allowed to warm to room temperature under a positive $SO_2$ pressure (approximately 1 hr). The solvent was removed and the residue dissolved in water (1200 mL) to which sodium acetate trihydrate (217.73 g, 1.6 mol) was added. The solution was cooled (ice bath) to 0° C. and hydroxylamine-O-sulfonic acid (107 g, 0.95 mol) was slowly added. The mixture was stirred at room temperature for 18 hr and then extracted with ethyl acetate. The combined extracts were washed with a saturated aqueous sodium bicarbonate solution, brine, dried ($Na_2SO_4$) and evaporated to give a viscous brown oil (174.05 g); this product was used in the next step without further purification.

Step B: 3-Acetyl-2-thiophenesulfonamide

The product from Step A (174.05 g, crude) was dissolved in a mixture of THF (1000 mL) and 1N HCl (1000 mL) and heated at reflux temperature for 1.5 hr. The THF was evaporated and the aqueous solution made basic by the addition of a saturated aqueous sodium bicarbonate solution. The mixture was cooled and the precipitate collected by filtration, washed with cold water and dried in vacuo to give the crude product (109.1 g,). Recrystallization from acetonitrile gave the desired product (81.5 g, 79%): mp 193°–196° C.

Step C: 3,4-Dihydro-2H-thieno[3,2-e]-1,2-thiazine-4-ol 1,1-dioxide

A solution of the product from Step B (102.6 g, 0.50 mol) in THF (3000 mL) was cooled to 10° C. and the addition of pyridinium bromide perbromide (183 g, 0.515 mol) commenced and continued as the temperature continued to drop to 0° C. After the addition was completed, the reaction mixture was allowed to warm to 14° C. (approximately 3 hr). The solvent was evaporated and the residue mixed with water; filtration provided the crude intermediate which was washed with cold water and dried in vacuo overnight to give 149.5 g of solid which was dissolved in ethanol (3000 mL) at room temperature and then chilled with ice; this solution was treated with $NaBH_4$ (19 g, 0.5 mol) and the mixture, which turned clear in about 15 min, was heated at 50° C. for 2 hr, and then stirred at room temperature for an additional 18 hr. The ethanol was evaporated and the residue dissolved in water; this aqueous solution was adjusted to a pH of 6 and then extracted with ethyl acetate. The extracts were washed with brine, dried and evaporated to give a residue which was triturated with cold ethyl acetate. The solid (crude product) was collected by filtration and the ethyl acetate soluble material was purified by column chromatography (silica, 20% to 50% ethyl acetate/hexane). These two batches of product were combined and recrystallized from ethyl acetate (59.6 g, 58%): mp 138°–140° C.

Step D: 4-(1-Ethoxyethoxy)-2-(1-ethoxyethyl)-3,4-dihydro-2H-thieno[3,2-e]-1,2-thiazine 1,1-dioxide A solution of the product from Step C (106.9 g, 0.521 mol) in THF (360 mL) was cooled to 0° C. and para-toluenesulfonic acid (3.6 g) was added. Ethyl vinyl ether (250 mL, 2.6 mol) was added over a period of 1.75 hr while maintaining the temperature of the reaction mixture below 5° C. The yellow solution was stirred at 0° C. for 1 hr, a saturated aqueous sodium bicarbonate solution (400 mL) was added and this mixture was extracted with ethyl acetate (3×250 ml). The combined extracts were dried ($Na_2SO_4$) and evaporated to give a residue which was purified by column chromatography (silica, hexane to 20% hexane/ethyl acetate) to give the desired product (78%) as a light yellow oil. This material was used in the next step.

Step E: 4-(1-Ethoxyethoxy)-2-(1-ethoxyethyl)-3,4-dihydro-N-(1,1-dimethylethyl)- 2H-thieno[3,2-e]-1,2-thiazine-6-sulfonamide 1,1-dioxide The product from Step D (125.6 g, 0.359 mol) was dissolved in THF (1200 mL, dry) and the solution cooled to −70° C. n-Butyllithium (2.5M in hexanes, 215 mL, 0.538 mol) was added slowly, after stirring at −70° C. for 1 hr sulfur dioxide was bubbled into the mixture until the pH reached 4. The reaction mixture was stirred at room temperature for 1 hr. The solvent was evaporated to give a residue which was dried in vacuo. The residue was dissolved in methylene chloride (1500 mL) and cooled to 0° C., N-chlorosuccinimide (62.3 g, 0.467 mol) was added in portions while maintaining the temperature of the reaction mixture at 0° C. The mixture was allowed to warm to room temperature and stirred at this temperature for 2 hr. Saturated aqueous sodium bicarbonate (500 mL) and brine (500 mL) were added and the organic layer was separated and washed with saturated aqueous sodium bicarbonate (250 mL) and brine (250 mL), dried ($MgSO_4$) and evaporated to give the sulfonyl chloride intermediate as a brown oil (132 g, 82%). The sulfonyl chloride (147 g, 0.327 mol) was dissolved in THF (900 mL) and cooled to 5° C. t-Butylamine (350 mL) was slowly added and the mixture was allowed to warm to room temperature, stirring continued for 20 hr. The solvent and excess amine were removed by evaporation to give a dark oil which was stirred with ethyl acetate (500 mL) and saturated aqueous sodium bicarbonate (250 mL). The organic layer was removed and the aqueous layer was washed with ethyl acetate (2×250 mL). The combined organic layers were dried ($MgSO_4$), filtered through silica gel, and evaporated to give the desired product as an oil (159 g, 99%).

Step F: 3,4-Dihydro-4-hydroxy-N-(1,1-dimethylethyl)-2H-thieno[3,2-e]-1,2-thiazine- 6-sulfonamide 1,1-dioxide A mixture of the product from Step E (158 g, 0.325 mol), THF (700 mL) and 2N HCl (180 mL) were stirred at room temperature for 20 hr. After evaporating the THF, the aqueous mixture was cooled to 0° C. and sodium bicarbonate (50 g) was carefully added followed by water (400 mL) and ethyl acetate (500 mL). The two layers were separated and the aqueous layer was extracted with ethyl acetate (250 mL). The combined organic extracts were washed with brine, dried ($MgSO_4$) and evaporated to give a foam which was triturated with methylene chloride (200 mL) to give a solid (81.7 g, 75%): mp 144°–147° C. Recrystallization of this solid from methylene chloride gave an off-white solid: mp 163°–165° C.

Step G: 3,4-Dihydro-4-hydroxy-N-(1,1-dimethylethyl)-2-(2-methoxyethyl)-2H-thieno[3,2-e]-1,2-thiazine-6-sulfonamide 1,1-dioxide The product from Step F (0.3 g, 0.88 mmol) was added to a suspension of sodium hydride (0.05 g of a 60% suspension in mineral oil, rinsed once with hexane, 1.25 mmol) in DMF (5 mL) at 0° C. The cooling bath was removed and the mixture was stirred for one hour at which point 2-bromoethyl methyl ether (0.09 mL, 0.97 mmol) was added. The mixture was stirred for 18 hr at room temperature, water was added and the mixture extracted with ethyl acetate (3×3 mL). The combined extracts were washed with water (10 mL), dried ($MgSO_4$) and evaporated to provide an oil which was purified by column chromatography (silica, hexane/ethyl acetate gradient) to give the desired product as an oil (0.35 g, 100%) which was used in the next reaction.

Step H: 2-(2-Methoxyethyl)-N-(1,1-dimethylethyl)-2H-thieno[3,2-e]-1,2-thiazine- 6-sulfonamide 1,1-dioxide The product from Step G (4.11 g, 10.31 mmol) and 4-dimethylaminopyridine (2.52 g, 20.6 mmol) were combined in dichloromethane (50 mL) and the mixture was cooled by means of an ice bath. Phenyl chlorothionoformate (2.1 mL, 15.5 mmol) was added rapidly to the mixture and the cooling bath removed. After three hours the mixture was washed with 2N HCl (15 mL), water (15 mL), saturated aqueous sodium chloride (20 mL), dried ($MgSO_4$) and evaporated to a residue which was purified by column chromatography (silica, hexane/ethyl acetate) to provide the desired product (2.14 g, 39%) as an oil. This oil was heated under vacuum (200° C./5 mm Hg) for approximately 5 minutes (until no more condensate collected) and then purified by column chromatography (silica, hexane/ethyl acetate) to provide the desired product (1.48 g, 97%) which was used in the next step.

Step I: 2-(2-Methoxyethyl)-2H-thieno[3,2-e]-1,2-thiazine-6-sulfonamide 1,1-dioxide Sodium Salt The product from Step H (1.48 g, 3.89 mmol) was mixed with trifluoroacetic acid (15 mL) and stirred for 36 hr at room temperature. Evaporation provided a residue which was dissolved in dichloromethane (15 mL) and washed with water (3×10 mL), saturated aqueous sodium chloride (15 mL), dried ($MgSO_4$) and evaporated to a residue which was purified by column chromatography (silica, gradient 3:1 hexane/ethyl acetate to 7:3 methylene chloride/methanol) to give the desired product (0.7 g, 55%) as an oil. To a solution of this oil in ethanol (2 mL) was added 2N NaOH (1.08 mL, 2.16 mmol). Ethyl ether was added to the cloud point and the product that precipitated was collected by filtration, washed with ether and dried under nitrogen to give the desired product (0.3 g) as a white solid: mp 95°–97° C. Analysis. Calculated for $C_9H_{11}N_2O_5S_3Na \cdot 2.0 H_2O$: C, 28.27; H, 3.95; N, 7.33. Found: C, 27.90; H, 3.64; N, 7.19.

EXAMPLE 2

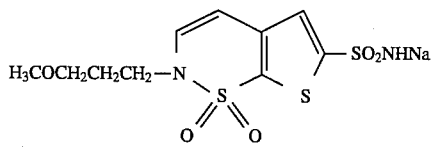

2-(3-Methoxypropyl)-2H-thieno[3,2-e]-1,2-thiazine-6-sulfonamide 1,1-dioxide Sodium Salt Step A: 6-Chloro-3,4-dihydro-2-(3-methoxypropyl)-4-O-phenoxythiocarbonyl- 2H-thieno[3,2-e]-1,2-thiazine 1,1-dioxide Sodium hydride (1.1 g of a 60% suspension in mineral oil, 27.53 mmol) was added in portions to a solution of 6-chloro-3,4-dihydro-4-hydroxy-2H-thieno[3,2-e]-1,2-thiazine 1,1-dioxide (6.0 g, 25.03 mmol) in dry DMF (100 mL) under nitrogen. The mixture was stirred for 1 hr, cooled to 0° C. in an ice bath and 3-bromopropyl methyl ether (3.83 g, 25.03 mmol) was added The mixture was stirred overnight at room temperature and evaporated to a residue which was mixed with water (100 mL) and extracted with ethyl acetate (5×20 mL). The extracts were combined, washed with saturated aqueous sodium chloride, dried (MgSO$_4$) and evaporated to provide an oil. A solution of this oil and 4-dimethylaminopyridine (4.58 g, 37.5 mmol) in 1,2-dichloroethane (100 mL) was cooled by means of an ice bath and phenyl chlorothionoformate (4.15 mL, 37.5 mmol) was added slowly. The cooling bath was removed and the mixture stirred at room temperature for 18 hr, diluted with a 3:1 mixture of hexane/ethyl acetate (200 mL) and filtered through silica gel. The filtrate was evaporated to a residue which was purified by column chromatography (silica, hexane to 3:1 hexane/ethyl acetate) to give the desired compound as an oil (5.1 g, 46%).

Step B: 6-Chloro-2-(3-methoxypropyl)-2H-thieno[3,2-e]-1,2-thiazine 1,1-dioxide

The product of Step A (5.1 g, 11.38 mmol) was heated under vacuum (200° C./0.5 mm Hg) until no more condensate formed (approximately 5 min). The flask was cooled to room temperature and the residue purified by column chromatography (silica, hexane to 3:1 hexane/ethyl acetate) to give the desired product as an oil (2.33 g, 70%) which was used in the next reaction.

Step C: 2-(3-Methoxypropyl)-2H-thieno[3,2-e]-1,2-thiazine-6-sulfonamide 1,1-dioxide Sodium Salt The product from Step B (2.31 g, 7.86 mmol) was dissolved in dry THF (35 mL) and cooled in a dry ice/isopropanol bath (−78° C.) under nitrogen. n-Butyllithium (4.1 mL of a 2.1M solution in hexanes, 8.65 mmol) was added dropwise and the mixture stirred for 45 min; excess sulfur dioxide was introduced into the flask until the solution tested acidic to moist litmus paper. The reaction mixture was evaporated to a residue which was dissolved in water (40 mL) followed by the addition of sodium acetate trihydrate (5.35 g, 39.3 mmol) and hydroxylamine-O-sulfonic acid (2,67 g, 23.58 mmol). This mixture was stirred at room temperature for 4 hr and extracted with ethyl acetate (5×8 mL). The combined extracts were washed with a saturated aqueous sodium chloride solution, dried (MgSO$_4$) and evaporated to a residue which was purified by column chromatography (silica, gradient 3:1 hexane/ethyl acetate to 7:3 methylene chloride/methanol) to give the desired product as an oil (0.91 g, 34%). This oil was converted to the sodium salt by dissolving it in ethanol (1.5 mL) and adding 2N NaOH (1.26 mL). Ethyl ether was added to the cloud point and the product which precipitated was isolated by filtration under nitrogen to give the desired salt (0.81 g, 90%): mp 90°–92° C. Analysis. Calculated for $C_{10}H_{13}N_2O_2S_3Na \cdot H_2O$: C, 30.30; H, 4.32; N, 7.07. Found: C, 30.29; H, 4.13; N, 6.97.

EXAMPLE 3

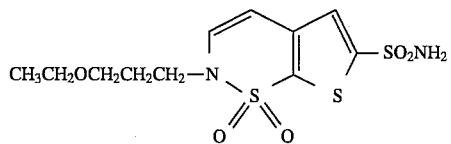

2-(3-Ethoxypropyl)-2H-thieno[3,2-e]-1,2-thiazine-6-sulfonamide 1,1-dioxide

Step A: 3-Bromopropyl Ethyl Ether

To a solution of 3-ethoxypropanol (5.0 g, 48 mmol) in carbon tetrachloride (19.1 g, 57.6 mmol) cooled to 0° C. was added triphenylphosphine (15.1 g, 57.6 mmol); this mixture was stirred for 3 hr, filtered through silica gel and evaporated to a residue which was distilled to give and oil (10.98 g). Redistillation of the oil from phosphorous pentoxide gave 3-bromopropyl ethyl ether (8.0 g, 100%): bp 142°–144° C.

Step B: 2-(3-Ethoxypropyl)-3,4-dihydro-2H-thieno[3,2-e]-1,2-thiazine-4-ol 1,1-dioxide A solution of the product from Example 1, Step C (13.0 g, 63.3 mmol) in DMF (50 mL) was added to a suspension of sodium hydride (2.5 g of a 60% slurry in mineral oil, washed with hexane, 63.3 mmol) in DMF (300 mL) at 0° C. After stirring for 45 min, the product from Step A (10.6 g, 63.3 mmol) was added and the mixture was stirred for 18 hr, during this time the temperature slowly increased to room temperature. The reaction mixture was diluted with cold water (300 mL) and extracted with ethyl acetate (5×10 mL). The combined extracts were washed with water (3×10 mL), saturated aqueous sodium chloride (20 mL), dried (MgSO$_4$) and evaporated to a residue which was purified by column chromatography (silica, gradient, 3:1 hexane/ethyl acetate to 7:3 methylene chloride/methanol) to provide a clear oil (13.1 g, 71%) which was used in the next step.

Step C: 4-(1-Ethoxyethoxy)-2-(3-ethoxypropyl)-3,4-dihydro-2H-thieno[3,2-e]-1,2-thiazine 1,1-dioxide A solution of the product from Step B (13.0 g, 44.77 mmol) and p-toluenesulfonic acid (0.20 g) in THF (250 mL) was cooled in an ice bath and ethyl vinyl ether (4.7 mL, 49.24 mmol) was added slowly; this mixture was stirred at room temperature for 18 hr. Sodium bicarbonate (2.0 g) was added and the mixture stirred for 30 min, washed with water (3×75 mL), saturated aqueous sodium chloride (100 mL) and dried (MgSO$_4$). The mixture was evaporated to a residue which was filtered through silica gel with 3:1 hexane/ethyl acetate to give a pale yellow oil (7.53 g, 46%) which was used in the next reaction.

Step D: 2-(3-Ethoxypropyl)-3,4-dihydro-4-hydroxy-2H-thieno[3,2-e]-1,2-thiazine- 6-sulfonamide 1,1-dioxide A solution of the product from Step C (13.25 g, 36.5 mmol) in THF (250 mL) was degassed under nitrogen and cooled to −60° C. in a dry-ice/isopropanol bath. n-Butyllithium (16.0 mL of a 2.5M solution, 40 mmol) was added slowly over 5 min and the mixture was stirred at −60° C. for 45 min followed by the introduction of excess sulfur dioxide gas into the flask. The mixture was allowed to warm to room temperature over two hours and the solvent was removed by evaporation. The residue was mixed with water (200 mL) and sodium acetate trihydrate (13.91 g, 102.2 mmol) followed by the addition of hydroxylamine-O-sulfonic acid (6,9 g, 61.32 mmol). The mixture was stirred at room temperature for 18 hr and then extracted with ethyl acetate (5×15 mL). The combined extracts were evaporated and the residue dissolved in THF (150 mL), mixed with 2N HCl (10 mL), warmed gently for 1 hr and then evaporated to a residue. The residue was mixed with ethyl acetate (100 mL) and water (100 mL). The organic layer was separated, washed with saturated aqueous sodium chloride, dried (MgSO$_4$) and evaporated to a residue which was purified by column chromatography (silica, gradient, 3:1 hexane/ethyl acetate to 7:3 methylene chloride/methanol) to provide a pale yellow solid (11.6 g, 86%): mp 140°–145° C. dec. Analysis. Calculated for $C_{11}H_{18}N_2O_6S_3$: C, 35.66; H, 4.90; N, 7.56. Found: C, 35.79; H, 4.80; N, 7.47.

Step E: 2-(3-Ethoxypropyl)-3,4-dihydro-4-hydroxy-2H-thieno[3,2-e]-1,2-thiazine- 6-(sulfonylacetimidate methyl ester) 1,1-dioxide The product from Step D (1.6 g, 4.32 mmol) was dissolved in dry acetonitrile (20 mL) and trimethylorthoacetate (11 mL) was added. The mixture was heated at reflux temperature for 18 hr and then evaporated to provide an oil (1.88 g, 100%) which was used without further purification.

Step F: 2-(3-Ethoxypropyl)-3,4-dihydro-4-phenoxythiocarbonyl-2H-thieno[3,2-e]- 1,2-thiazine-6-(sulfonylacetimidate methyl ester) 1,1-dioxide The crude product from Step E (1.88 g, 4.32 mmol) and 4-dimethylaminopyridine (0.8 g, 6.48 mmol) were mixed with 1,2-dichloroethane (25 mL) and cooled in an ice bath. Phenylthionocarbonyl chloride (0.7 mL, 5.2 mmol) was slowly added and the mixture allowed to warm to room temperature. The mixture was stirred for 18 hr, diluted with 3:1 hexane/ethyl acetate (100 mL) and filtered through silica gel. The filtrate was evaporated to a residue which was purified by column chromatography (silica, gradient elution hexane to 3:1 hexane/ethyl acetate) to give the desired product (0.79 g, 33%) and a secondary product wherein the protecting group had been removed (0.35 g, 16%).

Step G: 2-(3-Ethoxypropyl)-2H-thieno[3,2-e]-1,2-thiazine-6-sulfonamide 1,1-dioxide The combined products from Step F (0.79 g, 1.4 mmol and 0.35 g, 0.69 mmol) were heated under vacuum (200° C./0.5 mm Hg) until no more condensate formed (approximately 5 min). The flask was cooled to room temperature and the residue was dissolved in methanol (5 mL); 2N HCl (1.0 mL) was added. The mixture was heated at 50° C. for 2 hr and evaporated to a residue which was mixed with saturated aqueous sodium chloride and extracted with ethyl acetate (5×2 mL). The combined extracts were dried (MgSO$_4$) and evaporated to a residue which was purified by column chromatography (silica, 3:1 hexane/ethyl acetate to 7:3 methylene chloride/methanol) to give the desired product (0.42 g, 57%) as a white solid: mp 131°–132° C. Analysis. Calculated for $C_{11}H_{16}N_2O_5S_3$: C, 37.49; H, 4.58; N, 7.95. Found: C, 37.82; H, 4.56; N, 7.82.

EXAMPLE 4

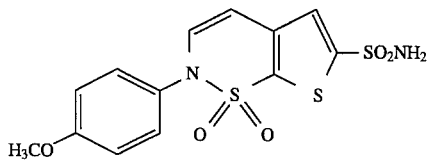

2-(4-Methoxyphenyl)-2H-thieno[3,2-e]-1,2-thiazine-6-sulfonamide 1,1-dioxide

Step A: 3-Acetyl-2-[(phenylmethyl)thio]-5-chlorothiophene

A mixture consisting of thiourea (858.4 g, 11.28 mol), benzyl bromide (1,930 g, 11.28 mol), THF (9000 ml), and water (3000 ml) was heated at reflux temperature for 2 hr followed by cooling to 50° C. To this solution was added 3-acetyl-2,5-dichlorothiophene (2000 g, 10.25 mol) and an aqueous solution of sodium hydroxide (2,200 g of 50% NaOH diluted to 3000 ml); this mixture was heated at reflux temperature for 4 hr, cooled to room temperature, and the two layers separated. The organic layer was diluted with ethyl acetate (6000 ml) and washed with water (3×2000 ml) and saturated aqueous sodium chloride, dried (MgSO$_4$) and the solvent evaporated to give a residue which was triturated with hexane. This solid was collected by filtration and dried to give the desired product (2,550 g, 88%): mp 86°–88° C.

Step B: 3-Acetyl-5-chloro-N-(4-methoxyphenyl)thiophene-2-sulfonamide

The product from Step A (15 g, 0.058 mol) was dissolved in glacial acetic acid (150 mL), water (15 mL) was added and the solution cooled to 3° C. Chlorine gas was slowly passed through the solution until the temperature reached 15° C. at which point the mixture was cooled to 5° C. before the addition of chlorine was continued; this sequence was repeated four times. The reaction mixture was poured into ice water (300 mL) and extracted with methylene chloride (2×200 mL). The combined extracts were washed with cold 2N NaOH (2×200 mL), brine (150 mL) and dried (MgSO$_4$). One half of this solution of sulfonyl chloride was evaporated to an oil which was dissolved in DMF, cooled (3° C.), and a solution of p-anisidine (7.14 g) in DMF (50 mL) was added. After stirring for 0.5 hr, the mixture was evaporated to a residue which was suspended in water and extracted with methylene chloride (2×70 mL). The combined extracts were dried (MgSO$_4$) and evaporated to a syrup which crystallized to give a yellow solid (3.15 g). The mother liquor was chromatographed (silica, 20% ethyl acetate/hexane) to give an additional quantity (1.66 g) of the desired product (total yield, 48%).

Step C: 6-Chloro-3,4-dihydro-4-hydroxy-2-(4-methoxyphenyl)-2H-thieno[3,2-e]- 1,2-thiazine 1,1-dioxide The product from Step B (4.20 g, 12.14 mmol) was dissolved in THF (40 mL) containing 30% HBr in acetic acid (0.1 equiv, 0.25 mL) and cooled to 3° C. A solution of pyridinium bromide perbromide (4.32 g, 13.52 mmol) in THF (20 mL) was added and the reaction mixture allowed to warm to room temperature. The THF was evaporated and the residue dissolved in ethanol (40 mL); this solution was cooled (3° C.), sodium borohydride (pellets, 3.25 g, 86.03 mmol) added and the reaction mixture stirred at 5° C. for 1 hr followed by heating at reflux temperature for 1 hr. The reaction mixture was evaporated to a residue which was suspended in water and the pH of this suspension was adjusted to 7 with saturated aqueous ammonium chloride. This mixture was extracted with ethyl acetate (3×50 mL) and the combined extracts were dried (MgSO$_4$). The products from two such reactions were purified by column chromatography (silica gel, 1:1 ethyl acetate/hexane) to give the desired product (3.6 g), mp 127°–132° C.; this material was used in the next reaction.

Step D: 6-Chloro-2-(4-methoxyphenyl)-2H-thieno[3,2-e]-1, 2-thiazine 1,1-dioxide

A solution of the product from Step C (1.4 g, 4.05 mmol) and 4-dimethylaminopyridine (0.74 g, 6.08 mmol) in 1,2-dichloroethane (10 mL) were cooled in an ice bath. Phenyl chlorothionoformate (0.67 mL, 4.86 mM) was added slowly. The cooling bath was removed and the mixture was stirred at room temperature for 18 hr, mixed with 3:1 hexane/ethyl acetate (25 mL) and filtered through silica gel. The filtrate was concentrated and heated under vacuum (200° C./0.5 mm Hg) approximately 5 min followed by cooling the mixture to room temperature. The residue was purified by column chromatography (silica gel, 3:1 hexane/ethyl acetate to 7:3 methylene chloride/methanol) which gave 0.91 g (65%) of the desired product as an oil which was not purified further.

Step E: 2-(4-Methoxyphenyl)-2H-thieno[3,2-e]-1,2-thiazine-6-sulfonamide 1,1-dioxide The product from Step D (0.9 g, 2.75 mmol) was dissolved in dry THF (10 mL) and degassed under nitrogen. The solution was cooled in a dry-ice/isopropanol bath (−78° C.) followed by the slow addition of n-butyllithium (2.2 ml of a 1.54M solution, 3.44 mmol). After stirring for 1 hr, sulfur dioxide gas was passed through the flask until the solution tested acidic to moist litmus paper at which point the cooling bath was removed. After stirring for 1 hr the solvent was evaporated and the residue mixed with water (10 mL). Sodium acetate trihydrate (1.87 g, 13.75 mmol) and hydroxylamine-O-sulfonic acid (0.94 g, 8.25 mmol) were added and this aqueous mixture stirred for 3 hr and then extracted with ethyl acetate (5×3 mL). The combined extracts were washed with a saturated aqueous solution of sodium chloride (10 mL), dried (MgSO$_4$) and evaporated to a residue which was partially purified by column chromatography (silica, 3:1 hexane/ethyl acetate to 7:3 methylene chloride/methanol) to give 0.19 g of a dark oil. To a solution of this oil in ethanol (2 mL) was added sodium hydroxide (0.3 mL of a 2N solution) followed by sufficient diethyl ether to precipitate the disodium salt which was collected by filtration: mp 98°–100° C. A solution of the sodium salt in water (3 mL) was acidified (pH 4) with 2N HCl and the precipitate collected by filtration to give the desired compound (67 mg, 6%) as a tan solid: mp 90°–92° C. Analysis. Calculated: C, 41.92; H, 3.25; N, 7.52. Found: C, 42.02; H, 3.31; N, 7.53.

EXAMPLE 5

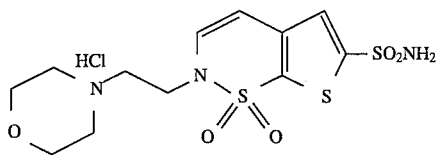

2-[2-(4-Morpholinyl)ethyl]-2H-thieno[3,2-e]-1,2-thiazine-6-sulfonamide 1,1-dioxide Hydrochloride Step A: 2-(2-Bromoethyl)-6-chloro-3,4-dihydro-4-hydroxy-2H-thieno[3,2-e]-1,2-thiazine 1,1-dioxide To a solution of 6-chloro-3,4-dihydro-4-hydroxy-2H-thieno[3,2-e]-1,2-thiazine 1,1-dioxide (2.0 g, 8.37 mmol) in DMF (50 mL) was added sodium hydride (0.37 g, 9.2 mmol), after stirring for 30 min 1,2-dibromoethane (2.36 g, 16.7 mmol) was added and this mixture was stirred at room temperature for 72 hr. The reaction mixture was poured into water and the aqueous mixture was extracted with ether. The combined extracts were dried (MgSO$_4$) and evaporated to an oil which was purified by column chromatography (silica, 30% ethyl acetate/hexane) to give 1.52 g (53%) of the desired product as a viscous syrup which was used in the next step.

Step B: 6-Chloro-2-[2-(4-morpholinyl)ethyl]-2H-thieno[3,2-e]-1,2-thiazine 1,1-dioxide To a solution of the product from Step A (0.76 g, 2.20 mmol) in tetrahydrofuran (30 mL) containing triethylamine (0.56 g, 5.5 mmol) was added methanesulfonic anhydride (0.75 g, 4.3 mmol); this mixture was stirred at room temperature for 1 hr and evaporated to dryness. The residue was dissolved in DMF (30 mL), triethylamine (1 mL) was added and the mixture heated at 150° C. for 45 min. Morpholine (3 mL, 34 mmol) was added to the reaction mixture and heating continued at the same temperature for 1 hr followed by heating at 100° C. for an additional hour. The volatiles were evaporated and the residue mixed with ethyl acetate; this mixture was washed with saturated aqueous sodium bicarbonate, dried (MgSO$_4$) and evaporated to an oil which was purified by column chromatography (silica, 50% ethyl acetate/hexane to ethyl acetate) to give a viscous oil (0.42 g, 58%) which was used in the next step.

Step C: 2-[2-(4-Morpholinyl)ethyl]-2H-thieno[3,2-e]-1,2-thiazine-6-sulfonamide 1,1-dioxide hydrochloride The product from Step B (1.00 g, 2.99 mmol) was dissolved in dry THF (30 mL) and cooled to −65° C. under nitrogen. n-Butyllithium (1.44 mL of a 2.5M solution in hexanes, 3.59 mmol) was added dropwise and the mixture stirred for 20 min during which time the temperature was allowed to increase to −45° C. The reaction mixture was cooled to −70° C. and sulfur dioxide was introduced into the flask for 5 min and the mixture was allowed to warm to room temperature. Evaporation of the reaction mixture provided a residue which was dissolved in water to which was added sodium acetate trihydrate (1.63 g, 12 mmol); this solution was cooled to 0° C. and hydroxylamine-O-sulfonic acid (0.676 g, 5.98 mmol) was added followed by stirring for 18 hr. The reaction mixture was extracted with ethyl acetate. The combined extracts were dried (MgSO$_4$) and evaporated to a crude oil which was purified by column chromatography (silica, 5% methanol/methylene chloride) to give a viscous oil (0.115 g). This oil was dissolved in ethyl acetate (2 mL) and treated with ethanolic hydrogen chloride (2 mL). The suspension which formed was evaporated to a solid which was triturated with ethyl acetate, filtered and dried (vacuum) to give the desired product (105 mg, 17%): mp 234°–236° C. Analysis. Calculated for $C_{12}H_{18}ClN_3O_5S_3$: C, 34.65; H, 4.36; N, 10.10. Found: C, 34.69; H, 4.41; N, 10.04.

EXAMPLE 6

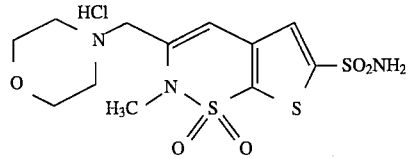

2-Methyl-3-(4-morpholinylmethyl)-2H-thieno[3,2-e]-1,2-thiazine-6-sulfonamide 1,1-dioxide hydrochloride Step A: N-[[3-(1,3-dioxolan-2-yl)-2-thienyl]sulfonyl]-N-methyl-glycine Ethyl Ester To a solution of thiophene-3-carboxaldehyde ethylene acetal (5.82 g, 37.3 mmol) in anhydrous THF (50 mL) at −70° C. was added 2.5M n-butyllithium (16.4 mL, 41 mmol) over 10 min. The solution was stirred at −50° C. for 10 min, cooled to −70° C. for 30 min and sulfur dioxide was passed over the reaction mixture for 5 min. The mixture was allowed to warm to ambient temperature, the volatiles were evaporated and methylene chloride (200 mL) was added. The suspension was cooled (ice bath) and N-chlorosuccinimide (6.47 g, 48.5 mmol) was added. This mixture was stirred at ambient temperature for 2 h, filtered and the filter pad was washed with ethyl acetate (200 mL). The combined filtrates were added to a solution of sarcosine ethyl ester hydrochloride (15.0 g, 97.6 mmol) in saturated aqueous sodium bicarbonate (100 mL) and the mixture stirred for 4 h at ambient temperature. After the organic layer was separated, the aqueous layer was extracted with ethyl acetate (2×100 mL), the combined extracts were dried (MgSO₄) and evaporated to dryness. Purification by column chromatography (silica, 30 to 50% ethyl acetate/hexane) gave an oil (8.95 g, 72%).

Step B: Ethyl 2-methyl-2H-thieno[3,2-e]-1,2-thiazine-3-carboxylate

A mixture of the product from Step A (8.80 g, 26.3 mmol) and 4-toluenesulfonic acid (1.0 g) in acetone (250 mL) was stirred overnight at ambient temperature. Water (0.5 mL) was added and this mixture was stirred for 4 h followed by addition of a saturated aqueous solution of sodium bicarbonate (50 mL) and evaporation of the acetone. The aqueous mixture was extracted with ethyl acetate (2×200 mL) and the combined extracts were dried (MgSO₄) and evaporated to give crude aldehyde which was dissolved in ethyl acetate (150 mL). DBN (0.5 g) was added and the mixture heated at reflux temperature for 2 h, cooled and washed with a saturated aqueous solution of sodium bicarbonate (50 mL). The ethyl acetate solution was dried (MgSO₄) and evaporated to a residue which was purified by column chromatography (silica, 30 to 50% ethyl acetate/hexane) to give the desired product as a white solid (5.05 g, 70%).

Step C: 2-Methyl-2H-thieno[3,2-e]-1,2-thiazine-3-methanol

To a solution of the product from Step B (1.00 g, 3.66 mmol) in anhydrous THF (20 mL) at −70° C. was added DIBAL (1.0M, 7.69 mL, 7.69 mmol). The mixture was warmed to ambient temperature and stirred for 2 h, additional DIBAL (20 mmol) was added and the reaction was stirred for 18 h. Methanol (100 mL) was added and the reaction mixture was evaporated to a residue which was suspended in 2N HCl (50 mL) and extracted with ethyl acetate (2×80 ml). The combined extracts were dried (MgSO₄) and evaporated to give a solid which was recrystallized from ethyl acetate/hexane to give the desired product (0.80 g, 95%): mp 128°–130° C.

Step D: 2-Methyl-3-(4-morpholinylmethyl)-2H-thieno[3,2-e]-1,2-thiazine

To a solution of the product from Step C (0.79 g, 3.42 mmol) and triethylamine (1.04 g, 10.3 mmol) in anhydrous THF (30 mL) at ambient temperature was added methanesulfonic anhydride (0.89 g, 5.13 mmol) with stirring. After 30 min morpholine (2 mL) was added and the mixture stirred for 1 h at ambient temperature and then heated at reflux temperature for 1 h. The volatiles were evaporated and a saturated aqueous solution of sodium bicarbonate (80 mL) was added. This mixture was extracted with ethyl acetate (2×100 mL) and the combined extracts were dried (MgSO₄) and evaporated to give a viscous oil which was purified by column chromatography (silica, 30 to 50% ethyl acetate/hexane) to give a white solid (0.82 g, 84%): mp 104°–106° C.

Step E: 2-Methyl-3-(4-morpholinylmethyl)-2H-thieno[3,2-e]-1,2-thiazine-6-sulfonamide 1,1-dioxide Hydrochloride To a mixture of the product from Step D (0.30 g, 1.04 mmol) in anhydrous THF (30 mL) under nitrogen at −65° C. was added 2.5N n-butyllithium (0.63 mL, 1.56 mmol) over 5 min. The mixture was stirred at −50° C. for 10 min and at −65° C. for 1 h. Sulfur dioxide was passed over the mixture for 5 min and the mixture was allowed to warm to ambient temperature followed by evaporation to dryness. Ice water (50 mL) and a saturated aqueous solution of sodium bicarbonate (50 mL) were added and this mixture was extracted with ethyl acetate (100 mL). Hydroxylamine-O-sulfonic acid (0.294 g, 2.60 mmol) was added to the aqueous mixture and stirring continued for 3 h. The mixture was extracted with ethyl acetate (2×100 mL) and the combined extracts were dried (MgSO₄) and evaporated to give the free base (0.098 g, 26%) which was converted to the hydrochloride salt by treatment with 1.5 N HCl in ethanol: mp 231°–233° C. Analysis: Calculated for $C_{12}H_{18}ClN_3O_5S_3 \cdot 0.5\ H_2O$: C, 33.91; H, 4.51; N, 9.89. Found: C, 33.95; H. 4.58; N, 9.75.

EXAMPLE 7

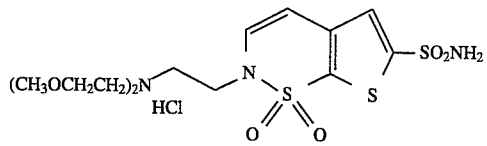

2-[2-[Bis(2-methoxyethyl)amino]ethyl]-2H-thieno[3,2-e]-1,2-thiazine-6-sulfonamide 1,1-dioxide Hydrochloride Step A: 2-[2-(Acetyloxy)ethyl]-3,4-dihydro-4-hydroxy-N-(1,1-dimethyl)ethyl-2H-thieno[3,2-e]-1,2-thiazine-6-sulfonamide 1,1-dioxide To a solution of the product of Example 1, Step F (3.00 g, 8.82 mmol) in anhydrous DMF (50 mL) at ambient temperature under nitrogen was added sodium hydride (60% dispersion in mineral oil, 0.424 g, 10.59 mmol). The mixture was stirred for 20 min, cooled (ice bath) and 2-bromoethyl acetate (2.21 g, 13.2 mmol) was added. Stirring continued at this temperature for 2 h followed by warming the reaction mixture to ambient temperature and stirring at this temperature for 18 h. The mixture was poured into an ice/sodium bicarbonate mixture (100 mL) and extracted with ethyl acetate (2×200 mL). The combined extracts were dried (MgSO₄) and evaporated to a residue which was purified by column chromatography (silica, 50% ethyl acetate/hexane) to give a foamy residue (3.36 g, 89%).

Step B: 2-(2-Hydroxyethyl)-N-(1,1-dimethylethyl)-2H-thieno[3,2-e]-1,2-thiazine- 6-sulfonamide 1,1-dioxide To a solution of the product from Step A (3.36 g, 7.89 mmol) and 2,6-lutidine (3.00 mL, 25.7 mmol) in anhydrous THF (30 mL) under nitrogen was added methanesulfonic anhydride (2.06 g, 11.8 mmol). This mixture was stirred for 30 min at ambient temperature followed by evaporation to a residue. Anhydrous DMF (50 mL) and DBU (1 mL) were added to the residue and this mixture was heated at 165° C. (bath temperature) for 20 min and evaporated to dryness. Methanol (50 mL) and 2N NaOH (20 mL) were added to the residue and this mixture was stirred for 2 h at ambient temperature. Methanol was evaporated and the aqueous mixture was extracted with ethyl acetate (2×100 mL). The combined extracts were dried (MgSO₄) and evaporated to give the desired product as an oil (2.78 g, 96%).

Step C: 2-[2-[Bis(2-methoxyethyl)amino]ethyl]-N-(1,1-dimethylethyl)-2H-thieno[3,2-e]-1,2-thiazine-6-sulfonamide 1,1-dioxide To a solution of the product of Step B (1.02 g, 2.79 mmol) and triethylamine (0.84 g, 8.36 mmol) in anhydrous THF (50 mL) was added methanesulfonic anhydride (0.80 g, 4.18 mmol) under nitrogen. This mixture was stirred at ambient temperature for 30 min followed by evaporation to a residue which was dissolved in ethyl acetate (80 mL) and washed with a saturated aqueous solution of sodium bicarbonate (50 mL). The organic phase was dried (MgSO₄) and evaporated to give a solid (1.06 g) which was dissolved in anhydrous DMF (50 mL) and bis-(2-methoxyethyl)amine (5 mL) was added and the mixture heated at reflux temperature for 1 h, cooled and poured into a saturated solution of sodium bicarbonate (100 mL). The solution was extracted with ethyl acetate (2×100 mL) and the combined extracts were dried (MgSO$_4$) and evaporated to give a crude oil which was purified by column chromatography (silica, 50 to 100% ethyl acetate/hexane) to give a viscous oil (0.89 g, 66%).

Step D: 2-[2-[Bis(2-methoxyethyl)]amino]ethyl]-2H-thieno [3,2-e]-1,2-thiazine- 6-sulfonamide 1,1-dioxide Hydrochloride The product from Step C (0.89 g, 1.85 mmol) was dissolved in trifluoroacetic acid (8 mL) and the resulting solution was stirred at ambient temperature for 18 h. Evaporation gave a residue which was mixed with a saturated aqueous solution of sodium bicarbonate (50 mL) and extracted with ethyl acetate (2×80 mL). The combined extracts were dried (MgSO$_4$) and evaporated to a residue which was purified by column chromatography (silica, 3 to 5% methanol/methylene chloride) to give an oil (0.74 g) which was converted to the hydrochloride salt by treatment with 2N HCl in ethanol (0.63 g, 79%): mp 60°–65° C. Analysis. Calculated for $C_{14}H_{24}ClN_3O_3$: C, 36.39; H, 5.24; N, 9.10. Found: C, 36.46; H, 5.28; N, 9.01.

EXAMPLE 8

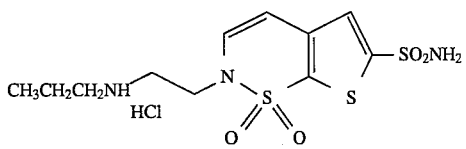

2-[2-(Propylamino)ethyl]-2H-thieno[3,2-e]-1,2-thiazine-6-sulfonamide 1,1-dioxide Hydrochloride Step A: 2-[2-(Propylamino)ethyl]-N-(1,1-dimethylethyl)-2H-thieno[3,2-e]-1,2-thiazine- 6-sulfonamide 1,1-dioxide To a solution of the product from Example 7, Step B (1.02 g, 2.79 mmol) and triethylamine (0.84 g, 8.36 mmol) in anhydrous THF (50 mL) was added methanesulfonic anhydride (0.80 g, 4.18 mmol) with stirring under nitrogen. The volatiles were evaporated after 30 min and the residue dissolved in ethyl acetate (80 mL). This mixture was washed with a saturated aqueous solution of sodium bicarbonate (50 mL), dried (MgSO$_4$) and evaporated to give a solid. The solid (1.55 g from two batches) was dissolved in a mixture of anhydrous DMF (40 mL) and 1-propylamine (6 mL) and heated at reflux temperature for 1 h followed by evaporation to a residue which was added to a saturated aqueous solution of sodium bicarbonate (100 mL). This mixture was extracted with ethyl acetate (2×100 mL) and the combined extracts were dried (MgSO$_4$) and evaporated to an oil which was purified by column chromatography (silica, 6% methanol/methylene chloride) to give a viscous oil (1.17 g, 84%).

Step B: 2-[2-(Propylamino)ethyl]-2H-thieno[3,2-e]-1,2-thiazine-6-sulfonamide 1,1-dioxide Hydrochloride The product from Step A (0.37 g, 0.90 mmol) was dissolved in trifluoroacetic acid (5 mL) and the solution was stirred at ambient temperature for 18 h. Evaporation gave a residue which was mixed with a saturated aqueous solution of sodium bicarbonate (50 mL) and this mixture was extracted with ethyl acetate (2×80 mL). The combined extracts were dried (MgSO$_4$) and evaporated to a residue which was purified by column chromatography (silica, 10% methanol/methylene chloride) to give an oil (0.19 g). Treatment with 1.5N HCl in ethanol gave the hydrochloride salt (0.18 g, 50%): mp 208°–210° C. Analysis. Calculated for $C_{11}H_{18}ClN_3O_4S_3$: C, 34.06; H, 4.68; N, 10.83. Found: C, 34.13; H, 4.67; N, 10.78.

EXAMPLE 9

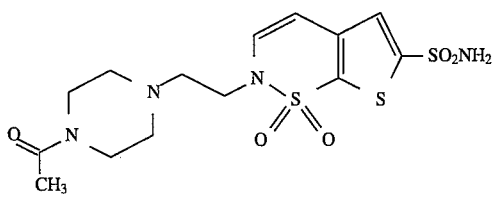

2-[2-[4-Acetyl-(1-piperazinyl)]ethyl]-2H-thieno[3,2-e]-1,2-thiazine-6-sulfonamide 1,1-dioxide Step A: 2-[2-[4-Acetyl-(1-piperazinyl)]ethyl]-N-(1,1-dimethyl)ethyl-2H-thieno[3,2-e]-1,2-thiazine-6-sulfonamide 1,1-dioxide To a solution of Example 7, Step B (2.78 g, 7.60 mmol) and triethylamine (2.30 g, 22.8 mmol) in anhydrous THF (50 mL) was added methanesulfonic anhydride (2.17 g, 11.4 mmol); this mixture was stirred at ambient temperature for 30 min followed by evaporation to give a residue which was dissolved in EtOAc (200 mL); this solution was washed with a saturated aqueous solution of sodium bicarbonate (80 mL), dried (MgSO$_4$) and evaporated to give a solid (3.45 g). A portion of this solid (1.70 g) was dissolved in anhydrous DMF (50 mL), 1-acetylpiperazine (2.40 g, 18.7 mmol) was added and the mixture was heated at reflux temperature for 1 h, cooled, poured into ice water (150 mL) and this mixture was extracted with ethyl acetate (2×100 mL). The combined extracts were dried (MgSO$_4$) and evaporated to a residue which was purified by column chromatography (silica, ethyl acetate to 10% methanol/ethyl acetate) to give a viscous oil (1.30 g, 73%) which solidified upon standing: mp 135°–138° C.

Step B: 2-[2-[4-Acetyl-(1-piperazinyl)]ethyl]-2H-thieno[3, 2-e]-1,2-thiazine- 6-sulfonamide 1,1-dioxide A solution of the product from Step A (1.30 g) in trifluoroacetic acid (15 mL) was stirred at ambient temperature for 18 h and evaporated to dryness. The residue was suspended in a saturated aqueous solution of sodium bicarbonate (80 mL) and this mixture was extracted with ethyl acetate (2×100 mL). The combined extracts were dried (MgSO$_4$) and evaporated to a residue that was purified by column chromatography (silica, ethyl acetate to 10% ethanol/ethyl acetate) to give a solid which was recrystallized from methanol/methylene chloride to give the desired product (0.59 g, 52%): mp 180°–183° C. Analysis. Calculated for $C_{14}H_{20}N_4O_5S_3$: C, 39.98; H, 4.79; N, 13.32. Found: C, 40.02; H, 4.78; N, 13.23.

EXAMPLE 10

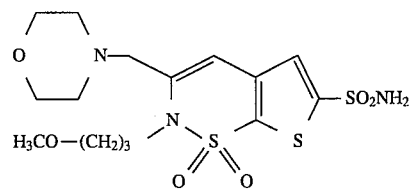

2-(3-Methoxypropyl)-3-(4-morpholinylmethyl)-2H-thieno[3,2-e]-1,2-thiazine- 6-sulfonamide 1,1-dioxide Hydrochloride Step A: N-[[3-(1,3-Dioxolan-2-yl)-2-thienyl]sulfonyl]-glycine Ethyl Ester A solution of 3-(1,3-dioxolan-2-yl)-thiophene-2-sulfonyl chloride, prepared from thiophene-3-carboxaldehyde ethylene acetal (13.27 g, 85.1 mmol) as described in Example 6, Step A, was combined with glycine ethyl ester hydrochloride (33.99 g, 221 mmol) and a saturated aqueous solution of sodium bicarbonate (250 mL). After stirring for 18 hr at ambient temperature, the organic layer was separated, dried (MgSO$_4$) and evaporated to a residue which was purified by column chromatography (silica, 40% ethyl acetate/hexane) to give an oil (16.55 g, 61%).

Step B: Ethyl 2-(3-methoxypropyl)-2H-thieno[3,2-e]-1,2-thiazine-3-carboxylate 1,1-dioxide A solution of potassium t-butoxide in t-butanol (1M, 15.7 mL, 15.7 mmol) was added to a solution of the product of Step A (4.80 g, 14.95 mmol) in anhydrous DMF (50 mL) at 0° C. followed by 1-bromo-3-methoxypropane (3.43 g, 22.4 mmol) and sodium iodide (0.2 g). The mixture was stirred for 5 h at ambient temperature, poured into ice water (300 mL) and extracted with ethyl acetate (2×200 mL). The combined extracts were dried (MgSO$_4$), filtered and evaporated to give a viscous liquid which was dissolved in acetone (300 mL); p-toluenesulfonic acid (0.4 g) was added and this mixture was heated at reflux temperature for 4.5 h. A saturated aqueous solution of sodium bicarbonate (100 mL) was added to the reaction mixture and acetone was evaporated. The aqueous mixture was extracted with ethyl acetate (2×200 mL) and the combined extracts were dried (MgSO$_4$), filtered and evaporated to give crude aldehyde which was dissolved in ethyl acetate (100 mL). DBN (0.2 g) was added and the mixture heated at reflux temperature for 2 h under nitrogen. The mixture was cooled, quenched with a 2N HCl (50 mL) and extracted with ethyl acetate (2×150 mL). The combined extracts were dried (MgSO$_4$) and evaporated to a syrup which was purified by column chromatography (silica, 30% ethyl acetate/hexane) to give a white solid (2.68 g, 54%): mp 82°–83° C.

Step C: 2-(3-Methoxypropyl)-2H-thieno[3,2-e]-1,2-thiazine-3-methanol 1,1-dioxide To a solution of the product from Step B (3.70 g, 11.18 mmol) in anhydrous THF (50 mL) at ambient temperature under nitrogen was added DIBAL (50 mL of a 1.0 M solution, 50.0 mmol). After stirring for 4 h the reaction mixture was cooled (ice bath) and 2N HCl (100 mL) was added over a 10 min period. THF was evaporated and the aqueous mixture was extracted with ethyl acetate (2×100 mL). The combined extracts were dried (MgSO$_4$), filtered and evaporated to give a viscous oil (3.23 g), which was used in the next step without further purification.

Step D: 2-(3-Methoxypropyl)-3-(4-morpholinylmethyl)-2H-thieno[3,2-e]-1,2-thiazine- 1,1-dioxide To a solution of the product from Step C (1.30 g, 4.50 mmol) and triethylamine (1.36 g, 13.5 mmol) in anhydrous THF (30 mL) at ambient temperature was added methanesulfonic anhydride (1.18 g, 6.75 mmol). After stirring for 30 min, morpholine (5 mL) was added; this mixture was stirred at ambient temperature for 18 h and then heated at reflux for 1 h. The volatiles were evaporated and a saturated aqueous solution of sodium bicarbonate (100 mL) was added. The mixture was extracted with ethyl acetate (2×100 mL) and the combined extracts were dried (MgSO$_4$) and evaporated to give a viscous oil which was purified by column chromatography (silica, 30 to 50% ethyl acetate/hexane) to give a viscous oil (1.51 g, 94%).

Step E: 2-(3-Methoxypropyl)-3-(4-morpholinylmethyl)-2H-thieno[3,2-e]-1,2-thiazine- 6-sulfonamide 1,1-dioxide Hydrochloride n-Butyllithium (3.35 mL of a 2.5M solution, 8.38 mmol) was added to a solution of the product from Step D (1.50 g, 4.19 mmol) in anhydrous THF (60 mL) under nitrogen at −70° C. After stirring at this temperature for 30 min, a stream of sulfur dioxide was passed through the mixture (5 min) which was allowed to warm to room temperature and then evaporated to a residue. A saturated aqueous solution of sodium bicarbonate (150 mL) was added to the residue and this mixture was extracted with ethyl acetate (100 mL). The aqueous mixture was cooled (ice bath) and hydroxylamine-O-sulfonic acid (1.42 g, 12.6 mmol) was added; this mixture was stirred for 15 h and extracted with ethyl acetate (2×100 mL). The combined extracts were dried (MgSO$_4$) and evaporated to a residue which was purified by column chromatography (silica, 80 to 100% ethyl acetate/hexane) to give an oil (0.81 g) which was dissolved in ethyl acetate, treated with 1.5M HCl/EtOH (1 mL) and evaporated to give the hydrochloride salt (0.69 g, 35%): mp 145°–149° C. Analysis. Calculated for $C_{15}H_{24}ClN_3O_6S_3$: C, 38.00; H, 5.10; N, 8.86. Found: C, 37.90; H, 5.15; N, 8.78.

By following the above procedure but using instead n-propylbromide, i-butylbromide or cyclopropylmethylbromide in Step B the following compounds were prepared:

1. 3-(4-Morpholinylmethyl)-2-propyl-2H-thieno[3,2-e]-1,2-thiazine-6-sulfonamide 1,1-dioxide hydrochloride, mp 233° C.

2. 2-(2-Methylpropyl)-3-(4-morpholinylmethyl)-2H-thieno[3,2-e]-1,2-thiazine- 6-sulfonamide 1,1-dioxide, mp 180°–181° C.

3. 2-(Cyclopropylmethyl)-3-(4-morpholinylmethyl)-2H-thieno[3,2-e]-1,2-thiazine- 6-sulfonamide 1,1-dioxide hydrochloride, mp 110° C.

By following the above procedure but using the appropriate alkylbromide instead of 1-bromo-3-methoxypropane in Step B the following compounds were prepared:

4. 3-(4-Morpholinylmethyl)-2-(2-propenyl)-2H-thieno[3,2-e]-1,2-thiazine-6-sulfonamide 1,1-dioxide, mp 136°–138° C.

5. 2-Ethyl-3-(4-morpholinylmethyl)-2H-thieno[3,2-e]-1,2-thiazine-6-sulfonamide 1,1-dioxide hydrochloride, mp 239°–241 ° C.

By following the above procedure but using propylbromide in Step B and propargylamine in Step D the following compound was prepared:

6. 2-Propyl-3-[(2-propynylamino)methyl]-2H-thieno[3,2-e]-1,2-thiazine-6-sulfonamide 1,1-dioxide, mp 136°–138° C.

EXAMPLE 11

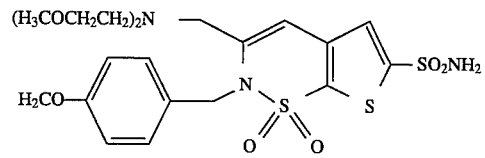

3-[[Bis(2-methoxyethyl)amino]methyl]-2-(4-methoxyphenylmethyl)-2H-thieno[3,2-e]-1,2-thiazine-6-sulfonamide 1,1-dioxide Step A: N-[[3-(1,3-Dioxolan-2-yl)-2-thienyl]sulfonyl]-N-(4-methoxyphenylmethyl) glycine Ethyl Ester To a solution of the product from Example 10, Step A (2.80 g, 8.72 mmol) in anhydrous DMF (40 mL) at 0° C. was added a solution of potassium t-butoxide in t-butanol (1M, 9.16 mL, 9.16 mmol) followed by 4-methoxybenzyl chloride (1.78 g, 11.34 mmol). The solution was stirred at ambient temperature for 4 h, poured into 2N HCl (50 mL), diluted with water (150 mL) and extracted with ethyl acetate (2×120 mL). The combined extracts were dried (MgSO₄), filtered and evaporated to give a viscous oil (3.91 g) which was used in the next step.

Step B: Ethyl 2-(4-methoxyphenylmethyl)-2H-thieno[3,2-e]-1,2-thiazine-3-carboxylate 1,1-dioxide A mixture of the product from Step A (3.91 g) and p-toluenesulfonic acid (0.2 g) in acetone (150 mL) was heated at reflux temperature for 3 h, cooled and a saturated solution of sodium bicarbonate (50 mL) was added and acetone evaporated. The aqueous mixture was extracted with ethyl acetate (2×10 mL) and the combined extracts were dried (MgSO₄) and filtered. DBU (0.3 g) was added to the filtrate and this mixture was heated at reflux temperature for 2 h, cooled and acidified by the addition of 1N HCl. The organic layer was separated, dried (MgSO₄) and evaporated to a residue which was purified by column chromatography (silica, 30% ethyl acetate/hexane) to give a viscous oil (1.80 g, 55%).

Step C: 3-Hydroxymethyl-2-(4-methoxyphenylmethyl)-2H-thieno[3,2-e]-1,2-thiazine- 3-methanol 1,1-dioxide To a solution of the product from Step B (1.80 g, 4.75 mmol) in anhydrous THF (40 mL) at ambient temperature was added DIBAL (1.0M, 11.87 mL, 11.87 mmol) and the mixture was stirred for 1 h. Additional DIBAL (1M, 15 mL,15 mmol) was added (TLC showed starting material remained) and the reaction mixture was stirred for 20 h, cooled (ice bath) and the reaction was quenched by the slow addition of 1N HCl (100 mL). THF was evaporated and the aqueous mixture was extracted with ethyl acetate (2×100 mL). The combined extracts were dried (MgSO₄), filtered and evaporated to give an oil (1.60 g) which was used in the next step without further purification.

Step D: 3-[[Bis(2-methoxyethyl)amino]methyl]-2-(4-methoxyphenylmethyl)-2H-thieno[3,2-e]-1,2-thiazine 1,1-dioxide To a solution of the product from Step C (1.60 g, 4.75 mmol) and triethylamine (1.44 g, 14.2 mmol) in anhydrous THF (100 mL) at ambient temperature was added methanesulfonic anhydride (1.24 g, 7.13 mmol). After 1 h, the reaction mixture was divided into two equal portions; to one of these portions was added bis(2-methoxyethyl)amine (6 mL). The mixture was stirred for 72 h, evaporated to dryness and the residue extracted with ethyl acetate (2×100 mL). The combined extracts were dried (MgSO₄), filtered and evaporated to a residue which was purified by column chromatography (silica, 20–30% ethyl acetate/hexane) to give an oil (0.71 g) which solidified upon standing: mp 75°–77° C.

Step E: 3-[[Bis(2-methoxyethyl)amino]methyl]-2-(4-methoxyphenylmethyl)-2H-thieno[3,2-e]-1,2-thiazine-6-sulfonamide 1,1-dioxide To a mixture of the product of Step D (1.08 g, 2.39 mmol) in anhydrous THF (40 mL) under nitrogen at −70° C. was added n-butyllithium (2.5M, 1.91 mL, 4.78 mmol) over 5 min. The mixture was stirred for 30 min and then sulfur dioxide was passed over the reaction mixture for about 5 min followed by allowing the reaction mixture to warm to ambient temperature, and finally the mixture was evaporated to dryness. A saturated aqueous solution of sodium bicarbonate (100 mL) was added to the residue; this mixture was cooled (ice bath) and hydroxylamine-O-sulfonic acid (1.00 g, 8.84 g) was added. The mixture was stirred for 18 h at ambient temperature and extracted with ethyl acetate (2×100 mL). The combined extracts were dried (MgSO₄) and evaporated to a residue which was purified by column chromatography (silica, first column 50% ethyl acetate/hexane; second column 5% methanol/methylene chloride) to give a solid which was triturated with methylene chloride/hexane, filtered and dried under vacuum at 65° C. to give a solid (0.29 g, 23%): mp 104°–105° C. (dec). Analysis. Calculated for $C_{21}H_{29}N_3O_7S_3$: C, 47.44; H, 5.50; N, 7.90. Found: C, 47.50; H, 5.49; N, 7.95.

By using the procedure described above but using instead the appropriate alkylhalide in Step A the following compounds were prepared:

1. 3-[[Bis(2-methoxyethyl)amino]methyl]-2-ethyl-2H-thieno[3,2-e]-1,2-thiazine- 6-sulfonamide 1,1-dioxide hydrochloride, mp 185°–186° C.

2. 3-[[Bis (2-methoxyethyl)amino]methyl]-2-propyl-2H-thieno[3,2-e]-1,2- 6-sulfonamide 1,1-dioxide hydrochloride, mp 201°–203° C.

3. 3-[Bis (2-methoxyethyl)amino]methyl]-2-(2-methoxyethyl)-2H-thieno[3,2-e]- 1,2-thiazine-6-sulfonamide 1,1-dioxide hydrochloride, mp 200°–202° C.

By using the procedure described above but using instead methyl iodide as the alkylhalide in Step A and 2-methoxyethyl(3-methoxypropyl)amine as the alkylamine in Step D the following compound was prepared:

4. 3-[[(2-methoxyethyl)(3-methoxypropyl)amino]methyl] -2-methyl-2H-thieno[3,2-e]- 1,2-thiazine-6-sulfonamide 1,1-dioxide hydrochloride, mp 173°–175° C.

EXAMPLE 12

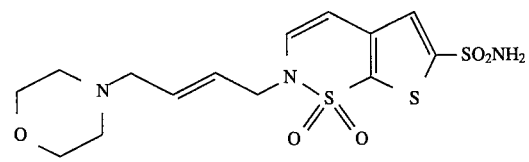

2-[4-(4-Morpholinyl)-2-butenyl]-2H-thieno[3,2-e]-1,2-thiazine-6-sulfonamide 1,1-dioxide Hydrochloride Step A: 3,4-Dihydro-4-hydroxy-N-(1,1-dimethylethyl)-2-[4-(4-morpholinyl)-2-butenyl]- 2H-thieno[3,2-e]-1,2-thiazine-6-sulfonamide 1,1-dioxide Sodium hydride (60% dispersion in mineral oil, 0.113 g, 2.82 mmol) was added to a solution of the product from Example 1, Step F (0.80 g, 2.35 mmol) in anhydrous DMF (50 mL) under nitrogen. After 20 min, the reaction mixture was cooled (ice bath), 1,4-dibromo-2-butene (0.754 g, 3.53 mmol) was added and the mixture stirred for 2 h. Morpholine (5 mL) was added and the reaction mixture was stirred at ambient temperature for 18 h. DMF was evaporated under reduced pressure and the residue was mixed with a saturated solution of sodium bicarbonate (100 mL) and extracted with ethyl acetate (2×100 mL). The combined extracts were dried (MgSO₄), filtered and evaporated to dryness. Chromatography on silica (ethyl acetate) gave the desired product as a viscous oil (0.65 g, 58%).

Step B: N-(1,1-dimethylethyl)-2-[4-(4-morpholinyl)-2-butenyl]-2H-thieno[3,2-e]- 1,2-thiazine-6-sulfonamide 1,1-dioxide To a solution of the product from Step A (0.64 g, 1.34 mmol) in anhydrous THF (30 mL) under nitrogen were added methanesulfonic anhydride (0.349 g, 2.00 mmol) and 2,6-lutidine (0.431 g, 4.02 mmol). After 30 min, an additional quantity of methanesulfonic anhydride (0.349 g, 2.00 mmol) and 2,6-lutidine (0.431 g, 4.02 mmol) was added and the reaction continued for 30 min. Evaporation of the solvent provided a residue which was dissolved in anhydrous DMF (50 mL) and DBN (1 mL) was added. This mixture was heated at reflux temperature for 1 h, cooled, poured into a saturated solution of sodium bicarbonate (100 mL) and extracted with ethyl acetate (2×100 mL). The combined extracts were dried over (MgSO₄), filtered and evaporated to a residue which was purified by column chromatography (silica, 5% methanol/methylene chloride) to give a viscous oil (0.35 g, 57%).

Step C: 2-[4-(4-Morpholinyl)-2-butenyl]-2H-thieno[3,2-e]-1,2-thiazine-6-sulfonamide 1,1-dioxide Hydrochloride A solution of the product from Step B (0.35 g) in trifluoroacetic acid (5 mL) was stirred at ambient temperature for 3 days and evaporated to dryness. The residue was mixed with a saturated solution of sodium bicarbonate (50 mL) and this mixture was extracted with ethyl acetate (2×80 mL). The combined extracts were dried (MgSO₄) and evaporated to a residue which was purified by column chromatography (silica, 6% methanol/methylene chloride to give a viscous oil (0.21 g, 68%). The free base was converted to the hydrochloride salt by treating a methanol solution (5 mL) of the free base with 2N HCl/ethanol. The residue was dissolved in methanol and evaporated under high vacuum at 65° C. to give 0.152 g of a powder (50%): mp 108°–112° C. Analysis. Calculated for $C_{12}H_{20}ClN_3O_5S_3$-0.5 H₂O: C, 37.28; H, 4.69: N, 9.31. Found: C, 37.35; H, 4.68; N, 9.25.

EXAMPLE 13

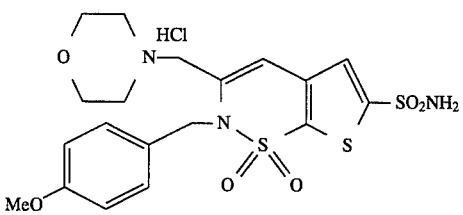

2-(4-Methoxyphenylmethyl)-3-(4-morpholinylmethyl)-2H-thieno[3,2-e]-1, 2-thiazine-6-sulfonamide 1,1-dioxide Hydrochloride Step A: 2-(4-Methoxyphenylmethyl)-3-(4-morpholinylmethyl)-2H-thieno[3,2-e]- 1,2-thiazine 1,1-dioxide Methanesulfonic anhydride (1.24 g, 7.13 mmol) was added to a solution of the product of Example 11, Step C (1.3 g, 3.86 mmol) and triethylamine (1.17 g, 11.6 mmol) in anhydrous THF (50 mL) at ambient temperature. After stirring for 1 h, morpholine (3 mL) was added and the reaction mixture was heated at reflux temperature for 1 h followed by removal of solvent. A saturated aqueous solution of sodium bicarbonate was added and the mixture was extracted with ethyl acetate (2×100 mL). The combined extracts were dried (MgSO₄) and evaporated to an oil which was purified by column chromatography (silica, 30% to 60% ethyl acetate/hexane) to give a solid (1.39 g, 88%): mp 112°–114° C.

Step B: 2-(4-Methoxyphenylmethyl)-3-(4-morpholinylmethyl)-2H-thieno[3,2-e]- 1,2-thiazine-6-sulfonamide 1,1-dioxide Hydrochloride The product of Step A (0.70 g, 1.72 mmol) was treated in a manner analogous to that described for Example 11, Step E to give, after purification by column chromatography (silica, 50% to 80% ethyl acetate/hexane), a viscous oil (0.34 g). Treatment of this oil with 2N HCl in ethanol provided the hydrochloride salt (0.342 g, 20%): mp 212°–214° C. Analysis. Calculated for $C_{19}H_{24}ClN_3O_6S_3$: C, 43.71; H, 4.63; N, 8.05. Found: C, 43.88; H, 4.73; N, 7.97.

EXAMPLE 14

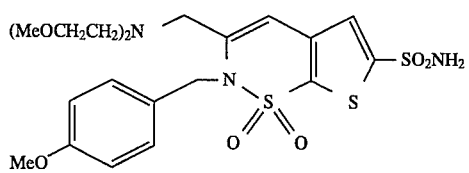

3-[[Bis(2-methoxyethyl)amino]methyl]-2-(4-methoxyphenyl)-2H-thieno[3,2-e]-1,2-thiazine-6-sulfonamide 1,1-dioxide Step A: 3-(1,3-Dioxolan-2-yl)-N-(4-methoxyphenyl)-thiophene-2-sulfonamide A solution of 3-(1,3-dioxolan-2-yl)-thiophene-2-sulfonyl chloride (11.16 g), prepared from thiophene-3-carboxaldehyde ethylene acetal as described in Example 6, Step A, in THF (100 mL) at 0° C. was combined with p-anisidine (7.87 g, 63.9 mmol) and triethylamine (4.04 g, 40 mmol). After stirring for 4 hr at ambient temperature, the mixture was evaporated to a residue which was extracted with ethyl acetate (2×150 mL). The combined extracts were dried (MgSO₄) and evaporated to a residue which was purified by column chromatography (silica, 40% ethyl acetate/hexane) to give an oil (10.21 g, 75%).

Step B: N-[(3-formyl-2-thienyl)sulfonyl]-N-(4-methoxyphenyl)-glycine Methyl Ester To a solution of the product of Step A (10.21 g, 29.9 mmol) in anhydrous THF (100 mL) and DMF (15 mL) at 0° C. was added sodium hydride (60% dispersion in mineral oil, 1.32 g, 32.9 mmol). After stirring for 30 min, methyl 2-bromoacetate (5.49 g, 35.9 mmol) was added and stirring continued at ambient temperature for 4 h. The reaction mixture was poured into a saturated solution of sodium bicarbonate (150 mL) and extracted with ethyl acetate (2×100 mL). The combined extracts was dried (MgSO₄) and evaporated to give an oil which was dissolved in acetone (150 mL) and p-toluenesulfonic acid (2.5 g) was added. This solution was stirred at ambient temperature for 2 h, heated at reflux temperature for 5 h, cooled and mixed with water (100 mL) and sodium carbonate (1.0 g). Acetone was evaporated and the aqueous was extracted with ethyl acetate (2×100 mL). The combined extracts were dried (MgSO₄) and evaporated to a residue which was purified by column chromatography (silica, 40% ethyl acetate/hexane) to give an oil (3.67 g, 33%).

Step C: Methyl 2-(4-methoxyphenyl)-2H-thieno[3,2-e]-1,2-thiazine-3-carboxylate 1,1-dioxide A mixture of the product from Step B (3.67 g, 9.95 mmol), DBU (1.0 mL) and molecular sieves (1.5 g) in ethyl acetate (100 mL) was heated at reflux temperature for 4 h, cooled to room temperature, washed with 2N HCl (50 mL) and brine (50 mL), and dried (MgSO₄). Evaporation of the solvent provided the desired ester (1.92 g) as an oil which was used without further purification.

Step D: 2-(4-Methoxyphenyl)-2H-thieno[3,2-e]-1,2-thiazine-3-methanol 1,1-dioxide A 1M solution of DIBAL in THF (45 mL, 45 mmol) was added to a solution of the product from Step C (1.92 g) in anhydrous THF (100 mL) and this mixture was stirred at ambient temperature for 18 h. After cooling (ice bath) the reaction was quenched by the addition of 1N HCl (100 mL). This mixture was extracted with ethyl acetate (2×100 mL) and the combined extracts were dried (MgSO₄) and evaporated to a residue which was purified by column chromatography (silica, 50% ethyl acetate/hexane) to give a viscous oil (1.19 g, 41%).

Step E: 3-[[Bis(2-methoxyethyl)amino]methyl]-2-(4-methoxyphenyl)-2H-thieno[3,2-e]-1,2-thiazine 1,1-dioxide To a solution of the product of Step D (1.19 g, 3.68 mmol) and triethylamine (1.24 g, 12.3 mmol) in anhydrous THF (50 mL) was added methanesulfonic anhydride (1.07 g, 6.13 mmol). After 30 min, bis(2-methoxyethyl)amine (3 mL) was added and stirring continued for 18 h at ambient temperature. The reaction mixture was heated at reflux temperature for 1 h, cooled, poured into a saturated solution of sodium bicarbonate (100 mL) and this mixture was extracted with ethyl acetate (2×100 mL). The combined extracts were dried (MgSO$_4$) and evaporated to a residue which was purified by column chromatography (silica, 40% ethyl acetate/hexane) to give a viscous oil (1.16 g, 72%).

Step F: 3-[[Bis(2-methoxyethyl)amino]methyl]-2-(4-methoxyphenyl)-2H-thieno[3,2-e]-1,2-thiazine-6-sulfonamide 1,1-dioxide The product of Step E (1.12 g, 2.56 mmol) was treated in a manner analogous to that described for Example 11, Step E to give, after purification by column chromatography (silica, 60% to 80% ethyl acetate/hexane) a colorless glass (0.41 g, 31%): mp 48°–51° C. Analysis. Calculated for $C_{20}H_{27}N_3O_7S_3$: C, 46.40; H, 5.26; N, 8.11. Found: C, 46.34; H, 5.30; N, 8.04.

By following the procedure described above but replacing para-anisidine with 4-(4-morpholinyl)-aniline in Step A, and further replacing bis(2-methoxyethyl)amine with morpholine in Step E the following compound was prepared:

1. 3-(4-Morpholinylmethyl)-2-[4-(4-morpholinyl)phenyl] -2H-thieno[3,2-e]- 1,2-thiazine- 6-sulfonamide 1,1-dioxide hydrochloride, mp 230°–235° C.

EXAMPLE 15

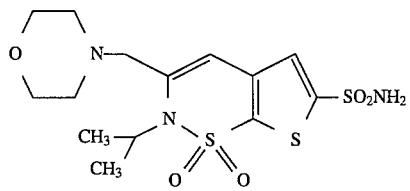

2-(1-Methylethyl)-3-(4-morpholinylmethyl)- 2H-thieno[3,2-e]-1,2-thiazine- 6-sulfonamide 1,1-dioxide Step A: 3-(1,3-Dioxolan-2-yl)-N-(1-methylethyl)-2-thiophenesulfonamide By following the procedure described in Example 14, Step A, but using isopropylamine in place of para-anisidine the desired compound was obtained, following column chromatography (silica, 30% ethyl acetate/hexane), as a colorless oil (62%).

Step B: N-[[3-(1,3-Dioxolan-2-yl)-2-thienyl]sulfonyl]-N-(1-methylethyl)-glycine Ethyl Ester To a solution of the product from Step A (25.0 g, 90.3 mmol) in anhydrous DMF (350 mL) at 0° C. was added a 1M solution of potassium t-butyloxide in t-butanol (99.3 mL, 99.3 mmol) followed by ethyl bromoacetate (12.0 mL, 18.1 g, 108.4 mmol). The solution, which immediately turned cloudy, was maintained at 0° C. for 18 h. The reaction mixture was poured into a saturated aqueous solution of sodium bicarbonate (600 mL) and this mixture was extracted with ether (3×300 mL). The combined extracts were dried (MgSO$_4$) and evaporated to give an viscous oil (36.25 g) which was used in the next reaction without further purification.

Step C: Ethyl 2-(1-methylethyl)-2H-thieno[3,2-e]-1,2-thiazine-3-carboxylate 1,1-dioxide A solution of the product from Step B (36.25 g) and p-toluenesulfonic acid hydrate (2.0 g) in acetone (300 mL) was heated at reflux temperature for 6 h, cooled and a saturated aqueous solution of sodium bicarbonate (100 mL) was added. Acetone was evaporated and the aqueous mixture was extracted with ether (2×100 mL). The combined extracts were dried (MgSO$_4$) and evaporated to give a dark brown oil which was dissolved in ethyl acetate (200 mL). DBU (2 mL) was added to this solution and after 1 h the reaction mixture was washed with 2N HCl and brine, dried (MgSO$_4$), and evaporated to give a solid which was recrystallized from 25% ethyl acetate/hexane to give 9.95 g of product. The mother liquor was chromatographed (silica, 25% ethyl acetate/hexane) to give an additional 3.57 g of product (total 13.52 g, 50%): mp 97°–99° C.

Step D: 2-(1-Methylethyl)-2H-thieno[3,2-e]-1,2-thiazine-3-methanol 1,1-dioxide

To a solution of the product from Step C (13.80 g, 45.85 mmol) in anhydrous THF (50 mL) at ambient temperature was added DIBAL (1.0M, 145 mL, 145 mmol) under nitrogen. After stirring for 5 h, the reaction mixture was evaporated to dryness and mixed with ethyl acetate (200 mL), water was slowly added over 20 min. The mixture was acidified with 2N HCl and extracted with ethyl acetate (2×200 mL). The combined extracts were dried (MgSO$_4$) and evaporated to a residue which was purified by column chromatography (silica, 40% ethyl acetate/hexane) to give a viscous oil. Crystallization from ethyl acetate/hexane gave the desired product (7.51 g, 63%): mp 67°–69° C.

Step E: 3-Hydroxymethyl-2-(1-methylethyl)-2H-thieno[3,2-e]-1,2-thiazine-6-sulfonamide 1,1-dioxide To a solution of the product from Step D (3.25 g, 12.5 mmol) in anhydrous THF (60 mL) under nitrogen at −70° C. was added n-butyllithium (2.5M, 12.5 mL, 31.4 mmol) over 5 min. The suspension was stirred for 1 h before a stream of sulfur dioxide was passed over the surface of the reaction mixture for 5 min. The mixture was warmed to ambient temperature and evaporated to give a residue which was combined with water (100 mL); this mixture was cooled (ice bath) and hydroxylamine-O-sulfonic acid (4.24 g, 37.5 mmol) and NaOAc (8.5 g, 62.5 mmol) were added. The reaction mixture was stirred at ambient temperature for 18 h and extracted with ethyl acetate (2×200 mL). The combined extracts were dried (MgSO$_4$), filtered, and evaporated to a residue which was purified by column chromatography (silica, 50% ethyl acetate/hexane) to give a viscous oil (4.20 g, 98%).

Step F: 2-(1-Methylethyl)-3-(4-morpholinylmethyl)-2H-thieno[3,2-e]-1,2-thiazine- 6-sulfonamide 1,1-dioxide To a solution of the product from Step E (2.16 g, 6.39 mmol) and triethylamine (2.58 g, 25.6 mmol) in anhydrous THF (100 mL) at 0° C. was added p-toluenesulfonyl chloride (2.44 g, 12.8 mmol) with stirring. After 1 h the reaction mixture was warmed to ambient temperature and maintained at this temperature for 4 h. Half of the reaction mixture was removed, cooled on an ice bath and morpholine (3 mL) was added with stirring. The reaction mixture was stirred for 18 h and evaporated to a residue which was mixed with ethyl acetate (200 mL); this solution was washed with a saturated solution of sodium bicarbonate (100 mL), dried (MgSO$_4$), filtered and evaporated to a residue which was purified by colunmn chromatography (silica, 4% methanol/methylene chloride) to give a viscous oil which crystalized from methylene chloride/hexane to afford a yellowish solid (0.41 g, 32%): mp 196°–198° C. Analysis: Calculated for $C_{14}H_{21}N_3O_5S_3$: C, 41.26; H, 5.19 N, 10.31. Found: C, 41.35; H, 5.10; N, 10.28.

EXAMPLE 16

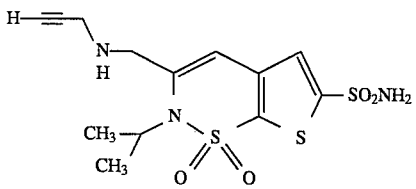

2-(1-Methylethyl)-3-[(2-propynylamino)methyl]-2H-thieno[3,2-e]-1,2-thiazine- 6-sulfonamide 1,1-dioxide To a solution of the product from Example 15, Step E (1.40 g, 4.14 mmol) and triethylamine (1.26 g, 12.4 mmol) in anhydrous THF (80 mL) at 0° C. was added p-toluenesulfonyl chloride (1.18 g, 6.21 mmol) and the mixture was maintained at this temperature for 20 h. Propargylamine (3 mL) was added to the reaction mixture which was stirred for an additional 18 h. The reaction mixture was evaporated to a residue which was mixed with 2N HCl (60 mL) and this mixture was extracted with ethyl acetate (2×50 mL). The aqueous layer was separated and adjusted to pH 7.5 by the addition of a saturated aqueous solution of sodium bicarbonate (100 mL) followed by extraction with ethyl acetate (2×60 mL). The combined extracts were dried ($MgSO_4$), filtered, and evaporated to a residue which was purified by column chromatography (silica, 50% to 75% ethyl acetate/hexane) to give an oil which crystallized from methylene chloride/hexane to provided an off-white solid (0.61 g, 39%): mp 133°–135° C. Analysis: Calculated for $C_{13}H_{17}N_3O_4S_3$: C, 41.58; H, 4.60; N, 11.11. Found: C, 41.42; H, 4.60;0N, 11.11.

EXAMPLE 17

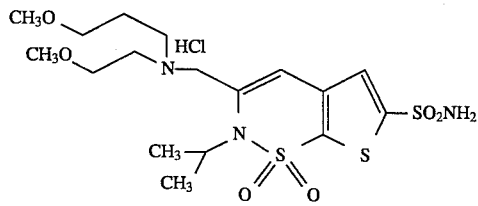

2-(1-Methylethyl)-3-[[(2-methoxyethyl)(3-methoxypropyl)amino]methyl]-2H-thieno[3,2-e]-1,2-thiazine-6-sulfonamide 1,1-dioxide Hydrochloride By following the procedure described in Example 16 but using (2-methoxyethyl)(3-methoxypropyl)amine instead of propargylamine, 2-(1-methylethyl)-3-[[(2-methoxyethyl)(3-methoxypropyl)amino]methyl]-2H-thieno[3,2-e]-1,2-thiazine-6-sulfonamide 1,1-dioxide was obtained as an oil following purification by column chromatography (silica, column one: 3% to 5% methanol/methylene chloride; column two: gradient, 60% ethyl acetate/hexane to ethyl acetate). Treatment of this oil with ethanolic hydrogen chloride provided the title compound as a white solid (26%): mp 56°–60° C. Analysis: Calculated for $C_{13}H_{17}N_3O_4S_3$·0.5$H_2O$: C, 39.79; H, 6.09; N, 8.19. Found: C, 39.50; H, 6.14; N, 8.12.

EXAMPLE 18

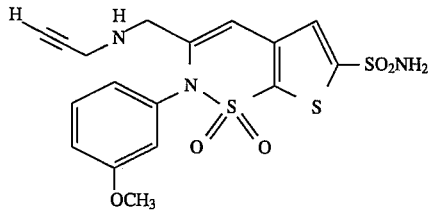

2-(3-Methoxyphenyl)-3-[(2-propynylamino)methyl]-2H-thieno[3,2-e]-1,2-thiazine- 6-sulfonamide 1,1-dioxide Step A: 3-(1,3-Dioxolan-2-yl)-N-(3-methoxyphenyl)-2-thiophenesulfonamide By following the procedure described in Example 14, Step A, but using meta-anisidine in place of para-anisidine the desired compound was obtained, following column chromatography (silica, 30% ethyl acetate/hexane), as a solid (62%): mp 112°–114° C.

Step B: N-[[3-(1,3-Dioxolan-2-yl)-2-thienyl]sulfonyl]-N-(3-methoxyphenyl)glycine Ethyl Ester A solution of the product from Step A (10.0 g, 29.3 mmol) in anhydrous DMF (100 mL) was treated in a manner essentially analogous to that described in Example 15, Step B to give a viscous oil (12.52 g) which was used in the next step without further purification.

Step C: Ethyl 2-(3-methoxyphenyl)-2H-thieno[3,2-e]-1,2-thiazine-3-carboxylate 1,1-dioxide A solution of the product from Step B (33.78 g) and p-toluenesulfonic acid hydrate (3.0 g) in acetone (300 mL) were treated in a manner essentially analogous to that described in Example 15, Step C to give a total of 13.41 g (46%) of the desired product: mp 107°–109° C.

Step D: 2-(3-Methoxyphenyl)-2H-thieno[3,2-e]-1,2-thiazine-3-methanol 1,1-dioxide A solution of the product of Step C (5.64 g, 15.45 mmol) in anhydrous THF (150 mL) was treated with DIBAL (66 mmol) in a manner essentially analogous to that described in Example 15, Step D to provide the desired product as a white solid (3.62 g, 73%): mp 141°–143° C.

Step E: 3-Hydroxymethyl-2-(3-methoxyphenyl)-2H-thieno[3,2-e]-1,2-thiazine-6-sulfonamide 1,1-dioxide A solution of the product from Step D (2.0 g, 6.19 mmol) was treated sequentially with n-butyllithium, sulfur dioxide and hydroxylamine-O-sulfonic acid in a manner essentially analogus to that described in Example 15, Step E to give an orange solid (1.78 g, 72%): mp 180°–182° C.

Step F: 2-(3-Methoxyphenyl)-3-[(2-propynylamino)methyl]-2H-thieno[3,2-e]-1,2-thiazine- 6-sulfonamide 1,1-dioxide To a solution of the product from Step E (0.766 g, 1.89 mmol) and triethylamine (0.57 g, 5.67 mmol) in anhydrous THF (50 mL) at 0° C. was added p-toluenesulfonyl chloride (0.54 g, 2.84 mmol). The reaction mixture was stirred for 18 h maintaining a temperature below 15° C. Propargylamine (2 mL) was added and this mixture was stirred for 18 h, evaporation of the solvent provided a residue which was acidified to pH 1 with 2N HCl and extracted with ethyl acetate (200 mL). The aqueous layer was separated, adjusted to pH 7.5 with a saturated aqueous solution of sodium bicarbonate (50 mL) and this mixture was extracted with ethyl acetate (2×80 mL). The combined extracts were dried (MgSO$_4$) and evaporated to give a solid which was recrystallized from methylene chloride/hexane to give a cream colored solid (0.26 g, 31%): mp 174°–176° C. Analysis: Calculated for C$_{17}$H$_{17}$N$_3$O$_5$S$_3$- 0.5H$_2$O: C, 45.52; H, 4.05; N, 9.36. Found: C, 45.53; H, 3.85; N, 9.12.

By following the procedure described above but replacing propargylamine with morpholine in step F the following compound was prepared:

1. 2-(3-Methoxyphenyl)-3-(4-morpholinylmethyl)-2H-thieno[3,2-e]-1,2-thiazine- 6-sulfonamide 1,1-dioxide hydrochloride mp 170°–174° C.

By following the procedure described above but replacing meta-anisidine with the appropriate substituted aniline in Step A the following compounds were prepared:

2. 2-(3,4-Dimethoxyphenyl)-3-[(2-propynylamino)methyl]-2H-thieno[3,2-e]-1,2-thiazine- 6-sulfonamide 1,1-dioxide hydrochloride, mp 154°–156° C.

3. 2-(3,5-Dimethoxyphenyl)-3-[(2-propynylamino)methyl]-2H-thieno[3,2-e]-1,2-thiazine- 6-sulfonamide 1,1-dioxide hydrochloride, mp 236°–237° C.

By following the procedure described above using 3,5-dimethoxyaniline in Step A and replacing propargylamine with-morpholine in Step F the following compound was prepared:

4. 2-(3,5-Dimethoxyphenyl)-3-(4-morpholinylmethyl)-2H-thieno[3,2-e]-1,2-thiazine- 6-sulfonamide 1,1-dioxide hydrochloride, mp 236°–237° C.

EXAMPLE 19

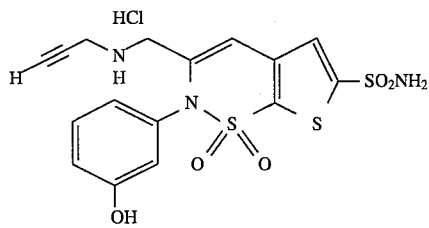

2-(3-Hydroxyphenyl)-3-[(2-propynylamino)methyl]-2H-thieno[3,2-e]-1,2-thiazine- 6-sulfonamide 1,1-dioxide Hydrochloride Step A: 3-Chloromethyl-N-(1,1-dimethylethyl)-2-(3-methoxyphenyl)-2H-thieno[3,2-e]-1,2-thiazine-6-sulfonamide 1,1-dioxide To a solution of the product from Example 18, Step D (4.81 g, 14.89 mmol) in anhydrous THF (80 mL) under nitrogen at −70° C. was added n-butyllithium (2.5M, 14.89 mL, 37.22 mmol) over 5 min. After stirring for 1 h, a stream of sulfur dioxide was passed over the surface of the reaction mixture for about 5 min. The mixture was warmed to ambient temperature and evaporated to a residue which was mixed with methylene chloride (250 mL). This suspension was cooled on an ice bath and N-chlorosuccinimide (6.96 g, 52.1 mmol) was added. The reaction mixture was stirred at ambient temperature for 2 h and t-butylamine (15 mL, 143 mmol) was added; the mixture was evaporated to dryness after 16 h. The residue was mixed with a saturated aqueous solution of sodium bicarbonate (200 mL) and extracted with ethyl acetate (2×200 mL). The combined extracts were dried (MgSO$_4$) and evaporated to give a residue which was purified by column chromatography (silica, 40% ethyl acetate/hexane) to give an oil (4.41 g, 62%):

Step B: 2-(3-Hydroxyphenyl)-3-[(2-propynylamino)methyl] -2H-thieno[3,2-e]-1,2-thiazine- 6-sulfonamide 1,1-dioxide Hydrochloride To a solution of the product from Step A (1.00 g, 2.10 mmol) in anhydrous DMF (20 mL) was added propargylamine (1.77 g, 32.1 mmol). The mixture was stirred at ambient temperature for 30 min, heated at 80° C. for 2 h and evaporated to dryness. The residue was mixed with a saturated aqueous solution of sodium bicarbonate (100 mL) and extracted with ethyl acetate (2×100 mL). The combined extracts were dried (MgSO$_4$) and evaporated to a residue which was purified by column chromatography (silica, 50 % ethyl acetate/hexane) to give a viscous oil (0.53 g, 51%). The oil was dissolved in methylene chloride (50 mL), cooled to 0° C., and a 1M solution of BBr$_3$ in methylene chloride (5.25 mL) was added over 3 min. The mixture was allowed to warmed to ambient temperature and maintained at this temperature for 2 h. The reaction mixture was poured into a saturated aqueous solution of sodium bicarbonate (100 mL) and extracted with ethyl acetate (2×100 mL). The combined extracts were dried (MgSO$_4$) and evaporated to an oil which was purified by column chromatography (silica, 70% ethyl acetate/hexane) to give an oil which was dissolved in ethyl acetate and treated with HCl/EtOH. After evaporating the solvent, the salt was recrystallized from ethanol/methylene chloride to give a yellowish solid (0.278 g, 57%): mp 195°–198°° C. Analysis. Calculated. for C$_{16}$H$_{16}$ClN$_3$O$_5$S$_3$: C, 41.60; H, 3.49; N, 9.09. Found: C, 41.69; H, 3.51;N, 9.04.

By following the procedure described above but replacing propargylamine with morpholine in Step B the following compound was prepared:

1. 2-(3-Hydroxyphenyl)-3-(4-morpholinylmethyl)-2H-thieno[3,2-e]-1,2-thiazine- 6-sulfonamide 1,1-dioxide mp 220°–222° C.

EXAMPLE 20

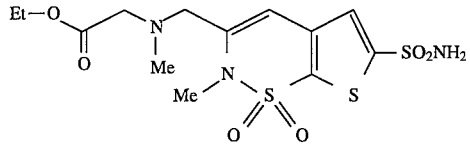

N-[[6-(Aminosulfonyl)-2-methyl-2H-thieno[3,2-e]-1,2-thiazin-3-yl]methyl]-N-methyl-glycine Ethyl Ester S$^1$, S$^1$-dioxide Step A: 3-Hydroxymethyl-2-methyl-2H-thieno[3,2-e]-1,2-thiazine-6-sulfonamide 1,1-dioxide To a solution of the product from Example 6, Step C (3.20 g, 13.85 mmol) in anhydrous THF (50 mL) under nitrogen at −70° C. was added n-butyllithium (2.5M, 12.74 mL, 31.86 mmol) via syringe over 3 min. The suspension was stirred for 10 min before a stream of sulfur dioxide was passed over the surface of the reaction mixture for about 5 min. The reaction mixture was warmed to ambient temperature and solvent was evaporated to give a residue which was mixed with ice-water (200 mL). Hydroxylamine-O-sulfonic acid (4.70 g, 41.6 mmol) and sodium acetate (7.53 g, 55.4 mmol) were added and this aqueous mixture was stirred at ambient temperature for 16 h followed by extraction with ethyl acetate (2×200 mL). The combined extracts were dried (MgSO$_4$) and evaporated to a solid which was recrystallized from ethyl acetate/hexane (3.55 g, 83%): mp 144°–146° C.

Step B: N-[[6-(Aminosulfonyl)-2-methyl-2H-thieno[3,2-e]-1,2-thiazin-3-yl]methyl]-N-methyl-glycine Ethyl Ester S$^1$, S$^1$-dioxide To a solution of the product from Step A (1.00 g, 3.23 mmol) and triethylamine (0.652 g, 6.45 mmol) in anhydrous THF (30 mL) at ambient temperature was added methanesulfonic anhydride (0.844 g, 4.85 mmol). After 30 min sacosine ethyl ester (freshly prepared from 3.00 g of the hydrochloride salt, 7.9 mmol) was added and the mixture stirred for 3 h, evaporated to dryness, mixed with a saturated aqueous solution of sodium bicarbonate (100 mL) and extracted with ethyl acetate (2×100 mL). The combined extracts were dried (MgSO₄) and evaporated to a residue which was purified by column chromatography (silica, 50% ethyl acetate/hexane) to give an oil (0.94 g, 71%). The oil was dissolved in ethyl acetate (10 mL) and treated with 2N ethanolic HCl. The volatiles were evaporated and the residue was recrystallized from a water/methanol mixture to give a white solid which analyzed as the free base (0.396 g, 30%): mp 106°–108° C. Analysis. Calculated for $C_{13}H_{19}N_3O_6S_3$: C, 38.13; H, 4.68; N, 10.26. Found: C, 38.16; H, 4.63; N, 10.31.

EXAMPLE 21

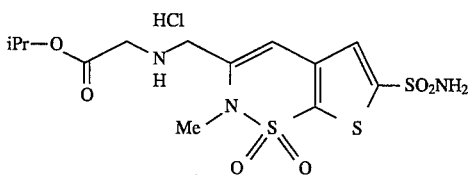

N-[[6-(Aminosulfonyl)-2-methyl-2H-thieno[3,2-e]-1,2-thiazin-3-yl]methyl]-glycine 2-methylethyl Ester $S^1$, $S^1$-dioxide Hydrochloride To a solution of the product from Example 20, Step A (1.00 g, 3.23 mmol) and triethylamine (0.65 g, 6.45 mmol) in anhydrous THF (30 mL) at ambient temperature was added methanesulfonic anhydride (0.843 g, 4.84 mmol). After 5 min glycine isopropyl ester (1.20 g, 10.3 mmol) was added and the mixture stirred for 2 h, evaporated to dryness, mixed with a saturated aqueous solution of sodium bicarbonate (100 mL) and extracted with ethyl acetate (2×100 mL). The combined extracts was washed with 2N HCl (2×50 mL). The aqueous was separated, adjusted to about pH 8 and extracted with ethyl acetate (2×80 mL). The combined extracts were dried (MgSO⁴) and evaporated to give an oil (0.51 g) which was dissolved in ethyl acetate (10 mL) and treated with 2N ethanolic HCl. Evaporation of the solvent provided a residue which was recrystallized from isopropanol to give a white solid (0.37 g, 26%): mp 202°–205° C. Analysis calculated for $C_{13}H_{19}N_3O_6S_3$-HCl-H₂O: C, 33.65; H, 4.78; N, 9.06. Found: C, 33.69; H, 4.76; N, 8.85.

EXAMPLE 22

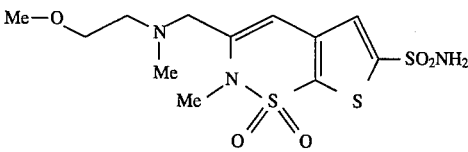

3-[[(2-methoxyethyl)methylamino]methyl]-2-methyl-2H-thieno[3,2-e]-1, 2-thiazine-6-sulfonamide 1,1-dioxide To a stirred solution of the product from Example 20, Step A (0.80 g, 2.58 mmol) and triethylamine (0.52 g, 5.16 mmol) in anhydrous THF (30 mL) was added methanesulfonic anhydride (0.674 g, 3.87 mmol) under nitrogen. After 30 min the reaction mixture was cooled on an ice bath and (2-methoxyethyl)methylamine (1 mL) was added, warmed to ambient temperature and maintained at this temperature for 2 h followed by heating at reflux temperature for 10 min and evaporated to dryness. The residue was mixed with 2N HCl (50 mL) and extracted with ethyl acetate (100 mL) to remove unreacted starting material. The aqueous layer was separated, mixed with a saturated aqueous solution of sodium bicarbonate (150 mL) and extracted with ethyl acetate (2×100 mL). The combined extracts were dried (MgSO₄) and evaporated to dryness. Column chromatography on silica (4% methanol/methylene chloride) gave a viscous oil which was recrystallized from ethyl acetate/chlorobutane to give a yellowish solid (0.635 g, 66%): mp 127°–129° C. Analysis. Calculated for $C_{12}H_{19}N_3O_5S_3$: C, 37.78; H, 5.02; N, 11.01. Found: C, 37.77; H, 4.99; N, 10.98.

EXAMPLE 23

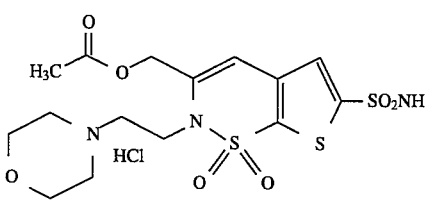

3-[(Acetyloxy)methyl]-2-[2-(4-morpholinyl)ethyl]-2H-thieno[3,2-e]-1,2-thiazine- 6-sulfonamide 1,1-dioxide Hydrochloride Step A: 3-(2-Dioxolanyl)-N-[2-(4-morpholinyl)]ethyl]-2-thiophenesulfonamide To a solution of thiophene-3-carboxaldehyde ethylene acetal (10.0 g, 64.1 mmol) in anhydrous THF (200 mL) at −70° C. was added n-butyllithium (2.5M, 28.2 mL, 70.5 mmol) over 10 min with stirring under nitrogen. The solution was stirred at −50° C. for 10 min and −70° C. for 1 h. Sulfur dioxide gas was passed over the reaction mixture for about 10 min followed by warming to room temperature and then evaporating to dryness. The residue was mixed with methylene chloride (200 mL) and N-chlorosuccinimide (11.13 g, 83.3 mmol) was added to the suspension. After 2 h, the mixture was filtered through a celite pad. The filtrate was cooled (ice bath) and 2-(4-morpholinyl)ethylamine (11.6 g, 89.1 mmol) and a saturated aqueous solution of sodium bicarbonate (100 mL) were added. The mixture was stirred at room temperature for 2 h and the organic layer was separated, washed with brine, dried over magnesium sulfate and evaporated to give a crude oil. Chromatography on silica (50% ethyl acetate/hexane) gave a viscous oil (20.15 g, 90%).

Step B: N-[(3-Formyl-2-thienyl)sulfonyl]-N-[2-(4-morpholinyl)ethyl]-glycine Methyl Ester To a solution of the product from Step A (6.34 g, 18.2 mmol) in anhydrous DMF (40 mL) at ambient temperature was added sodium hydride (60% dispersion in mineral oil, 0.80 g, 20.0 mmol) with stirring under nitrogen. After 20 min, methyl 2-bromoacetate (3.62 g, 23.7 mmol) was added and the resulting mixture was stirred at ambient temperature for 40 min; a 2N HCl aqueous solution (50 mL) was added and the mixture was stirred overnight. The reaction mixture was poured into a saturated aqueous solution of sodium bicarbonate (150 mL) and extracted with ethyl acetate (2×100 mL). The combined extracts were dried over magnesium sulfate and evaporated to give a crude oil (6.53 g, 95%).

Step C: 2-[2-(4-Morpholinyl)ethyl]-2H-thieno[3,2-e]-1,2-thiazine-2-carboxylic Acid Methyl Ester 1,1-dioxide

43

A mixture of the product from Step B (6.53 g, 1.74 mmol), DBU (0.8 mL) and molecular sieves (4.0 g) in ethyl acetate (100 mL) was stirred at ambient temperature overnight and mixed with a saturated aqueous solution of sodium bicarbonate (80 mL). The organic layer was separated, washed with brine (100 mL), dried over magnesium sulfate and evaporated to give a crude oil. Chromatography on silica (66% ethyl acetate/hexane) gave a white solid (4.15 g, 67%): mp 103°–106° C.

Step D: 2-[2-(4-Morpholinyl)ethyl]-2H-thieno[3,2-e]-1,2-thiazine-3-methanol 1,1-dioxide To a stirred solution of the product from Step C (3.80 g, 10.6 mmol) in anhydrous THF (50 mL) at 0° C. was added a 1M solution of diisobutylaluminium hydride in THF (31.8 mL, 31.8 mmol). The mixture was stirred for 1 h and then warmed to ambient temperature and stirred for an additional 30 min, cooled (ice bath) and the reaction was quenched by the addition of a aqueous solution of potassium sodium tartrate (15.0 g in 50 mL of water). This mixture was stirred at ambient temperature for 1 h and extracted with ethyl acetate (22×100 mL). The combined extracts were dried over magnesium sulfate and evaporated to give a solid (3.26 g, 93%): mp 119°–121° C.

Step E: 3-Hydroxymethyl-2-[2-(4-morpholinyl)ethyl]-2H-thieno[3,2-e]-1,2-thiazine- 6-sulfonamide 1,1-dioxide To a mixture of the product from Step D (3.25 g, 9.85 mmol) in anhydrous THF (40 mL) under nitrogen at −70° C. was added n-butyllithium (2.5M in hexanes, 9.06 mL, 22.7 mmol). The mixture was stirred for 7 min before sulfur dioxide gas was passed over the solution for about 5 min. The resulting mixture was warmed to ambient temperature and evaporated to a residue which was mixed with ice-water (150 mL), hydroxylamine-O-sulfonic acid (3.34 g, 29.6 mmol) and sodium acetate (6.20 g, 45.6 g) and stirred for 4 h at ambient temperature. The reaction mixture was extracted with ethyl acetate (2×100 mL) and the combined extracts were dried over magnesium sulfate and evaporated to a residue which was purified by column chromatography (silica, 5% to 10% methanol/methylene chloride) to give a glass (3.10 g, 77%).

Step F: 3-(Acetyloxymethyl)-2-[2-(4-morpholinyl)ethyl]-2H-thieno[3,2-e]-1,2-thiazine- 6-sulfonamide 1,1-dioxide Hydrochloride The product from Step E (0.80 g, 1.96 mmol) was mixed with acetic acid (20 mL) and acetic anhydride (0.45 g, 4.41 mmol), stirred at ambient temperature for 2 h, heated at reflux temperature for 2 h and evaporated to give an oil. A solution of the oil in ethyl acetate (100 mL) was washed with a saturated aqueous solution of sodium bicarbonate (100 mL), dried over magnesium sulfate and evaporated to give a viscous oil. Purification of this oil by column chromatography (silica, 50% ethyl acetate/hexane to ethyl acetate gradient) gave a foamy solid (0.61 g) which was dissolved in ethyl acetate and treated with ethanolic HCl. Evaporation and recrystallization from acetonitrile/isopropanol gave a colorless solid (0.57 g, 55%): mp 135°–140° C. Analysis. Calculated for $C_{15}H_{21}N_3O_7S_3 \cdot HCl \cdot 0.8$ i-PrOH: C, 38.90; H, 5.51; N, 7.82. Found: C, 38.85; H, 5.48; N, 7.72.

By following the procedure described above but using trimethylacetyl chloride and trifluoroacetic acid in Step F the following compound was prepared.

1. 3-[(2,2-Dimethyl-1-oxopropoxy)methyl]-2-[2-(4-morpholinyl)ethyl]-2H-thieno[3,2-e]-1,2-thiazine-6-sulfonamide 1,1-dioxide hydrochloride, mp 156°–159° C.

EXAMPLE 24

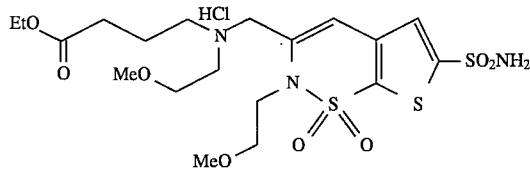

Ethyl 4-[(2-methoxyethyl)[[6-(aminosulfonyl)-2-(2-methoxyethyl)-2H-thieno[3,2-e]- 1,2-thiazin-2-yl]methyl]amino]butanoate $S^1$, $S^1$-dioxide Hydrochloride Step A: 4-[(2-Methoxyethyl)amino]butyronitrile To a stirred mixture of 2-methoxyethylamine (20.3 g, 270 mmol) and potassium carbonate (11.2 g, 81.1 mmol) was added 4-bromobutyronitrile (10.0 g, 67.6 mmol) over 20 minutes. This mixture was heated at reflux temperature for 1 h, mixed with ethyl acetate (100 mL) and filtered. The filtrate was concentrated and distilled at 109°–115° C. (0.1 mmHg) to give a clear liquid (9.78 g, quantitative).

Step B: 4-[(2-methoxyethyl)[[6-(aminosulfonyl)-2-(2-methoxyethyl)-2H-thieno[3,2-e]-1,2-thiazin-2-yl]methyl]amino]butyronitrile $S^1$, $S^1$-dioxide To a solution of 3-hydroxymethyl-2-(2-methoxyethyl)-2H-thieno[3,2-e]-1,2-thiazine- 6-sulfonamide 1,1-dioxide (prepared as described in Example 11.3) (2.54 g, 7.18 mmol) and triethylamine (1.45 g, 14.4 mmol) in anhydrous THF (30 mL) at 0° C. was added methanesulfonic anhydride (1.88 g, 10.8 mmol) with stirring, when the addition was complete, the ice bath was removed and the mixture was allowed to warm to ambient temperature and stirred for 30 min. The mixture was again cooled (ice bath) and the product of Step A (2 mL) was added and the mixture stirred for 2 h followed by heating at 50° C. for 5 min and evaporation to dryness. This crude product was mixed with a saturated aqueous solution of sodium bicarbonate (100 mL) and extracted with ethyl acetate (2×100 mL). The combined extracts were dried (MgSO$_4$) and evaporated to a residue which was purified by column chromatography (silica, 70% ethyl acetate/hexane) to give two compounds; 1.16 g and 0.57 g, respectively. NMR showed the first compound to be unreacted mesylate intermediate, which was again treated with 4-[(2-methoxyethyl)amino]butyronitrile (2 mL) but at refluxing temperature for 2 h to effect conversion to the desired compound (total 1.42 g, 41%).

Step C: Ethyl 4-[(2-methoxyethyl)[[6-(aminosulfonyl)-2-(2-methoxyethyl)-2H-thieno[3,2-e]-1,2-thiazin-2-yl]methyl]amino]butanoate $S^1$, $S^1$-dioxide hydrochloride A stream of hydrogen chloride gas was passed through (10 min) a solution of the product from Step B (1.40 g, 2.93 mmol) in ethanol (150 mL) at 0° C. (exothermic reaction). After stirring for 2 h, additional hydrogen chloride was passed through the reaction mixture (10 min) which was then maintained at 5° C. for 72 h. Water (50 mL) was added to the mixture which was stirred for 2 h and then evaporated to a residue which was mixed with a saturated aqueous solution of sodium bicarbonate (100 mL) and extracted with ethyl acetate (2×80 mL). The combined extracts were dried (MgSO$_4$) and evaporated to a residue which was purified by column chromatography (silica, 80% ethyl acetate/hexane) to give an oil (0.76 g, 49%). The oil was dissolved in methylene chloride and treated with 2N HCl/EtOH to give the hydrochloride salt as an amorphous solid (0.72 g, 44%): mp 67°–72° C.; Analysis. Calculated for $C_{19}H_{31}N_3O_8S_3$-

HCl: C, 40.59; H, 5.74; N, 7.48. Found: C, 40.48; H, 5.78; N, 7.41;

EXAMPLE 25

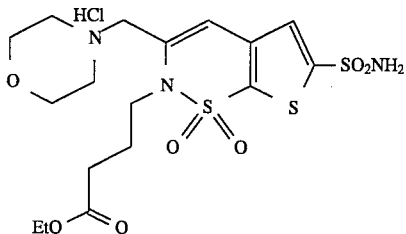

6-(Aminosulfonyl)-3-(4-morpholinylmethyl)-
2H-thieno[3,2-e]-1,2-thiazine- 2-butanoic Acid 1,1-dioxide
Ethyl Ester Step A: 3-(1,3-Dioxolan-2-yl)-N-(4-hydroxybutyl)-2-thiophenesulfonamide A solution of 3-(1,3-dioxolan-2-yl)-thiophene-2-sulfonyl chloride, prepared from thiophene-3-carboxaldehyde ethylene acetal (20.0 g, 128 mmol) as described in Example 6, Step A, was combined with 4-amino-1-butanol (17.1 g, 192 mmol) and triethylamine (15 g, 148 mmol). The reaction was stirred for 1 h, a saturated aqueous solution of sodium bicarbonate (200 mL) was added and this mixture was stirred for 1 h. The organic layer was separated, dried (MgSO$_4$), and evaporated to a residue which was purified by column chromatography (silica, 50% ethyl acetate/hexane to ethyl acetate, gradient) to give an oil (26.45 g, 62%).

Step B: 2-(4-Hydroxybutyl)-2H-thieno[3,2-e]-1,2-thiazine-3-carboxylic Acid 1,1-dioxide Methyl Ester To a solution of the product from Step A (10.6 g, 34.5 mmol) in anhydrous DMF (200 mL) at 0° C. was added NaH (60% dispersion in mineral oil, 1.45 g, 36.3 mmol). After 30 min methyl bromoacetate (3.92 mL, 6.33 g, 41.4 mmol) was added and the solution was stirred for 40 min. A 2N HCl solution (100 mL) was added and this mixture was stirred at ambient temperature for 1 h, poured into ice-water (300 mL) and extracted with ethyl acetate (2×300 mL). The combined extracts were dried (MgSO$_4$), and evaporated to give a viscous oil (13.42 g). The crude oil was dissolved in ethyl acetate (200 mL), mixed with DBU (1 mL) and molecular sieves (8.0 g) and stirred for 2 h followed by quenching the reaction by the addition of 2N HCl (100 mL). The organic layer was separated, dried (MgSO$_4$), and evaporated to a residue which was purified by column chromatography (silica, 70% ethyl acetate/hexane) to give a viscous oil (7.44 g, 68%).

Step C: 2-[4-(1-Ethoxyethoxy)butyl]-2H-thieno[3,2-e]-1,2-thiazine-3-methanol 1,1-dioxide To a solution of the product from Step B (1.01 g, 3.19 mmol) and p-toluenesulfonic acid (0.05 g) in anhydrous THF (30 mL) at 0° C. was added ethyl vinyl ether (0.5 mL, 5.23 mmol) and stirred for 15 min. To this solution was added via syringe DIBAL-H (1M solution in hexanes, 12 mmol); this mixture was stirred for 20 min at which point a solution of potassium sodium tartrate (8.0 g in 30 mL water) was added over 5 min. The resulting mixture was stirred overnight and extracted with ethyl acetate (2×50 mL). The combined extracts were dried (MgSO$_4$) and evaporated to give an oil.

Step D: 2-[4-(1-Ethoxyethoxy)butyl]-3-(4-morpholinylmethyl)-2H-thieno[3,2-e]- 1,2-thiazine 1,1-dioxide To a solution of the product from Step C (2.52 g, 6.98 mmol) and triethylamine (1.41 g, 13.9 mmol) in anhydrous THF (20 mL) at 0° C. was added methanesulfonic anhydride (1.58 g, 9.07 mmol). The ice bath was removed and the reaction mixture was allowed to proceed for 20 min; the reaction mixture was again cooled on ice and morpholine (5 mL) was added. This mixture was stirred for 3 h at ambient temperature, evaporated to dryness and extracted with ethyl acetate (2×100). The combined extracts were dried (MgSO$_4$), evaporated to dryness and purified by column chromatography (silica, 50% ethyl acetate/hexane) to give an oil (2.52 g, 84%).

Step E: 2-(4-Hydroxybutyl)-3-(4-morpholinylmethyl)-2H-thieno[3,2-e]-1,2-thiazine- 6-sulfonamide 1,1-dioxide To a solution of the product from Step D (3.22 g, 7.49 mmol) in anhydrous THF (30 mL) under nitrogen at −70° C. was added n-butyllithium (2.5M in hexanes, 3.30 mL, 8.24 mmol) via syringe over 5 min. The mixture was stirred for 30 min at which point a stream of sulfur dioxide was passed over the surface of the reaction mixture for about 5 min. The mixture was warmed to ambient temperature, evaporated to dryness and the residue was mixed with water (100 mL), cooled on an ice bath at which point hydroxylamine-O-sulfonic acid (1.69 g, 14.9 mmol) and NaOAc (4.07 g, 29.9 mmol) were added; after stirring for 5 min, a saturated solution of sodium bicarbonate (20 mL) was added. The reaction mixture was allowed to warm to ambient temperature and stirred for 16 hr followed by mixing with a saturated solution of sodium bicarbonate (50 mL) and extraction with ethyl acetate (2×200 mL). The combined extracts were washed with 2N HCl (100 mL). The aqueous layer was separated, stirred for 30 min, adjusted to pH 7 by the addition of potassium carbonate, and extracted with ethyl acetate (2×100 mL). The combined extracts were dried (MgSO$_4$), evaporated to dryness and purified by column chromatography (silica, ethyl acetate to 10% ethanol/ethyl acetate, gradient) to give an oil (2.25 g, 69%).

Step F: 3-(4-morpholinylmethyl)-2H-thieno[3,2-e]-1,2-thiazine-6-sulfonamide-2-butanoic Acid 1,1-dioxide Ethyl Ester Hydrochloride To a solution of the product from Step E (1.48 g, 3.39 mmol) in acetone (100 mL) at 0° C. was added Jones reagent (1.1M, 10 mL, 11 mmol). The reaction mixture was stirred at ambient temperature for 2 h and then maintained at a temperature of 5° C. for 16 hr followed by quenching the reaction with an excess of isopropanol and sodium bicarbonate. This suspension was filtered and the filtrate was evaporated to dryness and dissolved in ethanol (15 mL). To this solution was added thionyl chloride (1 mL) and the mixture heated at 50° C. for 1 h and evaporated to dryness. Purification by column chromatography (silica, 50% ethyl acetate/hexane) gave an oil (0.42 g) which was dissolved in ethanol, treated with a 2N ethanolic hydrogen chloride and evaporated to dryness. The residue was triturated with ethyl acetate and dried to give a white solid (0.353 g, 20%): mp 130°–134° C. Analysis. Calculated for $C_{17}H_{26}N_3O_7S_3Cl$: C, 39.56: H, 5.08; N, 8.14. Found: C, 39.41; H, 5.15; N, 7.96.

EXAMPLE 26

2-(2-Hydroxyethyl)-3-(4-morpholinylmethyl)-
2H-thieno[3,2-e]-1, 2-thiazine-6-sulfonamide 1,1-dioxide Step A: 2-(2-Methoxyethyl)-3-(4-morpholinylmethyl)-2H-thieno[3,2-e]-1,2-thiazine- 6-sulfonamide 1,1-dioxide To a solution of 3-hydroxymethyl-2-(2-methoxyethyl)-2H-thieno[3,2-e]-1,2-thiazine- 6-sulfonamide 1,1-dioxide (prepared as described in Example 11.3) (3.40 g, 9.60 mmol) and TEA (1.94 g, 19.2 mmol) in anhydrous THF (40 mL) at 0° C. was added methanesulfonic anhydride (2.17 g, 12.5 mmol). After the addition was completed, the ice bath was removed and the mixture was warmed to ambient temperature, stirred for 30 min, again cooled on an ice bath and morpholine (10 mL) was added. The reaction mixture was stirred for 16 hr and evaporated to dryness. The crude product was mixed with a saturated solution of sodium bicarbonate (100 mL) and extracted with ethyl acetate (2×100 mL). The combined extracts were dried (MgSO$_4$) and evaporated to a residue which was purified by column chromatography (silica, 7% methanol/methylene chloride) to give an oil (1.57 g).

Step B: 2-(2-Hydroxyethyl)-3-(4-morpholinylmethyl)-2H-thieno[3,2-e]-1,2-thiazine- 6-sulfonamide 1,1-dioxide A mixture of the product from Step A (1.56 g), 48% HBr(16 mL) and water (4 mL) was heated at reflux temperature for 18 h, evaporated to dryness, mixed with a saturated solution of sodium bicarbonate (60 mL) and extracted with ethyl acetate (2×80 mL). The combined extracts were dried (MgSO$_4$) and evaporated to a residue which was purified by column chromatography (silica, 5% methanol/methylene chloride) to give a firm foam (0.85 g, 56%): mp 104°–108° C. Analysis. Calculated for $C_{13}H_{19}N_3O_6S_3$ - 0.3H$_2$O: C, 37.63; H, 4.76; N, 10.13. Found: C, 37.61; H, 4.60; N, 10.00.

EXAMPLE 27

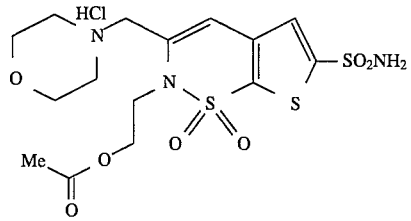

2-[2-(Acetyloxy)ethyl]-3-(4-morpholinylmethyl)-
2H-thieno[3,2-e ]-1, 2-thiazine-6-sulfonamide
1,1-dioxide Hydrochloride A solution of the product from Example 26 (0.41 g, 1.00 mmol), acetic anhydride (0.167 g, 1.60 mmol) in acetic acid (4 mL) was heated at reflux temperature for 1 h, evaporated to dryness, mixed with a saturated solution of sodium bicarbonate (60 mL) and extracted with ethyl acetate (2×80 mL). The combined extracts were dried (MgSO$_4$) and evaporated to a residue which was purified by column chromatography (silica, 80% ethyl acetate/hexane) to give a foam (0.42 g). The foam was dissolved in ethanol, treated with 2N ethanolic hydrogen chloride and evaporated to dryness. Recrystallization from 2-propanol gave a solid (0.185 g, 36%): mp 152°–156° C. Analysis. Calculated for $C_{15}H_{22}N_3O_7S_3Cl$ - 0.33 2-PrOH: C, 37.82; H, 4.89; N, 8.27. Found: C, 37.74; H, 4.91; N, 8.28.

By following the procedures described above and in Example 26, Step B but using instead the product of Example 10 in Example 26, Step B the following compound was prepared:

1. 2-[3-(Acetyloxy)propyl]-3-(4-morpholinylmethyl)-2H-thieno[3,2-e]-1,2-thiazine- 6-sulfonamide 1,1-dioxide, mp 54°–55° C. (foam).

EXAMPLE 28

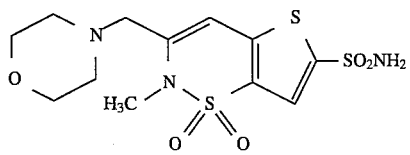

2-Methyl-3-(4-morpholinylmethyl)-
2H-thieno[2,3-e]-1,2-thiazine- 6-sulfonamide 1,1-dioxide Step A: 3,5-Dibromo-2-thiophenecarboxaldehyde To a solution of 2,5-dibromothiophene (20.0 g, 82.7 mmol) in anhydrous THF (200 mL) at −70° C. was added a 1.5M solution of LDA in cyclohexane (60.6 mL, 90.9 mmol) over 10 min. The mixture was stirred for 1 h before anhydrous DMF (18.1 g, 248 mmol) was added. The resulting mixture was stirred overnight, solvent evaporated, the residual oil poured into 2N HCl (200mL), and this mixture was extracted with ethyl acetate (2×200 mL). The combined extracts were dried (MgSO$_4$) and evaporated to give a brown solid (20.21 g, 91%) which was used in the next step without further purification.

Step B: 3,5-Dibromo-2-(1,3-dioxolan-2-yl)-thiophene

A mixture consisting of the product from Step A (11.0 g, 40.7 mmol), TsOH (0.25 g) and ethylene glycol (5.06 g, 81.5 mmol) in toluene (150 mL) was heated at reflux temperature for 1.5 h, water was removed by a Dean-Stark trap. The reaction mixture was cooled and poured into a saturared aqueous solution of sodium bicarbonate (100 mL). The organic layer was separated, dried (MgSO$_4$), and evaporated to dryness. Purification of this crude material by column chromatography (silica, 6% ethyl acetate/hexane) gave 10.33 g of an oil (81%).

Step C: N-[[2-(1,3-dioxolan-2-yl)-3-thienyl]sulfonyl]-N-methyl-glycine Ethyl Ester To a solution of the product from Step B (10.00 g, 31.85 mmol) in anhydrous ether (150 mL) at −75° C. butyllithium (2.5M in hexanes, 13.37 mL, 33.43 mmol) was slowly added over 10 min, maintaining the temperature below −65° C.; a precipitate formed during the addition. After the addition was complete, n-propanol (1.91 g, 31.85 mmol) was added and the solution turned homogenous. A solution of n-butyllithium (2.5M in hexanes, 13.37 mL, 33.43 mmol) was slowly added over 10 min and then sulfur dioxide was passed over the reaction mixture for about 10 min. The mixture was warmed to ambient temperature and evaporated to dryness. The residue was mixed with methylene chloride (150 mL), cooled to 0° C., and N-chlorosuccinimide was added with stirring. After 40 min a saturated aqueous solution of sodium bicarbonate (100 mL) was added to the mixture followed by sacorsine ethyl ester hydrochloride (7.34 g, 47.8 mmol). The organic layer was separated after 30 min, dried (MgSO$_4$), and evaporated to dryness. Column chromatography (silica, 30% ethyl acetate/hexane) gave 5.96 g of a viscous oil (53%).

Step D: Ethyl 2-methyl-2H-thieno[2,3-e]-1,2-thiazine-3-carboxylate 1,1-dioxide

A mixture of the product from Step C (5.86 g, 16.5 mmol) and trifluoroacetic acid (8 mL) in acetone (50 mL) was heated at reflux temperature for 1 h, cooled, and poured into water (100 mL). Acetone was evaporated and the aqueous was combined with a saturated aqueous solution of sodium bicarbonate (50 mL) and this mixture was extracted with ethyl acetate (2×150 mL). The combined extracts were dried (MgSO$_4$) and evaporated to give a crude aldehyde which was dissolved in ethyl acetate (100 mL) followed by the addition of DBN (1 mL) and molecular sieves (5 g). This mixture was heated at reflux temperature for 15 min, cooled, and poured into 2N HCl (50 mL). The organic layer was separated, dried (MgSO$_4$), and evaporated to dryness. Column chromatography (silica, 30% ethyl acetate/hexane) gave 3.60 g (79%) of an off-white solid: mp 87°–89° C.

Step E: 2-Methyl-2H-thieno[2,3-e]-1,2-thiazine-3-methanol 1,1-dioxide

To a solution of the product from Step D (3.16 g, 11.6 mmol) in anhydrous THF (30 mL) at 0° C. was added DIBAL (1.0M, 29.0 mL, 29.0 mmol). This mixture was stirred for 30 min, warmed to ambient temperature, and stirred for an additional 30 min. The mixture was evaporated to dryness and the residue mixed with ethyl acetate (100 mL) and poured into 2N HCl (50 mL). The organic layer was seperated, washed with brine, dried (MgSO$_4$) and evaporated to dryness. Column chromatography (silica, ethyl aectate/hexane) gave a viscous oil which solidified on standing: mp 78°–80° C.

Step F: 3-Hydroxymethyl-2-methyl-2H-thieno[2,3-e]-1,2-thiazine-6-sulfonamide 1,1-dioxide To a solution of the the product from Step E (1.00 g, 4,33 mmol) in anhydrous THF (30 mL) at −70° C. was added n-butyllithium (2.5M in hexanes, 3.81 mL, 9.52 mmol) over 5 min (solution turned cloudy). After an additional 10 min, sulfur dioxide was passed over the reaction for about 10 min, the resulting mixture was warmed to ambient temperature and evaporated to dryness. The residue was dissolved in a mixture of sodium acetate (2.94 g, 21.7 mmol) and water (50 mL) and extracted with ethyl acetate (50 mL) to remove unreacted starting material. The aqueous was cooled on an ice bath and hydroxylamine-O-sulfonic acid (1.47 g, 12.99 ml) was added with stirring. After stirring for 18 hr the reaction mixture was extracted with ethyl acetate (100 mL×2). The combined extracts were dried (MgSO$_4$) and evaporated to dryness. Column chromatography (silica, 50% to 80% ethyl acetate/hexane) gave 0.80 g of a viscous oil (60%).

Step G: 2-Methyl-3-(4-morpholinylmethyl)-2H-thieno[2,3-e]-1,2-thiazine-5-sulfonamide 1,1-dioxide To a solution of the product from Step F (0.78 g, 2.52 mmol) and triethylamine (1.02 g, 10.1 mmol) in anhydrous THF (30 mL) at ambient temperature was added tosyl chloride (0.961 g, 5.04 mmol). After stirring for 4.5 h, morpholine (2 mL) was added and the mixture was stirred for 1 h followed by heating at reflux temperature for 10 min. The volatiles were evaporated and a saturated solution of sodium bicarbonate (80 mL) was added. This mixture was extracted with ethyl acetate (2×100 mL) and the combined extracts were dried (MgSO$_4$) and evaporated to a viscous oil which was purified by column chromatography (silica, 5% to 10% methanol/methylene chloride) to give a solid (0.41 g 43%). Recrystallization from ethyl acetate/methylene chloride gave a yellowish solid: mp 192°–194° C. Analysis. Calculated for $C_{12}H_{17}N_3O_5S_3$: C, 37.98; H, 4.52; N, 11.07. Found: C, 38.09; H, 4.53; N, 11.09.

The following formulations are exemplary and not limiting. They can be administered 1–4 times daily for the control of intraocular pressure according to the discretion of a skilled clinician.

EXAMPLE 29

Ophthalmic Suspension

| Ingredient | Concentration (wt %) |
| --- | --- |
| 2-(2-Methoxyethyl)-3-(4-morpholinylmethyl)-2H-thieno[3,2-e]-1,2-thiazine-6-sulfonamide 1,1-dioxide hydrochloride (Compound) | 3.0% |
| Hydroxypropylmethylcelluose | 0.5% |
| Dibasic Sodium Phosphate | 0.2% |
| Disodium Edetate | 0.01% |
| Sodium Chloride | 0.8% |
| Purified Water | q.s. |
| Benzalkonium Chloride | 0.01% |
| Polysorbate 80 | 0.1% |
| NaOH/HCl | pH 7.02 |

The Compound (0.09 g), benzalkonium chloride (0.03 g), and polysorbate 80 (0.15 g) can be mixed together in water (1.23 g) and ball milled for approximately 4 hr. A hydroxypropylmethylcellulose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 µL). A portion of this vehicle (1.5 mL) can be added to the mixture containing the Compound to furnish the desired suspension.

EXAMPLE 30

Ophthalmic Solution

| Ingredient | Concentration (wt %) |
| --- | --- |
| 3-[[(2-methoxyethyl)(3-methoxypropyl)amino]methyl]-2-methyl-2H-thieno [3,2-e]-1,2-thiazine-6-sulfonamide 1,1-dioxide hydrochloride (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) were mixed together in water (1.44 g) and the pH of the solution was adjusted to 5.02 by the addition of 1N NaOH (10 µL). The hydroxyethylcellulose vehicle was prepared by mixing together monobasic sodium phosphate (0.26 g), dibasic sodium phosphate (0.02 g) and disodium edetate (0.02 g)in water (96.7 g). The benzalkonium chloride (2.0 g) and hydroxyethylcellulose were added to the mixture and the pH was adjusted to 5.01 by the addition of 1N HCl (100 μL). A portion of this vehicle (1.5 g) was added to the solution containing the compound and the pH was adjusted to 5.03 by the addition of 1N NaOH (10 μL).

EXAMPLE 31

Ophthalmic Gel

| Ingredient | Concentration (wt %) |
|---|---|
| 3-[[Bis(2-methoxyethyl)amino]methyl]-2-ethyl-2H-thieno[3,2-e]-1,2-thiazine-6-sulfonamide 1, 1-dioxide hydrochloride (Compound) | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 g), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

Using the procedures described in Equations 1–12, the Examples 1–28 and well known procedures, one skilled in the art can prepare the compounds disclosed herein and those in the Tables. In the Tables the following abbreviations correspond to the indicated structural elements: Me is methyl; Et is ethyl; Pr is propyl; iPr is isopropyl; iBu is isobutyl; Ac is acetyl; OABH is 2-oxa-5-azabicyclo[2.2.1]heptanyl; OABO is 2-oxa-5-azabicyclo[3.2.1]octanyl.

TABLE 1

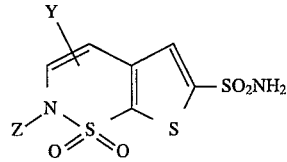

| Z | Y |
|---|---|
| $(CH_2)_2N(CH_2CH_2)_2O$ | H |
| $(CH_2)_2N(CH_2CH_2)_2O$ | 3-Me |
| $(CH_2)_2N(CH_2CH_2)_2O$ | 4-Me |
| $(CH_2)_2N(CH_2CH_2)_2O$ | 3-iBu |
| $(CH_2)_2N(CH_2CH_2)_2O$ | 4-iBu |
| $(CH_2)_2N(CH_2CH_2)_2O$ | 3-$CH_2$OEt |
| $(CH_2)_2N(CH_2CH_2)_2O$ | 4-$CH_2$OEt |
| $(CH_2)_2N(CH_2CH_2OMe)_2$ | 3-$CH_2$OEt |
| $(CH_2)_2N(CH_2CH_2OMe)_2$ | 4-$CH_2$OEt |
| $(CH_2)_2N(CH_2CH_2)_2SO_2$ | 3-$CH_2$OEt |
| $(CH_2)_2N(CH_2CH_2)_2SO_2$ | 4-$CH_2$OEt |
| $(CH_2)_2N(CH_2CH_2)_2O$ | 3-$CH_2$OCO-iPr |
| $(CH_2)_2N(CH_2CH_2)_2O$ | 4-$CH_2$OCO-iPr |
| $(CH_2)_2N(CH_2CH_2)_2O$ | 3-$CO_2$-iPr |
| $(CH_2)_2N(CH_2CH_2OMe)_2$ | 3-$CO_2$-iPr |
| $(CH_2)_2N(CH_2CH_2)_2O$ | 3-CONHMe |
| $(CH_2)_2$-(5-OABO) | H |
| $CH_2CCCH_2N(CH_2CH_2)_2O$ | H |
| $CH_2CCCH_2N(CH_2CH_2)_2O$ | 3-$CH_2$OMe |
| $(CH_2)_2N(CH_2CH_2)_2O$ | 3-$CH_2$O$(CH_2)_2$OMe |
| $(CH_2)_2N(CH_2CH_2)_2O$ | 3-$CH_2C_6H_4$-(4-OMe) |
| $(CH_2)_2N(CH_3)CH_2CH_2F$ | H |
| $(CH_2)_2N(CH_3)CH_2CH_2F$ | 3-$CH_2$OEt |
| $(CH_2)_2N(CH_3)CH_2CH_2F$ | 4-$CH_2$OEt |
| $C_6H_3$-(4-OH)-(3-$CH_2NMe_2$) | H |
| $C_6H_3$-(4-OH)-(3-$CH_2NMe_2$) | 3-Me |

TABLE 1-continued

| Z | Y |
|---|---|
| $C_6H_3$-(4-OH)-(3-$CH_2NMe_2$) | 4-Me |
| $C_6H_3$-(4-OH)-(3-$CH_2NMe_2$) | 3-$CH_2$OEt |
| $C_6H_3$-(4-OH)-(3-$CH_2NMe_2$) | 4-$CH_2$OEt |
| $C_6H_3$-(4-OH)-(3-$CH_2NMe_2$) | 3-$CH_2OCH_2C_6H_5$ |
| $C_6H_4$-(4-OMe) | 3-$CH_2N(CH_2CH_2)_2O$ |
| $C_6H_4$-(4-OMe) | 4-$CH_2N(CH_2CH_2)_2O$ |
| $C_6H_4$-(3-OH) | 3-$CH_2N(CH_2CH_2)_2O$ |
| $C_6H_4$-(4-$CH_2$OH) | 3-CHhd 2$N(CH_2CH_2)_2O$ |
| $C_6H_4$-(4-$CH_2$OMe) | 3-$CH_2N(CH_2CH_2)_2O$ |
| $C_6H_4$-(4-$CH_2CH_2$OMe) | 3-$CH_2N(CH_2CH_2)_2O$ |
| $C_6H_4$-(3-$CH_2CH_2$OH) | 3-$CH_2N(CH_2CH_2)_2O$ |
| $C_6H_3$-(3,4-OMe) | 3-$CH_2N(CH_2CH_2)_2O$ |
| $C_6H_4$-(4-$CONMe_2$) | 3-$CH_2N(CH_2CH_2)_2O$ |
| $C_6H_4$-(4-$SO_2$Me) | 3-$CH_2N(CH_2CH_2)_2O$ |
| $C_6H_4$-NHCOMe) | 3-$CH_2N(CH_2CH_2)_2O$ |
| $CH_2C_6H_4$-(4-OH) | 3-$CH_2N(CH_2CH_2)_2O$ |
| $CH_2C_6H_4$-(4-OH) | 4-$CH_2N(CH_2CH_2)_2O$ |
| $CH_2C_6H_4$-(3-OMe) | 3-$CH_2N(CH_2CH_2)_2O$ |
| $CH_2C_6H_4$-(4-$CH_2$OMe) | 3-$CH_2N(CH_2CH_2)_2O$ |
| $CH_2C_6H_4$-(4-$CH_2$OMe) | 4-$CH_2N(CH_2CH_2)_2O$ |
| $CH_2C_6H_4$-(3-$CH_2$OH) | 3-$CH_2N(CH_2CH_2)_2O$ |
| $CH_2C_6H_3$-(3,4-OMe) | 3-$CH_2N(CH_2CH_2)_2O$ |
| $CH_2C_6H_3$-(3,4-OH) | 3-$CH_2N(CH_2CH_2)_2O$ |
| $CH_2C_6H_3$-(4-OH)-(3-$CH_2NMe_2$) | H |
| $CH_2C_6H_3$-(4-OH)-(3-$CH_2NMe_2$) | 3-$CH_2$OMe |
| $CH_2C_6H_3$-(4-OH)-(3-$CH_2NMe_2$) | 4-$CH_2$OMe |
| $CH_2C_6H_3$ — (4-OH)-(3-$CH_2NMe_2$) | 3-$CO_2$-iPr |
| Me | 3-$CH_2$ — (5-PABH) |
| $(CH_2)_2$OMe | 3-$CH_2N(CH_2CH_2)_2O$ |
| $(CH_2)_3$SMe | 3-$CH_2N(CH_2CH_2)_2O$ |
| $(CH_2)_3SO_2$Me | 3-$CH_2N(CH_2CH_2)_2O$ |
| Pr | 4-$CH_2N(CH_2CH_2)_2O$ |
| $(CH_2)_4$OH | 3-$CH_2N(CH_2CH_2)_2O$ |
| $CH_2$ — $C_3H_5$ | 3-$CH_2N(CH_2CH_2)_2O$ |
| $CH_2$ — $C_3H_5$ | 4-$CH_2N(CH_2CH_2)_2O$ |
| iBu | 3-$CH_2N(CH_2CH_2)_2O$ |
| $CH_2CHCHCH_2$OMe | 3-$CH_2N(CH_2CH_2)_2O$ |
| $(CH_2)_3CO_2$-iPr | 3-$CH_2N(CH_2CH_2)_2O$ |
| $(CH_2)_2CONH(CH_2)$OH | 3-$CH_2N(CH_2CH_2)_2O$ |
| $CH_2CCCH_2$OMe | 3-$CH_2N(CH_2CH_2)_2O$ |
| $CH_2$-(pyridin-4-yl) | 3-$CH_2N(CH_2CH_2OMe)_2$ |
| $CH_2$-(pyridin-3-yl) | 4-$CH_2N(CH_2CH_2OMe)_2$ |
| $CH_2$-[(2-$CO_2$Et)-pyridin-4-yl] | 3-$CH_2N(CH_2CH_2OMe)_2$ |
| 2-(4-morpholinyl)-thiazol-4-yl | 3-$CH_2N(CH_2CH_2OMe)_2$ |
| 5-(4-morpholinyl)methyl-thiadiazol-2-yl | 3-$CH_2$OEt |
| $CH_2$-(thien-2-yl) | 3-$CH_2N(CH_2CH_2OMe)_2$ |
| $CH_2$[(5-$CO_2$-iPr)-thien-2-yl] | 3-$CH_2N(CH_2CH_2OMe)_2$ |
| $CH_2$-(thiazol-2-yl) | 3-$CH_2N(CH_2CH_2OMe)_2$ |
| pyridin-3-yl-(5-$OCH_3$) | 3-$CH_2N(CH_2CH_2)_2O$ |
| $(CH_2)_2$-(4-Ac-piperazinyl) | 3-$CH_2$OEt |
| $(CH_2)_3$OMe | 3-$CH_2N(Me)CH_2CCCH_2$ |
| $(CH_2)_3$OMe | 3-$CH_2N(CH_2CH_2)_2S$ |
| $(CH_2)_3$OMe | 3-$CH_2N(CH_2CH_2)_2SO_2$ |
| Chd 6$H_4$-(4-OMe) | 3-$CH_2N(Me)CH_2CH_2F$ |
| $C_6H_4$-(4-OMe) | 4-$CH_2N(Me)CH_2CH_2F$ |
| $CH_2$Chd 6$H_4$-[4-$N(CH_2CH_2)_2O$] | 3-$CH_2N(Me)CH_2CH_2F$ |
| $C_6H_4$-[4-$N(CH_2CH_2)_2O$] | 3-$CH_2N(CH_2CH_2OMe)_2$ |
| $C_6H_4$-[3-$N(CH_2CH_2)_2O$] | 3-$CH_2N(CH_2CH_2OMe)_2$ |
| $C_6H_4$-(4-OMe) | 3-$CH_2NHCH_2$CCH |
| $(CH_2)_3$OMe | 3-$CH_2NHCH_2$CCH |
| $C_6H_4$-(3-OH) | 3-$CH_2NHCH_2$CCH |
| $C_6H_4$-(4-OMe) | 4-$CH_2N(Me)CH_2$CCH |
| $CH_2C_6H_4$-(3-OMe) | 4-$CH_2N(Me)CH_2$CCH |
| $C_6H_3$-(3,5-OMe) | 3-$CH_2N(CH_2CH_2)_2O$ |
| $(CH_2)_3CO_2$Et | 3-$CH_2N(CH_2CH_2OMe)_2$ |
| $(CH_2)_3CO_2CH(CH_3)_2$ | 3-$CH_2N(CH_2CH_2)_2O$ |
| $(CH_2)_3C(=O)$NHMe | 3-$CH_2N(Me)CH_2CH_2$OMe |

TABLE 1-continued

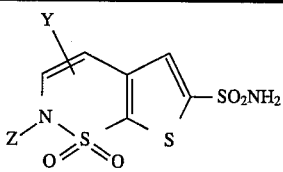

| Z | Y |
|---|---|
| (CH$_2$)$_2$C(=O)NHC$_3$H$_5$ | 3-CH$_2$N(CH$_2$CH$_2$)$_2$O |
| (CH$_2$)$_3$C(=O)NHCH$_2$CH$_2$OH | 3-CH$_2$N(CH$_2$CH$_2$)$_2$O |
| (CH$_2$)$_3$O(C=O)Me | 3-CH$_2$N(CH$_2$CH$_2$)$_2$O |
| (CH$_2$)$_3$O(C=O)CH$_2$CH$_2$OH | 3-CH$_2$N(CH$_2$CH$_2$OMe)$_2$ |
| (CH$_2$)$_2$O(C=O)CH(Me)$_2$ | 3-CH$_2$N(CH$_2$CH$_2$)$_2$O |
| (CH$_2$)$_2$O(C=O)C$_3$H$_5$ | 3-CH$_2$N(Me)CH$_2$CH$_2$OMe |
| (CH$_2$)$_2$NH(C=O)Me | 3-CH$_2$N(Me)CH$_2$CH$_2$OMe |
| (CH$_2$)$_2$NH(C=O)CH$_2$CH$_2$OH | 3-CH$_2$N(CH$_2$CH$_2$)$_2$O |
| (CH$_2$)$_2$OMe | 3-CH$_2$N(CH$_2$CH$_2$OMe) (CH$_2$)$_3$CO$_2$Et |
| (CH$_2$)$_2$OMe | 3-(CH$_2$)$_2$N(Me)CH$_2$CO$_2$Et |
| (CH$_2$)$_2$OMe | 3-CH$_2$N(CH$_2$CH$_2$OMe)$_2$ |
| (CH$_2$)$_2$OH | 3-CH$_2$N(CH$_2$CH$_2$OMe) (CH$_2$)$_3$OMe |
| (CH$_2$)$_2$OH | 3-CH$_2$NHCH$_2$CO$_2$iPr |
| (CH$_2$)$_2$OH | 3-CH$_2$NHOH |
| (CH$_2$)$_2$OH | 3-(CH$_2$)$_2$N(OH)Et |
| (CH$_2$)$_2$O(C=O)CH$_2$N(CH$_2$CH$_2$)$_2$O | 3-CH$_2$N(CH$_2$CH$_2$)$_2$O |
| (CH$_2$)$_2$N(CH$_2$CH$_2$)$_2$O | 3-CH$_2$OCH$_2$CH$_2$OCH$_3$ |
| (CH$_2$)$_2$N(CH$_2$CH$_2$)$_2$O | 3-CH$_2$CH$_2$CH$_2$OH |
| (CH$_2$)$_3$OH | 3-CH$_2$N(CH$_2$CH$_2$)$_2$O |

TABLE 2

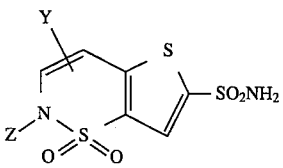

| Z | Y |
|---|---|
| (CH$_2$)$_2$N(CH$_2$CH$_2$)$_2$O | H |
| (CH$_2$)$_2$N(CH$_2$CH$_2$)$_2$O | 3-Me |
| (CH$_2$)$_2$N(CH$_2$CH$_2$)$_2$O | 4-Me |
| (CH$_2$)$_2$N(CH$_2$CH$_2$)$_2$O | 3-iBu |
| (CH$_2$)$_2$N(CH$_2$CH$_2$)$_2$O | 4-iBu |
| (CH$_2$)$_2$N(CH$_2$CH$_2$)$_2$O | 3-CH$_2$OEt |
| (CH$_2$)$_2$N(CH$_2$CH$_2$)$_2$O | 4-CH$_2$OEt |
| (CH$_2$)$_2$N(CH$_2$CH$_2$OMe)$_2$ | 3-CH$_2$OEt |
| (CH$_2$)$_2$N(CH$_2$CH$_2$OMe)$_2$ | 4-CH$_2$OEt |
| (CH$_2$)$_2$N(CH$_2$CH$_2$)$_2$SO$_2$ | 3-CH$_2$OEt |
| (CH$_2$)$_2$N(CH$_2$CH$_2$)$_2$SO$_2$ | 4-CH$_2$OEt |
| (CH$_2$)$_2$N(CH$_2$CH$_2$)$_2$O | 3-CH$_2$OCO-iPr |
| (CH$_2$)$_2$N(CH$_2$CH$_2$)$_2$O | 4-CH$_2$OCO-iPr |
| (CH$_2$)$_2$N(CH$_2$CH$_2$)$_2$O | 3-CO$_2$-iPr |
| (CH$_2$)$_2$N(CH$_2$CH$_2$OMe)$_2$ | 3-CO$_2$-iPr |
| (CH$_2$)$_2$N(CH$_2$CH$_2$)$_2$O | 3-CONHMe |
| (CH$_2$)$_2$-(5-OABO) | H |
| CH$_2$CCCH$_2$N(CH$_2$CH$_2$)$_2$O | H |
| CH$_2$CCCH$_2$N(CH$_2$CH$_2$)$_2$O | 3-CH$_2$OMe |
| (CH$_2$)$_2$N(CH$_2$CH$_2$)$_2$O | 3-CH$_2$O(CH$_2$)$_2$OMe |
| (CH$_2$)$_2$N(CH$_2$CH$_2$)$_2$O | 3-CH$_2$C$_6$H$_4$-(4-OMe) |
| (CH$_2$)$_2$N(CH$_3$)CH$_2$CH$_2$F | H |
| (CH$_2$)$_2$N(CH$_3$)CH$_2$CH$_2$F | 3-CH$_2$OEt |
| (CH$_2$)$_2$N(CH$_3$)CH$_2$CH$_2$F | 4-CH$_2$OEt |
| C$_6$H$_3$-(4-OH)-(3-CH$_2$NMe$_2$) | H |
| C$_6$H$_3$-(4-OH)-(3-CH$_2$NMe$_2$) | 3-Me |
| C$_6$H$_3$-(4-OH)-(3-CH$_2$NMe$_2$) | 4-Me |
| C$_6$H$_3$-(4-OH)-(3-CH$_2$NMe$_2$) | 3-CH$_2$OEt |
| C$_6$H$_3$-(4-OH)-(3-CH$_2$NMe$_2$) | 4-CH$_2$OEt |
| C$_6$H$_3$-(4-OH)-(3-CH$_2$NMe$_2$) | 3-CH$_2$OCH$_2$C$_6$H$_5$ |
| C$_6$H$_4$-(4-OMe) | 3-CH$_2$N(CH$_2$CH$_2$)$_2$O |
| C$_6$H$_4$-(4-OMe) | 4-CH$_2$N(CH$_2$CH$_2$)$_2$O |
| C$_6$H$_4$-(3-OH) | 3-CH$_2$N(CH$_2$CH$_2$)$_2$O |

TABLE 2-continued

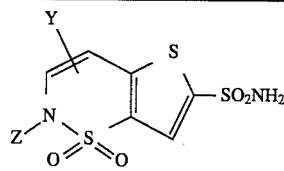

| Z | Y |
|---|---|
| C$_6$H$_4$-(4-CH$_2$OH) | 3-CHhd 2N(CH$_2$CH$_2$)$_2$O |
| C$_6$H$_4$-(3-CH$_2$OMe) | 3-CH$_2$N(CH$_2$CH$_2$)$_2$O |
| C$_6$H$_4$-(4-CH$_2$CH$_2$OMe) | 3-CH$_2$N(CH$_2$CH$_2$)$_2$O |
| C$_6$H$_4$-(3-CH$_2$CH$_2$OH) | 3-CH$_2$N(CH$_2$CH$_2$)$_2$O |
| C$_6$H$_3$-(3,4-OMe) | 3-CH$_2$N(CH$_2$CH$_2$)$_2$O |
| C$_6$H$_4$-(4-CONMe$_2$) | 3-CH$_2$N(CH$_2$CH$_2$)$_2$O |
| C$_6$H$_4$-(4-SO$_2$Me) | 3-CH$_2$N(CH$_2$CH$_2$)$_2$O |
| C$_6$H$_4$-NHCOMe) | 3-CH$_2$N(CH$_2$CH$_2$)$_2$O |
| CH$_2$C$_6$H$_4$-(4-OH) | 3-CH$_2$N(CH$_2$CH$_2$)$_2$O |
| CH$_2$C$_6$H$_4$-(4-OH) | 4-CH$_2$N(CH$_2$CH$_2$)$_2$O |
| CH$_2$C$_6$H$_4$-(3-OMe) | 3-CH$_2$N(CH$_2$CH$_2$)$_2$O |
| CH$_2$C$_6$H$_4$-(4-CH$_2$OMe) | 3-CH$_2$N(CH$_2$CH$_2$)$_2$O |
| CH$_2$C$_6$H$_4$-(4-CH$_2$OMe) | 4-CH$_2$N(CH$_2$CH$_2$)$_2$O |
| CH$_2$C$_6$H$_4$-(3-CH$_2$OH) | 3-CH$_2$N(CH$_2$CH$_2$)$_2$O |
| CH$_2$C$_6$H$_3$-(3,4-OMe) | 3-CH$_2$N(CH$_2$CH$_2$)$_2$O |
| CH$_2$C$_6$H$_3$-(3,4-OMe) | 3-CH$_2$N(CH$_2$CH$_2$)$_2$O |
| CH$_2$C$_6$H$_3$-(4-OH)-(3-CH$_2$NMe$_2$) | H |
| CH$_2$C$_6$H$_3$-(4-OH)-(3-CH$_2$NMe$_2$) | 3-CH$_2$OMe |
| CH$_2$C$_6$H$_3$-(4-OH)-(3-CH$_2$NMe$_2$) | 4-CH$_2$OMe |
| CH$_2$C$_6$H$_3$—(4-OH)-(3-CH$_2$NMe$_2$) | 3-CO$_2$-iPr |
| Me | 3-CH$_2$—(5-PABH) |
| (CH$_2$)$_2$OMe | 3-CH$_2$N(CH$_2$CH$_2$)$_2$O |
| (CH$_2$)$_3$SMe | 3-CH$_2$N(CH$_2$CH$_2$)$_2$O |
| (CH$_2$)$_3$SO$_2$Me | 3-CH$_2$N(CH$_2$CH$_2$)$_2$O |
| Pr | 4-CH$_2$N(CH$_2$CH$_2$)$_2$O |
| (CH$_2$)$_4$OH | 3-CH$_2$N(CH$_2$CH$_2$)$_2$O |
| CH$_2$—C$_3$H$_5$ | 3-CH$_2$N(CH$_2$CH$_2$)$_2$O |
| CH$_2$—C$_3$H$_5$ | 4-CH$_2$N(CH$_2$CH$_2$)$_2$O |
| iBu | 3-CH$_2$N(CH$_2$CH$_2$)$_2$O |
| CH$_2$CHCHCH$_2$OMe | 3-CH$_2$N(CH$_2$CH$_2$)$_2$O |
| (CH$_2$)$_3$CO$_2$-iPr | 3-CH$_2$N(CH$_2$CH$_2$)$_2$O |
| (CH$_2$)$_2$CONH(CH$_2$)OH | 3-CH$_2$N(CH$_2$CH$_2$)$_2$O |
| CH$_2$CCCH$_2$OMe | 3-CH$_2$N(CH$_2$CH$_2$)$_2$O |
| CH$_2$-(pyridin-4-yl) | 3-CH$_2$N(CH$_2$CH$_2$OMe)$_2$ |
| CH$_2$-(pyridin-3-yl) | 4-CH$_2$N(CH$_2$CH$_2$OMe)$_2$ |
| CH$_2$-[(2-CO$_2$Et)-pyridin-4-yl] | 3-CH$_2$N(CH$_2$CH$_2$OMe)$_2$ |
| 2-(4-morpholinyl)-thiazol-4-yl | 3-CH$_2$N(CH$_2$CH$_2$OMe)$_2$ |
| 5-(4-morpholinyl)methyl-thiadiazol-2-yl | 3-CH$_2$OEt |
| CH$_2$-(thien-2-yl) | 3-CH$_2$N(CH$_2$CH$_2$OMe)$_2$ |
| CH$_2$[(5-CO$_2$-iPr)-thien-2-yl] | 3-CH$_2$N(CH$_2$CH$_2$OMe)$_2$ |
| CH$_2$-(thiazol-2-yl) | 3-CH$_2$N(CH$_2$CH$_2$OMe)$_2$ |
| pyridin-3-yl-(5-OCH$_3$) | 3-CH$_2$N(CH$_2$CH$_2$)$_2$O |
| (CH$_2$)$_2$-(4-Ac-piperazinyl) | 3-CH$_2$OEt |
| (CH$_2$)$_3$OMe | 3-CH$_2$N(Me)CH$_2$CCCH$_2$ |
| (CH$_2$)$_3$OMe | 3-CH$_2$N(CH$_2$CH$_2$)$_2$S |
| (CH$_2$)$_3$OMe | 3-CH$_2$N(CH$_2$CH$_2$)$_2$SO$_2$ |
| Chd 6H$_4$-(4-OMe) | 3-CH$_2$N(Me)CH$_2$CH$_2$F |
| C$_6$H$_4$-(4-OMe) | 4-CH$_2$N(Me)CH$_2$CH$_2$F |
| CH$_2$Chd 6H$_4$-[4-N(CH$_2$CH$_2$)$_2$O] | 3-CH$_2$N(Me)CH$_2$CH$_2$F |
| C$_6$H$_4$-[4-N(CH$_2$CH$_2$)$_2$O] | 3-CH$_2$N(CH$_2$CH$_2$OMe)$_2$ |
| C$_6$H$_4$-[3-N(CH$_2$CH$_2$)$_2$O] | 3-CH$_2$N(CH$_2$CH$_2$OMe)$_2$ |
| C$_6$H$_4$-(4-OMe) | 3-CH$_2$NHCH$_2$CCH |
| (CH$_2$)$_3$OMe | 3-CH$_2$NHCH$_2$CCH |
| C$_6$H$_4$-(3-OH) | 3-CH$_2$NHCH$_2$CCH |
| C$_6$H$_4$-(4-OMe) | 4-CH$_2$N(Me)CH$_2$CCH |
| CH$_2$C$_6$H$_4$-(3-OMe) | 4-CH$_2$N(Me)CH$_2$CCH |
| C$_6$H$_3$-(3,5-OMe) | 3-CH$_2$N(CH$_2$CH$_2$)$_2$O |
| (CH$_2$)$_3$CO$_2$Et | 3-CH$_2$N(CH$_2$CH$_2$OMe)$_2$ |
| (CH$_2$)$_3$CO$_2$CH(CH$_3$)$_2$ | 3-CH$_2$N(CH$_2$CH$_2$)$_2$O |
| (CH$_2$)$_3$C(=O)NHMe | 3-CH$_2$N(Me)CH$_2$CH$_2$OMe |
| (CH$_2$)$_2$C(=O)NHC$_3$H$_5$ | 3-CH$_2$N(CH$_2$CH$_2$)$_2$O |
| (CH$_2$)$_3$C(=O)NHCH$_2$CH$_2$OH | 3-CH$_2$N(CH$_2$CH$_2$)$_2$O |
| (CH$_2$)$_3$O(C=O)Me | 3-CH$_2$N(CH$_2$CH$_2$)$_2$O |
| (CH$_2$)$_3$O(C=O)CH$_2$CH$_2$OH | 3-CH$_2$N(CH$_2$CH$_2$OMe)$_2$ |
| (CH$_2$)$_2$O(C=O)CH(Me)$_2$ | 3-CH$_2$N(CH$_2$CH$_2$)$_2$O |
| (CH$_2$)$_2$O(C=O)C$_3$H$_5$ | 3-CH$_2$N(Me)CH$_2$CH$_2$OMe |
| (CH$_2$)$_2$NH(C=O)Me | 3-CH$_2$N(Me)CH$_2$CH$_2$OMe |
| (CH$_2$)$_2$NH(C=O)CH$_2$CH$_2$OH | 3-CH$_2$N(CH$_2$CH$_2$)$_2$O |

TABLE 2-continued

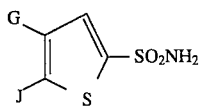

| Z | Y |
|---|---|
| (CH$_2$)$_2$OMe | 3-CH$_2$N(CH$_2$CH$_2$OMe)(CH$_2$)$_3$CO$_2$Et |
| (CH$_2$)$_2$OMe | 3-(CH$_2$)$_2$N(Me)CH$_2$CO$_2$Et |
| (CH$_2$)$_2$OMe | 3-CH$_2$N(CH$_2$CH$_2$OMe)$_2$ |
| (CH$_2$)$_2$OH | 3-CH$_2$N(CH$_2$CH$_2$OMe)(CH$_2$)$_3$OMe |
| (CH$_2$)$_2$OH | 3-CH$_2$NHCH$_2$CO$_2$iPr |
| (CH$_2$)$_2$OH | 3-CH$_2$NHOH |
| (CH$_2$)$_2$OH | 3-(CH$_2$)$_2$N(OH)Et |
| (CH$_2$)$_2$O(C=O)CH$_2$N(CH$_2$CH$_2$)$_2$O | 3-CH$_2$N(CH$_2$CH$_2$)$_2$O |
| (CH$_2$)$_2$N(CH$_2$CH$_2$)$_2$O | 3-CH$_2$OCH$_2$CH$_2$OCH$_3$ |
| (CH$_2$)$_2$N(CH$_2$CH$_2$)$_2$O | 3-CH$_2$CH$_2$CH$_2$OH |
| (CH$_2$)$_3$OH | 3-CH$_2$N(CH$_2$CH$_2$)$_2$O |

We claim:

1. A compound of Formula I:

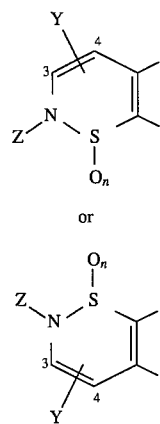

Wherein G, J and the two atoms of the thiophene ring to which they are attached form a six-membered ring chosen from

[structure with Y, Z, N, S, O$_n$]

or

[structure with O$_n$, S, N, Z, Y]

wherein Z is Z$^1$ or Z$^2$ and, Z$^1$ is

C$_{1-8}$alkyl;

C$_{1-3}$alkyl-C$_{3-6}$cycloalkyl;

CH$_2$C(=O)R$^7$; CH$_2$C(=O)NR$^2$R$^3$; CH$_2$CN;

C$_{2-8}$alkyl substituted with one or more of hydroxyl, C$_{1-4}$alkoxy, C$_{2-4}$alkoxy-C$_{1-4}$alkoxy, OC(=O)R$^1$, N(R$^2$)C(=O)R$^1$, halogen, CN, NR$^2$R$^3$, SO$_n$R$^4$ or C(=O)R$^5$;

C$_{1-4}$alkyl substituted with an aromatic group chosen from phenyl or Q, either of which is unsubstituted or substituted with one or more of C$_{1-4}$alkyl, C$_{1-4}$alkoxy, hydroxy, halogen, nitrile, NR$^2$R$^3$, SO$_n$R$^4$, C(=O)R$^5$ or C$_{1-4}$alkyl which is substituted with hydroxy, NR$^2$R$^3$, halogen, CO$_2$R$^1$ or C$_{1-3}$alkoxy;

C$_{3-8}$alkenyl unsubstituted or substituted with hydroxyl, C$_{1-4}$alkoxy or NR$^2$R$^3$;

C$_{3-8}$alkynyl unsubstituted or substituted with hydroxyl, C$_{1-4}$alkoxy or NR$^2$R$^3$;

Z$^2$ is an aromatic group chosen from phenyl or Q, either of which is unsubstituted or substituted with one or more of C$_{1-4}$alkyl, C$_{1-4}$alkoxy, hydroxy halogen, nitrile, NR$^2$R$^3$, SO$_n$R$^4$, C(=O)R$^5$, or C$_{1-4}$alkyl which is substituted with hydroxy, NR$^2$R$^3$, halogen or C$_{1-3}$alkoxy;

is hydrogen;

C$_{3-8}$alkyl;

C$_{1-6}$alkyl substituted with one or more of hydroxyl, C$_{1-4}$alkoxy, C$_{2-4}$alkoxy-C$_{1-4}$alkoxy, OC(=O)R$^1$, N(R$^2$)C(=O)R$^1$, halogen, CN, NR$^2$R$^3$, SO$_n$R$^4$, or C(=O)R$^5$;

C$_{1-4}$alkyl substituted with an aromatic group chosen from phenyl or Q, either of which is unsubstituted or substituted with one or more of C$_{1-4}$alkyl, C$_{1-4}$alkoxy, hydroxy, halogen, nitrile, NR$^2$R$^3$, SO$_n$R$^4$, C(=O)R$^5$ or C$_{1-4}$alkyl which is substituted with hydroxy, NR$^2$R$^3$, halogen, CO$_2$R$^1$ or C$_{1-3}$alkoxy;

C$_{3-8}$alkenyl unsubstituted or substituted with hydroxyl, C$_{1-4}$alkoxy or NR$^2$R$^3$;

C$_{3-8}$alkynyl unsubstituted or substituted with hydroxyl, C$_{1-4}$alkoxy or NR$^2$R$^3$;

R$^1$ is C$_{1-6}$alkyl;

C$_{1-6}$alkyl substituted with hydroxyl, halogen, C$_{1-4}$alkoxy, NR$^2$R$^5$ or C(=O)R$^5$;

phenyl which is unsubstituted or substituted with one or more of C$_{1-4}$ alkyl, alkoxy, hydroxy or halogen;

R$^2$ and R$^3$ are independently chosen from hydrogen;

C$_{1-4}$alkyl; CH$_2$CN;

C$_{1-3}$alkyl-C$_{3-6}$cycloalkyl;

C$_{3-6}$cycloalkyl;

C$_{2-4}$alkyl substituted with hydroxyl, halogen, CN, C$_{1-4}$alkoxy or C(=O)R$^5$;

hydroxyl;

C$_{1-4}$alkoxy;

C$_{2-4}$alkoxy substituted with hydroxyl, NR$^2$R$^3$, halogen or C$_{1-4}$alkoxy;

C$_{3-8}$alkenyl unsubstituted or substituted with hydroxy, or C$_{1-4}$alkoxy;

C$_{3-8}$alkynyl unsubstituted or substituted with hydroxyl, or C$_{1-4}$alkoxy;

or further R$^2$ and R$^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, C$_{1-4}$alkoxy, C(=O)R$^5$, C$_{1-4}$alkyl, C$_{1-4}$alkyl substituted with hydroxyl, halogen, C$_{1-4}$alkoxy, C(=O)R$^5$, or on nitrogen with C$_{1-4}$alkoxy, C(=O)R$^5$, SO$_n$R$^4$, C$_{1-4}$alkyl or C$_{1-4}$alkyl substituted with hydroxyl, halogen, C$_{1-4}$alkoxy or C(=O)R$^5$;

R$^4$ is C$_{1-4}$alkyl;

C$_{2-4}$alkyl substituted with hydroxyl, NR$^2$R$^3$ or C$_{1-3}$alkoxy;

R$^5$ is C$_{1-6}$alkyl;

C$_{1-6}$alkyl substituted with hydroxyl, halogen, SO$_n$R$^4$, C$_{1-4}$alkoxy, NR$^2$R$^3$ or C(=O)R$^6$;

C$_{1-4}$alkyl substituted with an aromatic group chosen from phenyl or Q, either of which is unsubstituted or substituted with one or more of C$_{1-4}$alkyl, C$_{1-4}$alkoxy, hydroxy, halogen, nitrile, NR$^2$R$^3$, SO$_n$R$^4$ or C$_{1-4}$alkyl which is substituted with hydroxy, NR$^2$R$^3$, halogen or C$_{1-3}$alkoxy;

hydroxyl;
$C_{1-4}$alkoxy;
$C_{2-4}$alkoxy substituted with hydroxyl, $NR^2R^3$, halogen or $C_{1-4}$alkoxy;
$NR^2R^3$;

$R^6$ is $C_{1-4}$alkyl;
$C_{1-4}$alkoxy;
amino;
$C_{1-3}$alkylamino;
$(C_{1-3}$alkyl$)_2$amino;

$R^7$ is hydroxyl, $C_{1-4}$ alkoxy, $C_{1-4}$ alkoxy substituted with hydroxyl, $NR^2R^3$ or $C_{1-4}$ alkoxy;

n is 0, 1, or 2; and

Q is a heterocyclic ring selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

2. The compound of claim 1 having the formula:

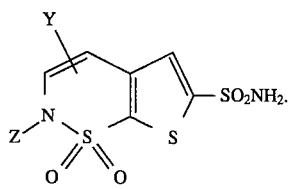

3. The compound of claim 1 having the formula:

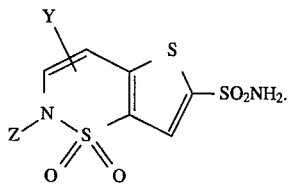

4. The compound of claim 2 wherein Y is at position 3 and Z is $Z^1$.

5. The compound of claim 2 wherein Y is at position 3 and Z is $Z^2$.

6. The compound of claim 4 wherein Y is $C_{1-6}$alkyl substituted with $NR^2R^3$.

7. The compound of claim 5 wherein Y is $C_{1-6}$alkyl substituted with $NR^2R^3$.

8. The compound of claim 2 wherein Y is hydrogen and Z is $Z^1$ or $Z^2$.

9. A compound chosen from the group consisting of:

2-[2-(4-Morpholinyl)ethyl]-2H-thieno[3,2-e]-1,2-thiazine-6-sulfonamide 1,1-dioxide;

2-Methyl-3-(4-morpholinylmethyl)-2H-thieno[3,2-e]-1,2-thiazine-6-sulfonamide 1,1-dioxide;

2-[2-[Bis(2-methoxyethyl)amino]ethyl]-2H-thieno[3,2-e]-1,2-thiazine-6-sulfonamide 1,1-dioxide;

2-(3-Methoxypropyl)-3-(4-morpholinylmethyl)-2H-thieno[3,2-e]-1,2-thiazine-6-sulfonamide 1,1-dioxide;

3-[[Bis(2-methoxyethyl)amino]methyl]-2-(4-methoxyphenylmethyl)-2H-thieno[3,2-e]-1,2-thiazine-6-sulfonamide 1,1-dioxide;

2-(1-Methylethyl)-3-(4-morpholinylmethyl)-2H-thieno[3,2-e]-1,2-thiazine-6-sulfonamide 1,1-dioxide;

3-(4-Morpholinylmethyl)-2-propyl-2H-thieno[3,2-e]-1,2-thiazine-6-sulfonamide 1,1-dioxide;

2-(2-Methylpropyl)-3-(4-morpholinylmethyl)-2H-thieno[3,2-e]-1,2-thiazine-6-sulfonamide 1,1 dioxide;

2-(Cyclopropylmethyl)-3-(4-morpholinylmethyl)-2H-thieno[3,2-e]-1,2-thiazine-6-sulfonamide 1,1 dioxide;

2-(3-Hydroxyphenyl)-3-(4-morpholinylmethyl)-2H-thieno[3,2-e]-1,2-thiazine-6-sulfonamide 1,1-dioxide;

3-(4-morpholinylmethyl)-2-[4-(4-morpholinyl)phenyl]-2H-thieno[3,2-e]- 1,2-thiazine- 6 sulfonamide 1,1-dioxide;

6-(Aminosulfonyl)-3-(4-morpholinylmethyl)-2H-thieno[3,2-e]-1,2-thiazine-2-butanoic acid 1,1-dioxide ethyl ester;

2-(2-Hydroxyethyl)-3-(4-morpholinylmethyl)-2H-thieno[3,2-e]-1,2-thiazine-2-sulfonamide 1,1-dioxide;

2-Methyl-3-(4-morpholinylmethyl)-2H-thieno[2,3-e]-1,2-thiazine-6-sulfonamide 1,1-dioxide;

2-Ethyl-3-(4-morpholinylmethyl)-2H-thieno[3,2-e]-1,2-thiazine-6-sulfonamide 1,1-dioxide;

3-[[Bis(2-methoxyethyl)amino]methyl]-2-ethyl-2H-thieno[3,2-e]-1,2-thiazine- 6-sulfonamide 1,1-dioxide;

3-[[Bis(2-methoxyethyl)amino]methyl]-2-(2-methoxyethyl)-2H-thieno[3,2-e]- 1,2-thiazine- 6-sulfonamide 1,1-dioxide;

3-[[(2-methoxyethyl)(3-methoxypropyl)amino]methyl]-2-methyl-2H-thieno[3,2-e]- 1,2-thiazine-6-sulfonamide 1,1-dioxide;

2-[(2-Acetyloxy)ethyl]-3-(4-morpholinylmethyl)-2H-thieno[3,2-e]-1,2-thiazine- 6-sulfonamide 1,1-dioxide.

10. A compound of the formula:

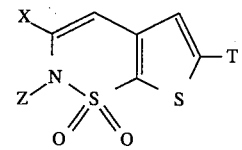

wherein T is H, Cl, Br, or $SO_2NH_2$;

X is $CO_2$-$C_{1-4}$ alkyl or $CH_2OH$;

wherein Z is $Z^1$ or $Z^2$ and, $Z^1$ is
$C_{1-8}$alkyl;
$C_{1-3}$alkyl-$C_{3-6}$cycloalkyl;
$CH_2C(=O)R^7$; $CH_2C(=O)NR^2R^3$; $CH_2CN$;
$C_{2-8}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, CN, $NR^2R^3$, $SO_nR^4$ or $C(=O)R^5$;

$C_{1-4}$alkyl substituted with an aromatic group chosen from phenyl or Q, either of which is unsubstituted or substituted with one or more of $C_{1-4}$alkyl, $C_{1-4}$alkoxy, hydroxy, halogen, nitrile, $NR^2R^3$, $SO_nR^4$, $C(=O)R^5$ or $C_{1-4}$alkyl which is substituted with hydroxy, $NR^2R^3$, halogen, $CO_2R^1$ or $C_{1-3}$alkoxy;

$C_{3-8}$alkenyl unsubstituted or substituted with hydroxyl, $C_{1-4}$alkoxy or $NR^2R^3$;

$C_{3-8}$alkynyl unsubstituted or substituted with hydroxyl, $C_{1-4}$alkoxy or $NR^2R^3$;

$Z^2$ is an aromatic group chosen from phenyl or Q, either of which is unsubstituted or substituted with one or more of $C_{1-4}$alkyl, $C_{1-4}$alkoxy, hydroxy halogen, nitrile, $NR^2R^3$, $SO_nR^4$, $C(=O)R^5$, or $C_{1-4}$alkyl which is substituted with hydroxy, $NR^2R^3$, halogen or $C_{1-3}$alkoxy;

$R^1$ is $C_{1-6}$alkyl;
$C_{1-6}$alkyl substituted with hydroxyl, halogen, $C_{1-4}$alkoxy, $NR^2R^3$ or $C(=O)R^5$;
phenyl which is unsubstituted or substituted with one or more of $C_{1-4}$ alkyl, alkoxy, hydroxy or halogen;

$R^2$ and $R^3$ are independently chosen from hydrogen;
$C_{1-4}$alkyl; $CH_2CN$;
$C_{1-3}$alkyl-$C_{3-6}$cycloalkyl;
$C_{3-6}$cycloalkyl;
$C_{2-4}$alkyl substituted with hydroxyl, halogen, CN, $C_{1-4}$alkoxy or $C(=O)R^5$;
hydroxyl;
$C_{1-4}$alkoxy;
$C_{2-4}$alkoxy substituted with hydroxyl, $NR^2R^3$, halogen or $C_{1-4}$alkoxy;
$C_{3-8}$alkenyl unsubstituted or substituted with hydroxy, or $C_{1-4}$alkoxy;
$C_{3-8}$alkynyl unsubstituted or substituted with hydroxyl, or $C_{1-4}$alkoxy;

or further $R^2$ and $R^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$alkoxy, $C(=O)R^5$, $SO_nR^4$, $C_{1-4}$alkyl or $C_{1-4}$alkyl substituted with hydroxyl, halogen, $C_{1-4}$alkoxy or $C(=O)R^5$;

$R^4$ is $C_{1-4}$alkyl;
$C_{2-4}$alkyl substituted with hydroxyl, halogen, $NR^2R^3$ or $C_{1-3}$alkoxy;

$R^5$ is $C_{1-6}$alkyl;
$C_{1-6}$alkyl substituted with hydroxyl, halogen, $SO_nR^4$, $C_{1-4}$alkoxy, $NR^2R^3$ or $C(=O)R^6$;
$C_{1-4}$alkyl substituted with an aromatic group chosen from phenyl or Q, either of which is unsubstituted or substituted with one or more of $C_{1-4}$alkyl, $C_{1-4}$alkoxy, hydroxy, halogen, nitrile, $NR^2R^3$, $SO_nR^4$ or $C_{1-4}$alkyl which is substituted with hydroxy, $NR^2R^3$, halogen or $C_{1-3}$alkoxy;
hydroxyl;
$C_{1-4}$alkoxy;
$C_{2-4}$alkoxy substituted with hydroxyl, $NR^2R^3$, halogen or $C_{1-4}$alkoxy;
$NR^2R^3$;

$R^6$ is $C_{1-4}$alkyl;
$C_{1-4}$alkoxy;
amino;
$C_{1-3}$alkylamino;
$(C_{1-3}$alkyl$)_2$amino;

$R^7$ is hydroxyl, $C_{1-4}$ alkoxy, $C_{1-4}$ alkoxy substituted with hydroxyl, $NR^2R^3$ or $C_{1-4}$ alkoxy;

n is 0, 1, or 2; and

Q is a heterocyclic ring selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

11. The compound of claim 10 wherein T is H, Cl, or $SO_2NH_2$ and X is $CH_2OH$.

12. A compound of the formula:

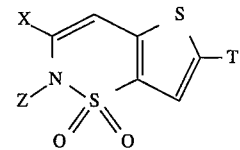

wherein T is H, Cl, Br, or $SO_2NH_2$;
X is $CO_2$- $C_{1-4}$ alkyl or $CH_2OH$;
wherein Z is $Z^1$ or $Z^2$ and, $Z^1$ is
$C_{1-8}$alkyl;
$C_{1-3}$alkyl-$C_{3-6}$cycloalkyl;
$CH_2C(=O)R^7$; $CH_2C(=O)NR^2R^3$; $CH_2CN$;
$C_{2-8}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, CN, $NR^2R^3$, $SO_nR^4$ or $C(=O)R^5$;
$C_{1-4}$alkyl substituted with an aromatic group chosen from phenyl or Q, either of which is unsubstituted or substituted with one or more of $C_{1-4}$alkyl, $C_{1-4}$ alkoxy, hydroxy, halogen, nitrile, $NR^2R^3$, $SO_nR^4$, $C(=O)R^5$ or $C_{1-4}$alkyl which is substituted with hydroxy, $NR^2R^3$, halogen, $CO_2R^1$ or $C_{1-3}$alkoxy;
$C_{3-8}$alkenyl unsubstituted or substituted with hydroxyl, $C_{1-4}$alkoxy or $NR^2R^3$;
$C_{3-8}$alkynyl unsubstituted or substituted with hydroxyl, $C_{1-4}$alkoxy or $NR^2R^3$;

$Z^2$ is an aromatic group chosen from phenyl or Q, either of which is unsubstituted or substituted with one or more of $C_{1-4}$alkyl, $C_{1-4}$alkoxy, hydroxy halogen, nitrile, $NR^2R^3$, $SO_nR^4$, $C(=O)R^5$, or $C_{1-4}$alkyl which is substituted with hydroxy, $NR^2R^3$, halogen or $C_{1-3}$alkoxy;

$R^1$ is $C_{1-6}$alkyl;
$C_{1-6}$alkyl substituted with hydroxyl, halogen, $C_{1-4}$alkoxy, $NR^2R^3$ or $C(=O)R^5$;
phenyl which is unsubstituted or substituted with one or more of $C_{1-4}$ alkyl, alkoxy, hydroxy or halogen;

$R^2$ and $R^3$ are independently chosen from hydrogen;
$C_{1-4}$alkyl; $CH_2CN$;
$C_{1-3}$alkyl-$C_{3-6}$cycloalkyl;
$C_{3-6}$cycloalkyl;
$C_{2-4}$alkyl substituted with hydroxyl, halogen, CN, $C_{1-4}$alkoxy or $C(=O)R^5$;
hydroxyl;
$C_{1-4}$alkoxy;
$C_{2-4}$alkoxy substituted with hydroxyl, $NR^2R^3$, halogen or $C_{1-4}$alkoxy;
$C_{3-8}$alkenyl unsubstituted or substituted with hydroxy, or $C_{1-4}$alkoxy;
$C_{3-8}$alkynyl unsubstituted or substituted with hydroxyl, or $C_{1-4}$alkoxy;

or further $R^2$ and $R^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$alkoxy, $C(=O)R^5$, $SO_nR^4$, $C_{1-4}$alkyl or $C_{1-4}$alkyl substituted with hydroxyl, halogen, $C_{1-4}$alkoxy or $C(=O)R^5$;

$R^4$ is $C_{1-4}$alkyl;

$C_{2-4}$alkyl substituted with hydroxyl, halogen, $NR^2R^3$ or $C_{1-3}$alkoxy;

$R^5$ is $C_{1-6}$alkyl;
  $C_{1-6}$alkyl substituted with hydroxyl, halogen, $SO_nR^4$, $C_{1-4}$alkoxy, $NR^2R^3$ or $C(=O)R^6$;
  $C_{1-4}$alkyl substituted with an aromatic group chosen from phenyl or Q, either of which is unsubstituted or substituted with one or more of $C_{1-4}$alkyl, alkoxy, hydroxy, halogen, nitrile, $NR^2R^3$, $SO_nR^4$ or $C_{1-4}$alkyl which is substituted with hydroxy, $NR^2R^3$, halogen or $C_{1-3}$alkoxy;
  hydroxyl;
  $C_{1-4}$alkoxy;
  $C_{2-4}$alkoxy substituted with hydroxyl, $NR^2R^3$, halogen or $C_{1-4}$alkoxy;
  $NR^2R^3$;

$R^6$ is $C_{1-4}$alkyl;
  $C_{1-4}$alkoxy;
  amino;
  $C_{1-3}$alkylamino;
  $(C_{1-3}$alkyl$)_2$amino;

$R^7$ is hydroxyl, $C_{1-4}$ alkoxy, $C_{1-4}$ alkoxy substituted with hydroxyl, $NR^2R^3$ or $C_{1-4}$ alkoxy;

n is 0, 1, or 2; and

Q is a heterocyclic ring selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

13. A Compound of claim 12 wherein T is H, Cl, or $SO_2NH_2$ and X is $CH_2OH$.

14. A method for controlling intraocular pressure by topically administering a pharmaceutically acceptable amount of the compound of claim 1.

15. A method for controlling intraocular pressure by topically administering a pharmaceutically acceptable amount of the compound of claim 9.

16. A compound having the formula:

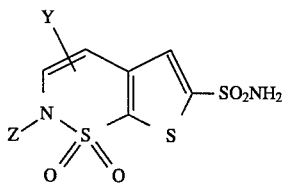

wherein Z is $CH_2C(=O)R^7$; $CH_2C(=O)NR^2R^3$; $CH_2CN$;
  $C_{2-8}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, CN, $NR^2R^3$, $SO_nR^4$ or $C(=O)R^5$;

Y is $C_{1-6}$alkyl substituted with $NR^2R^3$;

$R^1$ is $C_{1-6}$alkyl;
  $C_{1-6}$alkyl substituted with hydroxyl, halogen, $C_{1-4}$alkoxy or $NR^2R^3$;

$R^2$ and $R^3$ are independently chosen from hydrogen;
  $C_{1-4}$alkyl; $CH_2CN$;
  $C_{1-3}$alkyl-$C_{3-6}$cycloalkyl;
  $C_{3-6}$cycloalkyl;
  $C_{2-4}$alkyl substituted with hydroxyl, CN, $C_{1-4}$alkoxy or $C(=O)R^5$;
  hydroxyl;
  $C_{1-4}$alkoxy;
  $C_{2-4}$alkoxy substituted with hydroxyl, $NR^2R^3$, halogen or $C_{1-4}$alkoxy;
  $C_{3-8}$alkenyl unsubstituted or substituted with hydroxy, or $C_{1-4}$alkoxy;
  $C_{3-8}$alkynyl unsubstituted or substituted with hydroxyl, or $C_{1-4}$alkoxy;
  or further $R^2$ and $R^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$ alkoxy, $C(=O)R^5$, $SO_nR^4$, $C_{1-4}$alkyl or $C_{1-4}$alkyl substituted with hydroxyl, halogen, $C_{1-4}$ alkoxy or $C(=O)R^5$;

$R^4$ is $C_{1-4}$alkyl;
  $C_{2-4}$alkyl substituted with hydroxyl, halogen, $NR^2R^3$ or $C_{1-3}$alkoxy;

$R^5$ is $C_{1-6}$alkyl;
  $C_{1-6}$alkyl substituted with hydroxyl, halogen, $SO_nR^4$, $C_{1-4}$alkoxy or $NR^2R^3$;
  hydroxyl;
  $C_{1-4}$alkoxy;
  $C_{2-4}$alkoxy substituted with hydroxyl, $NR^2R^3$, halogen or $C_{1-4}$alkoxy;
  $NR^2R^3$;

$R^7$ is hydroxyl, $C_{1-4}$ alkoxy, $C_{1-4}$ alkoxy substituted with hydroxyl, $NR^2R^3$ or $C_{1-4}$ alkoxy;

n is 0, 1, or 2.

17. A compound of claim 16 wherein Y is at position 3.

18. A compound having the formula:

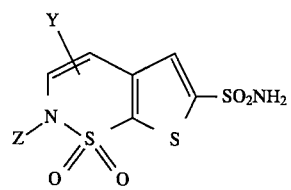

wherein Z is $Z^1$ or $Z^2$; and $Z^1$ is
  $CH_2C(=O)R^7$; $CH_2C(=O)NR^2R^3$;
  $C_{2-8}$alkyl substituted with one or more of hydroxyl, $C_{1-4}$alkoxy, $OC(=O)R^1$, $N(R^2)C(=O)R^1$, halogen, $NR^2R^3$ or $C(=O)R^5$;
  $C_{1-4}$alkyl substituted with phenyl which is substituted with one or more of $C_{1-4}$ alkoxy, hydroxy or $C_{1-4}$alkyl which is substituted with $NR^2R^3$;
  $C_{3-8}$alkenyl substituted with $NR^2R^3$;
  $C_{3-8}$alkynyl substituted with $NR^2R^3$;

$Z^2$ is an aromatic group chosen from phenyl or Q, either of which is substituted with one or more of $C_{1-4}$alkyl, $C_{1-4}$alkoxy, hydroxy, halogen, $NR^2R^3$, $C(=O)R^5$, or $C_{1-4}$alkyl which is substituted with $NR^2R^3$;

Y is hydrogen;

$R^1$ is $C_{1-6}$alkyl substituted with $NR^2R^3$ or $C(=O)R^5$;

$R^2$ and $R^3$ are independently chosen from hydrogen;
  $C_{1-4}$alkyl; $CH_2CN$;
  $C_{1-3}$alkyl-$C_{3-6}$cycloalkyl;
  $C_{3-6}$cycloalkyl;
  $C_{2-4}$alkyl substituted with hydroxyl, halogen, CN, $C_{1-4}$alkoxy or $C(=O)R^5$;
  hydroxyl;
  $C_{1-4}$alkoxy;

$C_{2-4}$alkoxy substituted with hydroxyl, $NR^2R^3$, halogen or $C_{1-4}$alkoxy;

$C_{3-8}$alkenyl unsubstituted or substituted with hydroxy, or $C_{1-4}$alkoxy;

$C_{3-8}$alkynyl unsubstituted or substituted with hydroxyl, or $C_{1-4}$alkoxy;

or further $R^2$ and $R^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$alkoxy, $C(=O)R^5$, $C_{1-4}$ alkyl or $C_{1-4}$alkyl substituted with hydroxyl, halogen, $C_{1-4}$alkoxy or $C(=O)R^5$;

$R^5$ is $C_{2-4}$alkoxy substituted with $NR^2R^3$;
$NR^2R^3$;

$R^7$ is $C_{1-4}$ alkoxy substituted with $NR^2R^3$;

and Q is a heterocyclic ring selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

19. A compound of claim 18 where Z is $Z^1$; and $Z^1$ is $C_{2-8}$alkyl substituted with $NR^2R^3$, $OC(=O)R^1$, $N(R^2)C(=O)R^1$, or $C(=O)R^5$;

$R^1$ is $C_{1-6}$alkyl substituted with $NR^2R^3$ or $C(=O)R^5$;

$R^2$ and $R^3$ are independently chosen from hydrogen;
$C_{1-4}$alkyl; $CH_2CN$;
$C_{1-3}$alkyl-$C_{3-6}$cycloalkyl;
$C_{3-6}$cycloalkyl;
$C_{2-4}$alkyl substituted with hydroxyl, halogen, CN, $C_{1-4}$alkoxy or $C(=O)R^5$;
hydroxyl;
$C_{1-4}$alkoxy;
$C_{2-4}$alkoxy substituted with hydroxyl, $NR^2R^3$, halogen or $C_{1-4}$alkoxy;
$C_{3-8}$alkenyl unsubstituted or substituted with hydroxy, or $C_{1-4}$alkoxy;
$C_{3-8}$alkynyl unsubstituted or substituted with hydroxyl, or $C_{1-4}$alkoxy;

or further $R^2$ and $R^3$ together with the nitrogen atom to which they are attached can form a heterocyclic ring selected from the group consisting of pyrrolidine, oxazolidine, morpholine, thiomorpholine, thiomorpholine 1,1-dioxide, piperazine, 2-oxa- 5-azabicyclo[2.2.1]heptane, 2-oxa-5-azabicyclo[3.2.1]octane, thiazolidine, or thiazolidine 1,1-dioxide, which can be unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$alkoxy, $C(=O)R^5$, $C_{1-4}$ alkyl or $C_{1-4}$alkyl substituted with hydroxyl, halogen, $C_{1-4}$alkoxy or $C(=O)R^5$; and $R^5$ is $C_{2-4}$alkoxy substituted with $NR^2R^3$.

20. A compound having the formula:

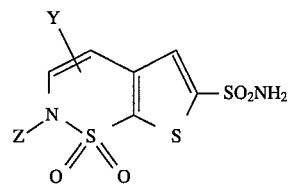

wherein Z is $Z^1$; and $Z^1$ is $C_{2-8}$alkyl substituted with $NR^2R^3$;

Y is $C_{1-6}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, or $C(=O)R^5$;

$R^1$ is $C_{1-6}$alkyl;
$C_{1-6}$alkyl substituted with hydroxyl, halogen or $C_{1-4}$alkoxy;
phenyl which is unsubstituted or substituted with one or more of $C_{1-4}$ alkyl, alkoxy, hydroxy or halogen;

$R^2$ and $R^3$ are independently chosen from hydrogen;
$C_{1-4}$alkyl; $CH_2CN$;
$C_{1-3}$alkyl-$C_{1-6}$cycloalkyl;
$C_{3-6}$cycloalkyl;
$C_{2-4}$alkyl substituted with hydroxyl, halogen, CN, $C_{1-4}$alkoxy or $C(=O)R^5$;
hydroxyl;
$C_{1-4}$alkoxy;
$C_{2-4}$alkoxy substituted with hydroxyl, $NR^2R^3$, halogen or $C_{1-4}$alkoxy;
$C_{3-8}$alkenyl unsubstituted or substituted with hydroxy, or $C_{1-4}$alkoxy;

or further $R^2$ and $R^3$ together with the nitrogen atom to which they are attached form a heterocyclic ring selected from the group consisting of pyrrolidine, oxazolidine, morpholine, thiomorpholine, thiomorpholine 1,1-dioxide, piperazine, 2-oxa-5-azabicyclo[2.2.1]heptane, 2-oxa-5-azabicyclo[3.2.1]octane, thiazolidine, or thiazolidine 1,1-dioxide, which is unsubstituted or substituted on carbon with hydroxyl, (=O), halogen, $C_{1-4}$alkoxy, $C(=O)R^5$, $C_{1-4}$alkyl, $C_{1-4}$alkyl substituted with hydroxyl, halogen, $C_{1-4}$alkoxy, $C(=O)R^5$, or on nitrogen with $C_{1-4}$ alkoxy, $C(=O)R^5$, $C_{1-4}$alkyl or $C_{1-4}$alkyl substituted with hydroxyl, halogen, $C_{1-4}$alkoxy or $C(=O)R^5$; and $R^5$ is $C_{1-4}$alkoxy;
$C_{2-4}$alkoxy substituted with hydroxyl, halogen or $C_{1-4}$alkoxy.

21. A compound of claim 20 where Y is at position 3.

22. A composition for controlling intraocular pressure comprising a pharmaceutically effective amount of the compound of claim 1 in a pharmaceutically acceptable carrier.

23. A composition for controlling intraocular pressure comprising a pharmaceutically effective amount of the compound of claim 9 in a pharmaceutically acceptable carrier.

* * * * *